(12) United States Patent
Espensen et al.

(10) Patent No.: US 10,766,897 B2
(45) Date of Patent: Sep. 8, 2020

(54) IMIDAZO[4,5-C]PYRIDINE AND PYRROLO[2,3-C]PYRIDINE DERIVATIVES AS SSAO INHIBITORS

(71) Applicant: PROXIMAGEN, LLC, Plymouth, MN (US)

(72) Inventors: Max Espensen, Cambridge (GB); Lee Patient, Linton (GB); David Evans, Royston (GB); Iain Simpson, Cambridge (GB); Edward Savory, Cambourne (GB)

(73) Assignee: PROXIMAGEN, LLC, Plymouth, MN (US)

( * ) Notice: Subject to any disclaimer, the term of this patent is extended or adjusted under 35 U.S.C. 154(b) by 0 days.

(21) Appl. No.: 16/542,792

(22) Filed: Aug. 16, 2019

(65) Prior Publication Data

US 2020/0002335 A1    Jan. 2, 2020

Related U.S. Application Data

(63) Continuation of application No. 15/911,935, filed on Mar. 5, 2018, now Pat. No. 10,428,066, which is a continuation of application No. 15/592,556, filed on May 11, 2017, now Pat. No. 9,951,068, which is a continuation of application No. 14/775,046, filed as application No. PCT/GB2014/050765 on Mar. 13, 2014, now Pat. No. 9,676,769.

(30) Foreign Application Priority Data

Mar. 13, 2013  (GB) .................................. 1304526.5

(51) Int. Cl.
| C07D 471/04 | (2006.01) |
| A61K 31/40 | (2006.01) |
| A61K 31/4745 | (2006.01) |
| A61K 31/495 | (2006.01) |
| A61K 31/501 | (2006.01) |
| A61K 31/506 | (2006.01) |
| C07C 53/18 | (2006.01) |

(52) U.S. Cl.
CPC ............ *C07D 471/04* (2013.01); *A61K 31/40* (2013.01); *A61K 31/4745* (2013.01); *A61K 31/495* (2013.01); *A61K 31/501* (2013.01); *A61K 31/506* (2013.01); *C07C 53/18* (2013.01)

(58) Field of Classification Search
CPC .................................................. C07D 471/04
See application file for complete search history.

(56) References Cited

U.S. PATENT DOCUMENTS

| 7,405,300 | B2 | 7/2008 | Jiang et al. |
| 9,428,498 | B2 | 8/2016 | Espensen et al. |
| 9,580,415 | B2 | 2/2017 | Patient et al. |
| 9,676,769 | B2 | 6/2017 | Espensen et al. |
| 9,951,068 | B2 * | 4/2018 | Espensen ............ C07D 471/04 |
| 10,065,954 | B2 | 9/2018 | Espensen et al. |
| 10,428,066 | B2 * | 10/2019 | Espensen ................ C07C 53/18 |
| 2005/0054631 | A1 | 3/2005 | Jiang et al. |
| 2014/0275040 | A1 | 9/2014 | Espensen et al. |
| 2015/0258101 | A1 | 9/2015 | Espensen et al. |
| 2016/0024080 | A1 | 1/2016 | Patient et al. |
| 2016/0046622 | A1 | 2/2016 | Espensen et al. |
| 2016/0326172 | A1 | 11/2016 | Espensen et al. |

FOREIGN PATENT DOCUMENTS

| JP | 2001-520227 A | 10/2001 |
| WO | 99/20624 A1 | 4/1999 |
| WO | 2002/038153 A1 | 5/2002 |
| WO | 2003/006003 A1 | 1/2003 |
| WO | 2005/014530 A | 2/2005 |
| WO | 2007/120528 A2 | 10/2007 |
| WO | 2010/031789 A1 | 3/2010 |
| WO | 2010/031791 A1 | 3/2010 |
| WO | 2010/064020 A1 | 6/2010 |
| WO | 2010/117935 A1 | 10/2010 |
| WO | 2011/113798 A2 | 9/2011 |
| WO | 2012/146667 A1 | 11/2012 |
| WO | 2013/037411 A1 | 3/2013 |
| WO | 2013/038189 A1 | 3/2013 |
| WO | 2013/078254 A1 | 5/2013 |
| WO | 2014/140591 A1 | 9/2014 |

(Continued)

OTHER PUBLICATIONS

CAS Registry No. 340159-15-1, Jun. 8, 2001, Compound 2-(2,3-dihydro-1,3-dimethyl-1H-benzimidazol-2-yl)-3-phenyl-3H-imidazo[4,5-c]pyridine.

(Continued)

*Primary Examiner* — Rebecca L Anderson

(74) *Attorney, Agent, or Firm* — Greenblum & Bernstein, P.L.C.

(57) ABSTRACT

The compounds of formula (I) are inhibitors of SSAO activity

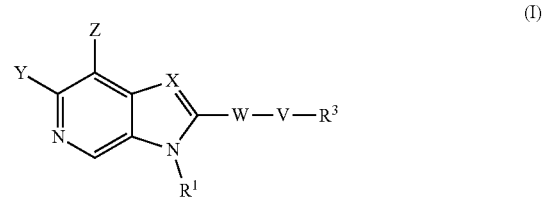

wherein V, W, X, Y, Z, $R^1$ and $R^2$ are as defined in the claims.

27 Claims, No Drawings

(56) References Cited

FOREIGN PATENT DOCUMENTS

| WO | 2014/140592 A1 | 9/2014 |
|---|---|---|
| WO | 2015189534 A1 | 12/2015 |

OTHER PUBLICATIONS

Database Registry [online], Chemical Abstract Service, Columbus, Ohio, US; Jan. 19, 2011, XP002723294, database accession No. 1259952-23-2 abstract.
Dunkel et al., "Semicarbazide-sensitive amine oxidase/vascular adhesion protein-1: a patent survey," Expert Opin. Ther. Patents, 21(9): 1453-1471 (2011).
International Search Report dated Apr. 28, 2014 for PCT/GB2014/050764.
International Search Report dated Dec. 15, 2015 for PCT/GB2015/052690.
International Search Report dated May 8, 2014 for PCT/GB2014/050765.
International Search Report dated Dec. 15, 2015 for PCT/GB2015/052691.
Melkonyan et al., "One-pot synthesis of substituted indoles via titanium(iv) alkoxide mediated imine formation—copper-catalyzed N-arylation," RSC Advances, vol. 3, No. 22, Mar. 21, 2013, p. 8388, XP055113497.
UKIPO Search Report dated Aug. 28, 2013 from GB Application No. 1304527.3.
UKIPO Search Report dated Aug. 21, 2013 from GB Application No. 1304526.5.
UKIPO Search Report dated Jan. 13, 2016 from GB Application No. 1416444.6.
Wilson et al., "Copper- and Palladium-Catalyzed Amidation Reactions for the Synthesis of Substituted Imidazo[4,5-c] pyridines," Journal of Organic Chemistry, vol. 79, No. 5, Feb. 6, 2014, pp. 2203-2212, XP055113503.
Jordan, "Tamoxifen: A Most Unlikely Pioneering Medicine", Drug Discovery 2003, 2:205-213.
Hackam et al., "Translation of Research Evidence From Animals to Humans", JAMA 2006, 296(14):1731-1732.
Kamila et al., "Synthesis of Novel Peridobenzimidazoles Bonded to Indoleorbenzo[b]thiophenestructures", The Open Organic Chemistry Journal 2011, 5:127-134.
Simone, Oncology: Introduction, Cecil Textbook of Medicine, 20th Edition, pp. 1004-1010 (1996).
Peet et al., "Bioluminescent Method for Assaying Multiple Semicarbazide-Sensitive Amine Oxidase (SSAO) Family Members in Both 96- and 384-Well Formats", J of Biomolecular Screening 16(9):1106-1111 (2011).
Garpenstrand et al., "Serum Semicarbazide-Sensitive Amine Oxidase (SSAO) Activity Correlates with VEGF in Non-Small-Cell Lung Cancer Patients", Medical Oncology, 21(3):241-250 (2004).
Pannecoeck et al., "Vascular adhesion protein-1: Role in human pathology and application as a biomarker", Critical Reviews in Clinical Laboratory Sciences, 52(6):284-300 (2015).
Noda et al., "Inhibition of vascular adhesion protein-1 suppresses endotoxin-induced uveitis". The FASEB Journal, 22:1094-1103 (2008).
Dunkel et al., "Semicarbazide-Sensitive Amine Oxidase/Vascular Adhesion Protein-1: Recent Developments Concerning Substrates and Inhibitors of a Promising Therapeutic Target", Current Medicinal Chemistry, 15:1827-1839 (2008).

\* cited by examiner

IMIDAZO[4,5-C]PYRIDINE AND PYRROLO[2,3-C]PYRIDINE DERIVATIVES AS SSAO INHIBITORS

CROSS-REFERENCE TO RELATED APPLICATIONS

The present application is a Continuation Application of U.S. application Ser. No. 15/911,935, filed Mar. 5, 2018, which is a continuation of U.S. application Ser. No. 15/592,556, filed May 11, 2017, which issued as U.S. Pat. No. 9,951,068 on Apr. 24, 2018, which is a continuation of U.S. application Ser. No. 14/775,046, filed Sep. 11, 2015, which issued as U.S. Pat. No. 9,676,769 on Jun. 13, 2017, which is a national stage application under 35 U.S.C. § 371 of PCT Patent Application No. PCT/GB2014/050765, filed Mar. 13, 2014, which claims priority to United Kingdom Patent Application No. 1304526.5 filed Mar. 13, 2013, the disclosures of which are incorporated by reference herein in their entireties.

FIELD OF THE INVENTION

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumour growth.

BACKGROUND ART

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein. Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

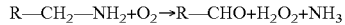

$$R\text{—}CH_2\text{—}NH_2 + O_2 \rightarrow R\text{—}CHO + H_2O_2 + NH_3$$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Mátyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61(Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557]. It has recently been shown that circulating human and rodent SSAO originates from the tissue-bound form [Göktürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Matyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium

[Salmi et al., *Immunity* 2001, 14(3), 265-276; Salmi & Jalkanen, in *"Adhesion Molecules: Functions and Inhibition"* K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

WO2007146188 teaches that blocking SSAO activity inhibits leucocyte recruitment, reduces the inflammatory response, and is expected to be beneficial in prevention and treatment of seizures, for example, in epilepsy.

O'Rourke et al (J Neural Transm. 2007; 114(6):845-9) examined the potential of SSAO inhibitors in neurological diseases, having previously demonstrated the efficacy of SSAO inhibition in a rat model of stroke. An SSAO inhibitor is tested on relapsing-remitting experimental autoimmune encephalomyelitis (EAE), a mouse model that shares many characteristics with human multiple sclerosis. The data demonstrates the potential clinical benefit of small molecule anti-SSAO therapy in this model and therefore in treatment of human multiple sclerosis.

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in *"Adhesion Molecules: Functions and Inhibition"* K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases. VAP-1 has also been implicated in the progression and maintenance of fibrotic diseases including those of the liver and lung. Weston and Adams (J Neural Transm. 2011, 118(7), 1055-64) have summarised the experimental data implicating VAP-1 in liver fibrosis, and Weston et al (EASL Poster 2010) reported that blockade of VAP-1 accelerated the resolution of carbon tetrachloride induced fibrosis. In addition VAP-1 has been implicated in inflammation of the lung (e.g. Singh et al., 2003, Virchows Arch 442:491-495) suggesting that VAP-1 blockers would reduce lung inflammation and thus be of benefit to the treatment of cystic fibrosis by treating both the pro-fibrotic and pro-inflammatory aspects of the disease.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88.; Irjala H, Salmi M, Alanen K, Gre'nman R, Jalkanen S (2001), *Immunol.* 166, 6937-6943; Forster-Horvath C, Dome B, Paku S, et al. (2004), Melanoma Res. 14, 135-40.). One report (Marttila-Ichihara F, Castermans K, Auvinen K, Oude Egbrink M G, Jalkanen S, Griffioen A W, Salmi M. (2010), J Immunol. 184, 3164-3173.) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

Small molecules of different structural classes have previously been disclosed as SSAO inhibitors, for example in WO 02/38153 (tetrahydroimidazo[4,5-c]pyridine derivatives), in WO 03/006003 (2-indanylhydrazine derivatives), in WO 2005/014530 (allylhydrazine and hydroxylamine (aminooxy) compounds) and in WO 2007/120528 (allylamino compounds). Additional SSAO inhibitors are disclosed in PCT/EP2009/062011 and PCT/EP2009/062018. Additional SSAO inhibitors are disclosed in PCT/GB2012/052265.

Patent application PCT/US2012/066153 (published as WO2013/078254) discloses compounds apparently useful as inhibitors of serine/threonine protein kinases. The compounds are structurally related to the claimed compounds, and have a bicyclic heteroaryl ring system substituted with a phenyl-cyclobutaneamine substituent.

The invention described here relates to a new class of SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

DETAILED DESCRIPTION OF THE INVENTION

It has surprisingly been found that the compounds of formula (I) below are inhibitors of SSAO. They are therefore useful for the treatment or prevention of diseases in which inhibition of SSAO activity is beneficial, such as inflammation, inflammatory diseases, immune or autoimmune disorders, and inhibition of tumour growth.

According to a first aspect of the invention there is provided a compound of formula (I) or a pharmaceutically acceptable salt, or N-oxide thereof:

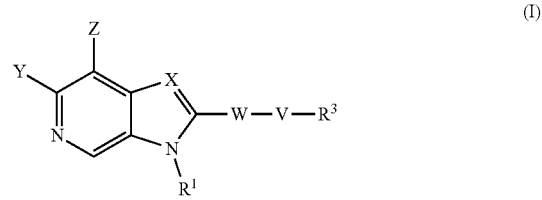

Wherein:

Y is selected from hydrogen, hydroxyl, —NH$_2$, —NH—C$_{1-4}$-alkyl, —NH-halo-C$_{1-4}$-alkyl, or —C$_{1-4}$-alkoxy;

Z is selected from hydrogen, halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, or —NHhalo-C$_{1-4}$-alkyl;

R$^1$ is a phenyl ring, or a 5 or 6-membered heteroaryl ring, either ring being optionally substituted with one or more substituents selected from halogen, cyano, C$_{1-4}$-alkyl, halo-C$_{1-4}$-alkyl, cyano-C$_{1-4}$-alkyl, a 3-7 membered cycloalkyl ring, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$; wherein R$^{4A}$, R$^{4B}$ R$^5$ and R$^6$ are each independently selected from hydrogen, C$_{1-4}$-alkyl or halo-C$_{1-4}$-alkyl, or R$^{4A}$ and R$^{4B}$ together with the nitrogen to which they are attached form a 3-7 membered cyclic amino group, optionally substituted by one or more substituents selected from: halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, —NHhalo-C$_{1-4}$-alkyl;

X is selected from —N= or —C(R$^2$)=;

R$^2$ is selected from hydrogen, halogen, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$;

W is a phenyl ring or a 5 or 6-membered heteroaryl ring, either ring being optionally substituted with one or more substituents selected from halogen, cyano, oxo C$_{1-4}$-alkyl, halo-C$_{1-4}$-alkyl, cyano-C$_{1-4}$-alkyl, —OR$^5$, —NR$^{7A}$R$^{7B}$, —NR$^6$C(O)OR$^5$, —NR$^6$C(O)R$^5$, —NR$^6$C(O)NR$^{7A}$R$^{7B}$, —C(O)NR$^{7A}$R$^{7B}$, —C(O)R$^5$, —C(O)OR$^5$, —SO$_2$R$^5$, —SO$_2$NR$^{7A}$R$^{7B}$ and —NR$^6$S(O)$_2$R$^5$;

R$^{7A}$ and R$^{7B}$ are independently hydrogen, C$_{1-4}$-alkyl or halo-C$_{1-4}$-alkyl.

V is selected from a bond, —O—, —N(R$^6$)—, —(C=O)—, —CONR$^6$—, —NR$^6$C(O)—, or —C$_{1-4}$-alkylene-, wherein the C$_{1-4}$-alkylene group is optionally substituted by halogen, and wherein any one of the carbon atoms of the C$_{1-4}$-alkylene group may be replaced by —O— or —N(R$^6$)—;

R$^3$ is selected from hydrogen, —C$_{1-4}$-alkyl, —C$_{1-4}$-alkyl-C$_{1-4}$-alkoxy or a 3-7 membered heterocyclic ring or 3-7 membered cycloalkyl ring, or a 5 or 6-membered heteroaryl ring, any one of the rings being optionally substituted with one or more substituents selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$;

with the proviso that groups —WVR$^3$ and/or R$^1$ are not:

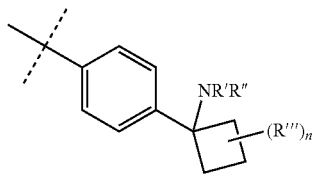

wherein n is 0, 1, or 2;

R' and R" are independently selected from the group consisting of H, —C$_1$-C$_6$alkyl, —(C=O)—C$_1$-C$_6$ alkyl and —(C=O)OC(CH$_3$)$_3$; and R''' is H, OH, or C$_1$-C$_6$ alkyl.

And according to a second aspect of the invention there is provided a compound of formula (I) or a pharmaceutically acceptable salt, or N-oxide thereof

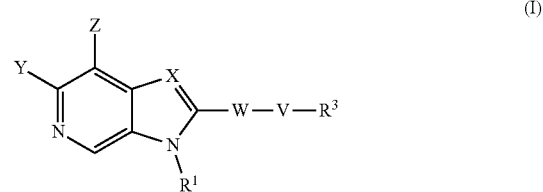

(I)

Wherein:

Y is selected from hydrogen, hydroxyl, —NH$_2$, —NH—C$_{1-4}$-alkyl, —NH-halo-C$_{1-4}$-alkyl, or —C$_{1-4}$-alkoxy;

Z is selected from hydrogen, halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, or —NHhalo-C$_{1-4}$-alkyl;

R$^1$ is a phenyl ring, or a 5 or 6-membered heteroaryl ring, either ring being optionally substituted with one or more substituents selected from halogen, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$; wherein R$^{4A}$, R$^{4B}$ R$^5$ and R$^6$ are each independently selected from hydrogen, C$_{1-4}$-alkyl or halo-C$_{1-4}$-alkyl, or R$^{4A}$ and R$^{4B}$ together with the nitrogen to which they are attached form a 3-7 membered cyclic amino group, optionally substituted by one or more substituents selected from: halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, —NHhalo-C$_{1-4}$-alkyl;

X is selected from —N= or —C(R$^2$)=;

R$^2$ is selected from hydrogen, halogen, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$;

W is a phenyl ring or a 5 or 6-membered heteroaryl ring, either ring being optionally substituted with one or more substituents selected from halogen, cyano, C$_{1-4}$-alkyl, halo-C$_{1-4}$-alkyl, cyano-C$_{1-4}$-alkyl, —OR$^5$, —NR$^{7A}$R$^{7B}$, —NR$^6$C(O)OR$^5$, —NR$^6$C(O)R$^5$, —NR$^6$C(O)NR$^{7A}$R$^{7B}$, —C(O)NR$^{7A}$R$^{7B}$, —C(O)R$^5$, —C(O)OR$^5$, —SO$_2$R$^5$, —SO$_2$NR$^{7A}$R$^{7B}$ and —NR$^6$S(O)$_2$R$^5$;

R$^{7A}$ and R$^{7B}$ are independently hydrogen, C$_{1-4}$-alkyl or halo-C$_{1-4}$-alkyl.

V is selected from a bond, —O—, —N(R$^6$)—, —(C=O)—, —CONR$^6$—, —NR$^6$C(O)—, or —C$_{1-4}$-alkylene-, wherein the C$_{1-4}$-alkylene group is optionally substituted by halogen, and wherein any one of the carbon atoms of the C$_{1-4}$-alkylene group may be replaced by —O— or —N(R$^6$)—;

R$^3$ is hydrogen or a 3-7 membered heterocyclic ring or 3-7 membered cycloalkyl ring selected from cyclopropyl, cyclopentyl or cyclohexyl, or a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$.

In addition to the surprising activity of the compounds of formula (I) at the SSAO receptor, it has been surprisingly found that the claimed compounds have surprisingly low activity at the hERG ion channel. The person skilled in the art, for example a medicinal chemist, understands that low hERG activity is an important property for a pharmaceutical drug compound. Without wishing to be bound by theory, it is believed that the —$WVR^3$ group as defined in claim 1 is especially advantageous in relation to reduced hERG activity.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in an amorphous form and/or several polymorphic forms and may be obtained in different crystal habits. Any reference herein, including the claims herein, to "compounds with which the invention is concerned" or "compounds of the invention" or "the present compounds", and the like, includes reference to the compounds irrespective of amorphous or polymorphic form.

Since compounds of the invention have a nitrogen atom in an aromatic ring they may form N-oxides, and the invention includes compounds of the invention in their N-oxide form.

Definitions

The following definitions shall apply throughout the specification and the appended claims, unless otherwise stated or indicated.

The term "$C_{1-4}$-alkyl" denotes a straight or branched alkyl group having from 1 to 4 carbon atoms. For parts of the range $C_{1-4}$-alkyl all subgroups thereof are contemplated such as $C_{1-3}$-alkyl, $C_{1-2}$-alkyl, $C_{2-4}$-alkyl, $C_{2-3}$-alkyl and $C_{3-4}$-alkyl. Examples of said $C_{1-4}$-alkyl include methyl, ethyl, n-propyl, isopropyl, n-butyl, isobutyl, sec-butyl and tert-butyl.

Unless otherwise specified, the term "$C_{3-7}$-cycloalkyl" refers to a monocyclic saturated or partially unsaturated hydrocarbon ring system having from 3 to 7 carbon atoms. Examples of said $C_{3-7}$-cycloalkyl include cyclopropyl, cyclobutyl, cyclopentyl, cyclohexyl, cyclohexenyl, cycloheptyl, and cycloheptenyl. For parts of the range "$C_{3-7}$-cycloalkyl" all subgroups thereof are contemplated such as $C_{3-7}$-cycloalkyl, $C_{3-6}$-cycloalkyl, $C_{3-5}$-cycloalkyl, $C_{3-4}$-cycloalkyl, $C_{4-7}$-cycloalkyl, $C_{4-6}$-cycloalkyl, $C_{4-5}$-cycloalkyl, $C_{5-7}$-cycloalkyl, $C_{5-6}$-cycloalkyl, and $C_{6-7}$-cycloalkyl.

The term "$C_{1-4}$-alkoxy" refers to a straight or branched $C_{1-4}$-alkyl group which is attached to the remainder of the molecule through an oxygen atom. For parts of the range $C_{1-4}$-alkoxy, all subgroups thereof are contemplated such as $C_{1-3}$-alkoxy, $C_{1-2}$-alkoxy, $C_{2-4}$-alkoxy, $C_{2-3}$-alkoxy and $C_{3-4}$-alkoxy. Examples of said $C_{1-4}$-alkoxy include methoxy, ethoxy, n-propoxy, isopropoxy, n-butoxy, isobutoxy, sec-butoxy and tert-butoxy.

The term "halo$C_{1-4}$-alkoxy" refers to a straight or branched $C_{1-4}$-alkyl group which is attached to the remainder of the molecule through an oxygen atom and has one or more hydrogen atoms thereof replaced with halogen such as fluoro or chloro. For parts of the range $C_{1-4}$-alkoxy, all subgroups thereof are contemplated. Examples of said $C_{1-4}$-alkoxy include trifluoromethoxy.

The term "hydroxy-$C_{1-4}$-alkyl" denotes a straight or branched $C_{1-4}$-alkyl group that has one or more hydrogen atoms thereof replaced with OH. Examples of said hydroxy-$C_{1-4}$-alkyl include hydroxymethyl, 2-hydroxyethyl and 2,3-dihydroxypropyl.

The term "halo-$C_{1-4}$-alkyl" denotes a straight or branched $C_{1-4}$-alkyl group that has one or more hydrogen atoms thereof replaced with halogen. Examples of said halo-$C_{1-4}$-alkyl include fluoromethyl, trifluoromethyl, trichloromethyl and 2-fluoroethyl.

The term "cyano-$C_{1-4}$-alkyl" denotes a straight or branched $C_{1-4}$-alkyl group that has one or more hydrogen atoms thereof replaced with cyano. Examples of said cyano-$C_{1-4}$-alkyl include cyanomethyl, 2-cyanoethyl and 3-cyanopropyl.

The term "amino-$C_{1-4}$-alkyl" denotes a straight or branched $C_{1-4}$-alkyl group substituted with an amino group. Examples of said amino-$C_{1-4}$-alkyl group include aminomethyl and 2-aminoethyl.

The term "$C_{1-4}$-alkylamino-$C_{1-4}$-alkyl" denotes an amino-$C_{1-4}$-alkyl group as defined above, wherein the amino group is substituted with a straight or branched $C_{1-4}$-alkyl group. Examples of said $C_{1-4}$-alkylamino-$C_{1-4}$-alkyl include methylaminoethyl and ethylaminopropyl.

The term "di($C_{1-4}$-alkyl)amino-$C_{1-4}$-alkyl" denotes an amino-$C_{1-4}$-alkyl group as defined above, wherein the amino group is disubstituted with straight or branched $C_{1-4}$-alkyl groups, which can be the same or different. Examples of said di($C_{1-4}$-alkyl)amino-$C_{1-4}$-alkyl include N,N-dimethylaminomethyl, N-ethyl-N-methylaminoethyl and N,N-diethylaminomethyl.

The terms "heteroaryl" and "heteroaromatic ring" denote a monocyclic heteroaromatic ring comprising 5 to 6 ring atoms in which one or more of the ring atoms are other than carbon, such as nitrogen, sulphur or oxygen. Examples of heteroaryl groups include furyl, pyrrolyl, thienyl, oxazolyl, isoxazolyl, imidazolyl, thiazolyl, isothiazolyl, pyridinyl, pyrimidinyl, tetrazolyl, pyrazolyl, pyridazinyl, pyrazinyl and thiadiazolyl.

The terms "heterocyclyl" and "heterocyclic ring" denote a non-aromatic, fully saturated or partially unsaturated, preferably fully saturated, monocyclic ring system having from 3 to 7 ring atoms, especially 5 or 6 ring atoms, in which one or more of the ring atoms are other than carbon, such as nitrogen, sulphur or oxygen. Examples of heterocyclic groups include piperidinyl, morpholinyl, homomorpholinyl, azepanyl, piperazinyl, oxo-piperazinyl, diazepinyl, tertahydropyridinyl, tetrahydropyranyl, pyrrolidinyl, tertahydrofuranyl, and dihydropyrrolyl, groups.

The term "heterocyclic-$C_{1-4}$-alkyl" refers to a heterocyclic ring that is directly linked to a straight or branched $C_{1-4}$-alkyl group via a carbon or nitrogen atom of said ring. Examples of said heterocyclic-$C_{1-4}$-alkyl include piperidin-4-ylmethyl, piperidin-1-ylmethyl, morpholin-4-ylmethyl and piperazin-4-ylmethyl. The $C_{1-4}$-alkyl part, which includes methylene, ethylene, propylene or butylene, is optionally substituted by one or more substituents selected from halogen, amino, methoxy, or hydroxyl.

The term "$C_{1-4}$-alkylene" denotes a straight or branched divalent saturated hydrocarbon chain having from 1 to 4 carbon atoms. The $C_{1-4}$-alkylene chain may be attached to the rest of the molecule and to the radical group through one carbon within the chain or through any two carbons within the chain. Examples of $C_{1-4}$-alkylene radicals include methylene [—$CH_2$—], 1,2-ethylene [—$CH_2$—$CH_2$—], 1,1-ethylene [—$CH(CH_3)$—], 1,2-propylene [—$CH_2$—CH($CH_3$)—] and 1,3-propylene [—$CH_2$—$CH_2$—$CH_2$—]. When referring to a "$C_{1-4}$-alkylene" radical, all subgroups thereof are contemplated, such as $C_{1-2}$-alkylene, $C_{2-3}$-alkylene, or $C_{3-4}$-alkylene.

"Halogen" refers to fluorine, chlorine, bromine or iodine, preferably fluorine and chlorine, most preferably fluorine.

"Hydroxy" refers to the —OH radical.

"Cyano" refers to the —CN radical.

"Oxo" refers to the carbonyl group =O.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., *The Organic Chemistry of Drug Design and Drug Action*, 2$^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Tautomers include enol and keto forms. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

The Group Y

In an embodiment Y is from hydrogen, hydroxyl, —$NH_2$, —NH—$C_{1-4}$-alkyl such as —NH-Methyl, —NH-ethyl, or —NH-isopropyl, —NH-halo-$C_{1-4}$-alkyl such as —NHtrifluoromethyl, or —$C_{1-4}$-alkoxy such as methoxy. In an embodiment Y is hydrogen.

The Group Z

In an embodiment Z is hydrogen, halogen such as fluoro or chloro, hydroxyl, cyano, $C_{1-4}$-alkyl such as methyl or isopropyl, halo-$C_{1-4}$-alkyl such as triflouromethyl, $C_{1-4}$-alkoxy such as methoxy, halo-$C_{1-4}$-alkoxy such as trifluoromethoxy, —$CONH_2$, —$SO_2NH_2$, —$NH_2$, —$NHC_{1-4}$-alkyl such as —NH-Methyl, —NH-ethyl, or —NH-isopropyl, or —NHhalo-$C_{1-4}$-alkyl. In an embodiment Z is hydrogen.

The Group $R^1$

In an $R^1$ embodiment is a phenyl ring, or a 5 or 6-membered heteroaryl ring either ring being optionally substituted with one or more substituents selected from halogen such as fluoro or chloro, cyano, $C_{1-4}$-alkyl such as methyl or isopropyl, halo-$C_{1-4}$-alkyl such as trifluoromethyl, cyano-$C_{1-4}$-alkyl such as methylcyano, —$OR^5$ such as methoxy or trifluoromethoxy, —$NR^{4A}R^{4B}$ such as —$NH_2$, —NHMethyl, —NHisopropyl, —$NR^6C(O)OR^5$, —$NR^6C(O)R^5$, —$NR^6C(O)NR^{4A}R^{4B}$, —$C(O)NR^{4A}R^{4B}$, —$C(O)R^5$ such as —$COCH_3$, —$C(O)OR^5$, and —$NR^6S(O)_2R^5$. In an embodiment $R^1$ is optionally substituted phenyl, pyridyl, pyrrole, furan, imidazole, or thiophene.

In an embodiment $R^1$ is a phenyl ring, or a 5 or 6-membered heteroaryl ring substituted with a 3-7 membered cycloalkyl group such as cyclopropyl, cyclobutyl, cyclopentyl, cyclohexyl; preferably cyclopropyl.

$R^{4A}$, $R^{4B}$ $R^5$ and $R^6$ are each independently selected from hydrogen, $C_{1-4}$-alkyl such as methyl, ethyl or isopropyl, or halo-$C_{1-4}$-alkyl such as trifluoromethyl, or $R^{4A}$ and $R^{4B}$ together with the nitrogen to which they are attached form a 3-7 membered cyclic amino group such as aziridine, azetidine, oxetane, pyrrolidine, piperidine, piperazine, homopiperidine, homopiperazine, morpholine, or tetrahydrofuran, optionally substituted by one or more substituents selected from: halogen such as fluoro or chloro, hydroxyl, cyano, $C_{1-4}$-alkyl such as methyl or isopropyl, halo-$C_{1-4}$-alkyl such as triflouromethyl, $C_{1-4}$-alkoxy such as methoxy, halo-$C_{1-4}$-alkoxy such as trifluoromethoxy, —$CONH_2$, —$SO_2NH_2$, —$NH_2$, —$NHC_{1-4}$-alkyl, —NHhalo-$C_{1-4}$-alkyl;

The Group X

In an embodiment X is selected from —N= or —C($R^2$)=;

The Group $R^2$

In an embodiment $R^2$ is hydrogen, halogen such as fluoro or chloro, cyano, $C_{1-4}$-alkyl such as methyl or ethyl or isopropyl, halo-$C_{1-4}$-alkyl such as trifluoromethyl. In an embodiment $R^2$ is hydrogen.

The Group W

In an embodiment W is a phenyl ring. In an alternative embodiment W a 6-membered heterocyclic ring selected from pyridine, pyridazine, pyrazine, or pyrimidine. In an alternative embodiment W is a 5-membered ring selected from oxazole, thiazole or imidazole. In an embodiment W is imidazolyl and the imidazolyl ring is connected to the pyrrolopyridine core (i.e. the rest of the molecule) via an imidazolyl ring carbon atom. In an embodiment W is a pyrazole ring.

Any of the aforementioned rings are optionally substituted with one or more substituents as defined in claim 1. In an embodiment W is substituted with one or more groups selected from fluoro, chloro, cyano, methyl or trifluoromethyl.

In an embodiment W is a divalent group selected from any one of the following rings, any of which rings is optionally substituted with one or more substituents as defined in relation to formula (I).

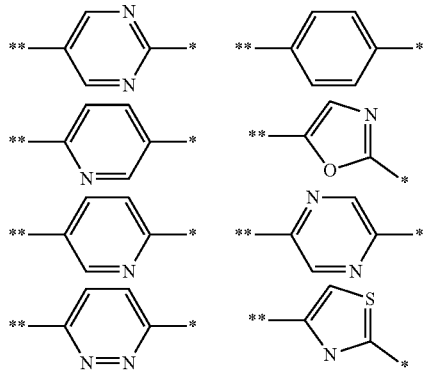

wherein the bond marked ** is directly connected to the rest of the molecule and the atom marked * is directly connected to V.

The Group V

In an embodiment V is selected from a bond, —O—, —N($R^6$)— such as —NH— or —N($CH_3$)—, —(C=O)—, —$CONR^6$— such as —CONH— or —CON($CH_3$)—, —$NR^6C(O)$— such as —NHC(O)— or —N($CH_3$)C(O)—, or —$C_{1-4}$-alkylene-, wherein the $C_{1-4}$-alkylene group is optionally substituted by halogen such as fluoro or chloro, and wherein any one of the carbon atoms of the $C_{1-4}$-alkylene group may be replaced by —O— or —N($R^6$)— such as —$CH_2$O— in either direction or —$CH_2$—NH—; —$CH_2$—N($CH_3$)— in either direction.

The Group $R^3$

In an embodiment $R^3$ is hydrogen. In an alternative embodiment $R^3$ an optionally substituted 3-7 membered heterocyclic ring such as aziridine, azetidine, oxetane, pyrrolidine, piperidine, piperazine, homopiperidine, homopiperazine, morpholine, or tetrahydrofuran. In an embodiment $R^3$ is an optionally substituted 3-7 membered cycloalkyl ring such as cyclopropyl, cyclobutyl, cyclopentyl or cyclohexyl. In an alternative embodiment $R^3$ is an optionally substituted 5 or 6-membered heteroaryl ring such as imidazole, phenyl, pyridine, thophene. The optional substituents are defined in formula (I). In an embodiment any one of the rings is optionally substituted with one or more substituents selected from halogen such as fluoro or chloro, oxo, hydroxyl, cyano, $C_{1-4}$-alkyl such as methyl, ethyl, propyl, t-butyl, or isopropyl, halo-$C_{1-4}$-alkyl such as trifluoromethyl, cyano-$C_{1-4}$-alkyl, —$OR^5$ such as methocy or trifluoromethoxy, —$NR^{4A}R^{4B}$ such as —$NH_2$, NHmethyl, or morpholine or piperidine, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$.

In an embodiment $R^3$ is selected from the following ring systems:

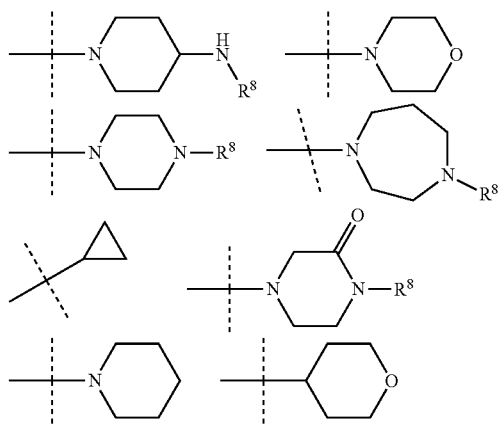

Wherein $R^8$ is selected from hydrogen, $CH_3$, —$CONH_2$, —$NHCONH_2$, —$S(O)_2CH_3$, —$COCH_3$.

In an embodiment $R^3$ is selected from the following ring systems:

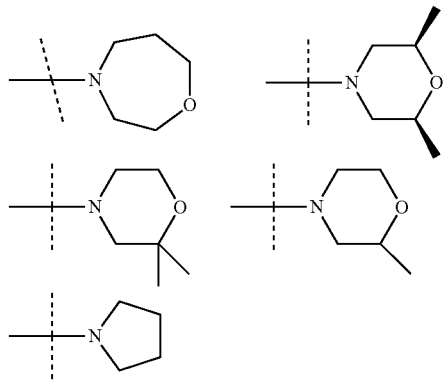

In an embodiment $R^3$ is selected from hydrogen, —$C_{1-4}$-alkyl such as methyl, ethyl, propyl and isopropyl, and —$C_{1-4}$-alkyl-$C_{1-4}$-alkoxy such as —$(CH_2)_2OCH_3$.

In an embodiment the group —VR³ is selected from:

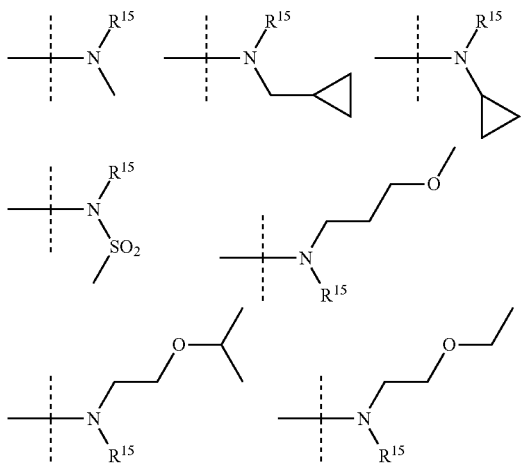

wherein R¹⁵ is hydrogen or methyl.

In an embodiment, the invention includes a compound of formula (Xa)

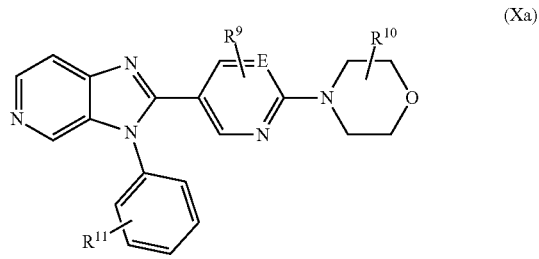

(Xa)

wherein E is —C= or —N=,
R⁹ and R¹⁰ are each independently one or more substituents selected from hydrogen, halogen, cyano, oxo, $C_{1-4}$-alkyl such as methyl, —$OC_{1-4}$-alkyl such as $OCH_3$, and halo-$C_{1-4}$-alkyl; and
R¹¹ is one or more substituents selected from hydrogen, halogen such as fluoro and/or chloro, cyano, cyclopropyl, $C_{1-4}$-alkyl such as methyl, and halo-$C_{1-4}$-alkyl.

In one aspect, the invention relates to a compound of formula (I) for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders, cystic fibrosis, or inhibition of tumour growth; and they are useful in the manufacture of a medicament for treatment or prevention of inflammation, inflammatory diseases, immune or autoimmune disorders, cystic fibrosis, or inhibition of tumour growth In particular, it is believed that compounds of formula (I) are useful for the treatment or prevention of arthritis (such as rheumatoid arthritis, juvenile rheumatoid arthritis, osteoarthritis and psoriatic arthritis), synovitis, vasculitis, conditions associated with inflammation of the bowel (such as Crohn's disease, ulcerative colitis, inflammatory bowel disease and irritable bowel syndrome), atherosclerosis, multiple sclerosis, Alzheimer's disease, vascular dementia, pulmonary inflammatory diseases (such as asthma, chronic obstructive pulmonary disease and acute respiratory distress syndrome), fibrotic diseases (including idiopathic pulmonary fibrosis, cardiac fibrosis and systemic sclerosis (scleroderma)), inflammatory diseases of the skin (such as contact dermatitis, atopic dermatitis and psoriasis), systemic inflammatory response syndrome, sepsis, inflammatory and/or autoimmune conditions of the liver (such as autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, ischemic diseases (such as stroke and ischemia-reperfusion injury), and myocardial infarction and/or the complications thereof, or epilepsy.

It is believed that the compounds of the invention are especially useful for the treatment or prevention of vasculitis, including, but not limited to, giant cell arteritis, Takayasu's arteritis, Polyarteritis nodosa, Kawasaki disease, Wegener's granulomatosis, Churg-Strauss syndrome, microscopic polyangiitis, Henoch-Schönlein purpura, cryoglobulinemia, cutaneous leukocytoclastic angiitis and primary angiitis of the central nervous system.

It is also believed that the compounds of the invention are especially useful for the treatment of rheumatoid arthritis, chronic obstructive pulmonary disease or atopic dermatitis.

In view of the evidence cited in the above introduction that VAP-1 is up regulated in several cancers, including gastric cancer, melanoma, hepatoma and head and neck tumours and that mice bearing enzymatically inactive VAP-1 grow melanomas more slowly, and in view of the link between VAP-1 and angiogenesis, it is also expected that the compounds of the invention are anti-angiogenic and therefore have utility in the treatment of cancers by inhibition of tumour growth.

The invention thus includes the compounds of formula (I) above for use in the treatment or prevention of the above-mentioned conditions and diseases. The invention also includes the use of said compounds in the manufacture of a medicament for the treatment or prevention of the above-mentioned conditions and diseases. The invention furthermore includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

Compositions

A currently preferred embodiment of the invention is a pharmaceutical composition comprising a compound of formula (I), together with one or more pharmaceutically acceptable carriers and/or excipients.

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of formula (I) above may be prepared by, or in analogy with, conventional methods. The preparation of intermediates and compounds according to the examples of the present invention may in particular be illuminated by the following Schemes. Definitions of variables in the structures in schemes herein are commensurate with those of corresponding positions in the formulas delineated herein.

Scheme 1. General synthetic routes for preparation of compounds of formula (I) wherein X is N (i.e. compounds of general formula (Ia))

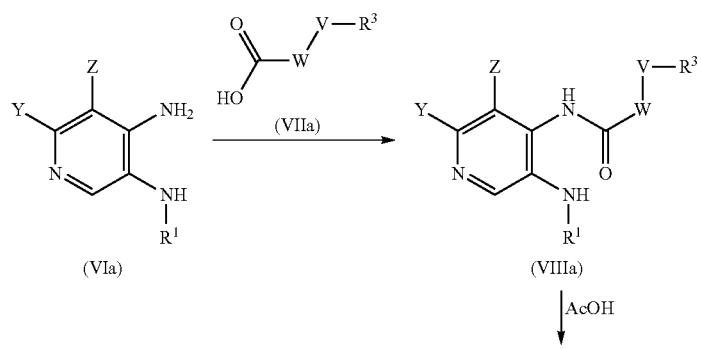

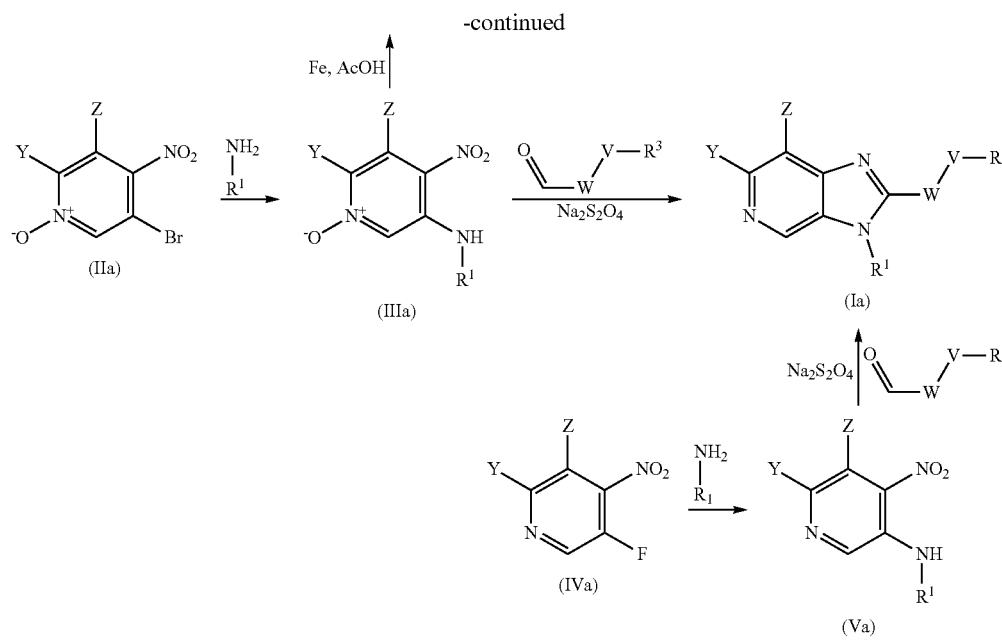

wherein V, W, X, Y, Z, $R^1$, $R^2$ and $R^3$ are as defined in formula (I);

Compounds of general formula (I) where X is N (designated compounds of general formula (Ia)), can easily be prepared by a number of alternative routes. For example, 3-bromo-4-nitropyridine N-oxides of general formula (IIa) can undergo SnAr displacement with $R^1NH_2$ amines to give compounds of general formula (IIIa), which can in turn be reductively cyclised to give compounds of general formula (Ia). Alternatively, 3-fluoro-4-nitropyridines of general formula (IVa) can undergo SnAr displacement with $R^1NH_2$ amines to give compounds of general formula (Va), which can in turn be reductively cyclised to give compounds of general formula (Ia). Alternatively, compounds of general formula (IIIa) can be reduced to pyridine-3,4-diamines of general formula (VIa). Compounds of general formula (VIa) can then undergo amide formation with carboxylic acids of general formula (VIIa) to give amides of general formula (VIIIa) which can be cyclised to give compounds of general formula (Ia).

Optionally, the group W—V—$R^3$ can be built up sequentially using standard chemistry methodologies including amide, urea and sulphonamide formation. If required, standard protecting group strategies can be employed to facilitate the synthesis.

Optionally, a compound of formula (Ia) can also be transformed into another compound of formula (Ia) in one or more synthetic steps.

Scheme 2. General synthetic routes for preparation of compounds of formula (I) wherein X is $CR^2$ (i.e. compounds of general formula (Ib))

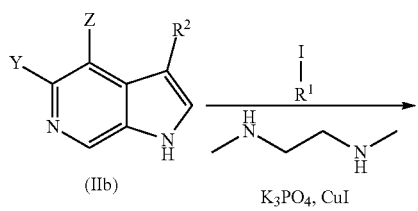

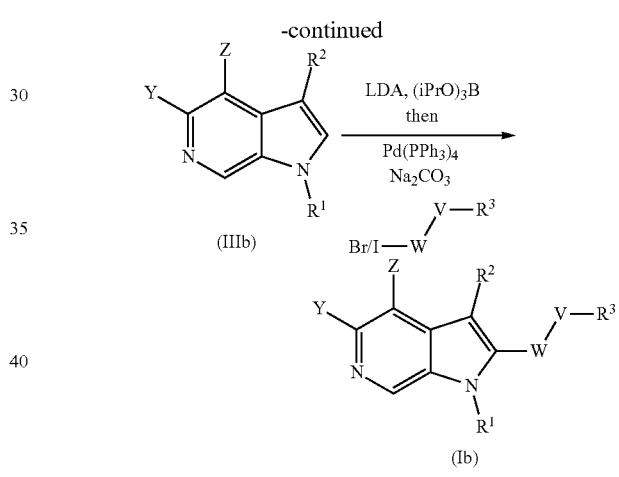

wherein V, W, X, Y, Z, $R^1$, $R^2$ and $R^3$ are as defined in formula (I);

Compounds of general formula (I) where X is $CR^2$ (designated compounds of general formula (Ib)), can easily be prepared standard means. For example, 6-azaindoles of general formula (IIb) can be N-arylated with $R^1$—I iodides to give compounds of general formula (IIIb) which can in turn be converted to compounds of general formula (Ib) by boronate formation and subsequent Suzuki coupling.

Optionally, the group W—V—$R^3$ can be built up sequentially using standard chemistry methodologies including amide, urea and sulphonamide formation. If required, standard protecting group strategies can be employed to facilitate the synthesis.

Optionally, a compound of formula (Ib) can also be transformed into another compound of formula (Ib) in one or more synthetic steps.

The following abbreviations have been used:
Ac acetyl
aq aqueous
Boc tertiary-butyloxycarbonyl calcd calculated
d day(s)
DCM dichloromethane
DIPEA diisopropylethylamine
DMA dimethylacetamide
DMF dimethylformamide
DMSO Dimethyl sulfoxide
EDC N-(3-dimethylaminopropyl)-N-ethylcarbodiimide
ES+ electrospray ionization
Et₃N triethylamine
EtOAc ethyl acetate
EtOH ethanol
Ex Example
h hour(s)
HATU O-(7-azabenzotriazol-1-yl)-N,N,N',N'-tetramethyluronium hexafluorophosphate
HBTU O-benzotriazole-N,N,N',N'-tetramethyl-uronium-hexafluoro phosphate
HPLC High Performance Liquid Chromatography
Int Intermediate
LCMS Liquid Chromatography Mass Spectrometry
LDA Lithium diisopropylamide
M molar
MeCN acetonitrile
MeOH methanol
[MH]+ protonated molecular ion
Min minute(s)
NMP 1-methyl-2-pyrrolidinone
QTOF Quadrupole time-of-flight mass spectrometer
RP reverse phase
RT room temperature
Rt retention time
sat saturated
TFA trifluoroacetic acid
THF Tetrahydrofuran
UV Ultra violet
XPhos 2-dicyclohexylphosphino-2',4',6'-triisopropylbiphenyl

EXAMPLES AND INTERMEDIATE COMPOUNDS

Experimental Methods

Reactions were conducted at room temperature unless otherwise specified. Microwave reactions were performed with a Biotage microwave reactor using process vials fitted with aluminium caps and septa. Preparative chromatography was performed using a Flash Master Personal system equipped with Isolute Flash II silica columns or using a CombiFlash Companion system equipped with GraceResolv silica column. Reverse Phase HPLC was performed on a Gilson system with a UV detector equipped with Phenomenex Synergi Hydro RP 150×10 mm, or YMC ODS-A 100/150×20 mm columns. The purest fractions were collected, concentrated and dried under vacuum. Compounds were typically dried in a vacuum oven at 40° C. prior to purity analysis. Compound analysis was performed by HPLC/LCMS using an Agilent 1100 HPLC system/Waters ZQ mass spectrometer connected to an Agilent 1100 HPLC system with a Phenomenex Synergi, RP-Hydro column (150×4.6 mm, 4 um, 1.5 mL per min, 30° C., gradient 5-10 0% MeCN (+0.085% TFA) in water (+0.1% TFA) over 7 min, 200-300 nm). Accurate masses were measured using a Waters QTOF electrospray ion source and corrected using Leucine Enkephalin lockmass. Spectra were acquired in positive and negative electrospray mode. The acquired mass range was m/z 100-1000. Test compounds were dissolved in DMSO to give a 10 mM stock solution. Typically 5 mL of the DMSO stock were diluted with 495 mL of acetonitrile and then further diluted with acetonitrile and water (1:1) to give a final concentration of 0.2 mM. The mass values reported correspond either to the parent molecule with a hydrogen added [MH] or with a hydrogen subtracted [M-H]. The compounds prepared were named using IUPAC nomenclature.

Intermediate 1

3-[(4-Chlorophenyl)amino]-4-nitropyridin-1-ium-1-olate

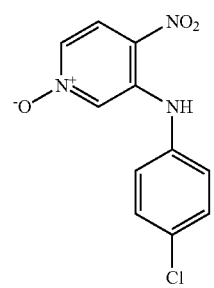

3-Bromo-4-nitropyridine N-oxide (1.00 g, 4.57 mmol) and 4-chloroaniline (1.75 g, 13.7 mmol) were dissolved in EtOH and heated at 60° C. for 18 h. The reaction mixture was cooled to 0° C. and the precipitate was collected by filtration and washed with cold EtOH to give the title compound as an orange solid (317 mg, 26.1%). LCMS (ES+): 266.1 [MH]+. HPLC: Rt 5.44 min, 99.5% purity.

Intermediates 2-3

Intermediates 2-3 were prepared similarly to Intermediate 1, by coupling of 3-bromo-4-nitropyridine N-oxide with the appropriate aniline; see Table 1 below.

TABLE 1

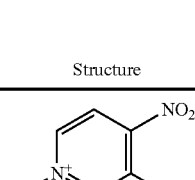

SnAr formation of anilines

| Int | Structure | Name | Form, Yield, LCMS, HPLC |
|---|---|---|---|
| 2 | 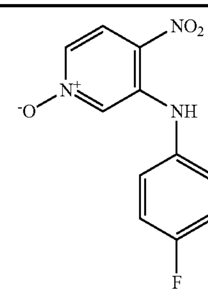 | 3-[(4-Fluorophenyl)amino]-4-nitropyridin-1-ium-1-olate | Orange solid Yield 2.66 g, 46.7% LCMS (ES+): 250.1 [MH]+ HPLC: Rt 5.00 min, 97.3% purity |

TABLE 1-continued

SnAr formation of anilines

| Int | Structure | Name | Form, Yield, LCMS, HPLC |
|---|---|---|---|
| 3 | 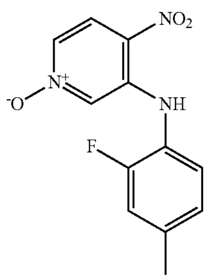 | 3-[(2-Fluoro-4-methylphenyl)amino]-4-nitropyridin-1-ium-1-olate | Orange solid Yield 200 mg, 5.55% LCMS (ES+): 264.0 [MH]+ HPLC: Rt 5.52 min, 93.2% purity |

Intermediate 4

3-[(4-Fluoro-2-methylphenyl)amino]-4-nitropyridin-1-ium-1-olate

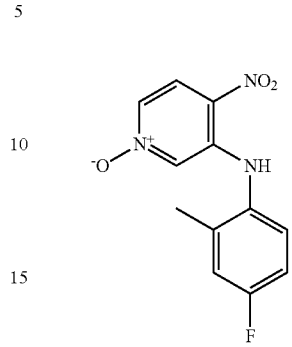

3-Fluoro-4-nitropyridine N-oxide (1.00 g, 6.33 mmol) and 4-fluoro-2-methylaniline (2.42 mL, 25.3 mmol) were dissolved in EtOH (12 mL) and heated at 90° C. for 16 h. The reaction mixture was cooled to RT, the precipitate was collected by filtration and washed with cold EtOH (10 mL) to give the title compound (1.60 g, 96.2%) as a yellow solid. LCMS (ES+): 264.1 [MH]+. HPLC: Rt 5.56 min, 95.9% purity.

Intermediates 5-12

Intermediates 5-12 were prepared similarly to Intermediate 4, by coupling of 3-fluoro-4-nitropyridine N-oxide with the appropriate aniline; see Table 2 below.

TABLE 2

SnAr formation of anilines

| Int | Structure | Name | Form, Yield, LCMS, HPLC |
|---|---|---|---|
| 5 | 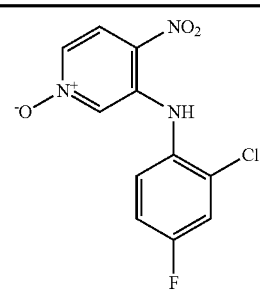 | 3-[(2-Chloro-4-fluorophenyl)amino]-4-nitropyridin-1-ium-1-olate | Yellow solid Yield 1.93 g, 53.9% LCMS (ES+): 284.2 [MH]+ HPLC: Rt 5.67 min, 96.0% purity |
| 6 | 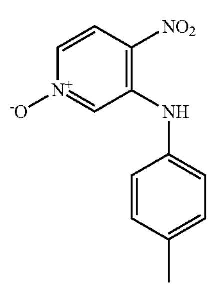 | 3-[(4-Methylphenyl)amino]-4-nitropyridin-1-ium-1-olate | Orange solid Yield 1.12 g, 96.2% LCMS (ES+): 246.1 [MH]+ HPLC: Rt 5.65 min, 99.3% purity |

TABLE 2-continued

SnAr formation of anilines

| Int | Structure | Name | Form, Yield, LCMS, HPLC |
|---|---|---|---|
| 7 | 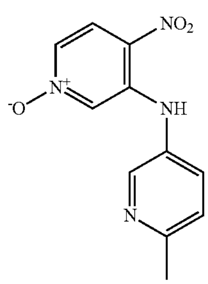 | 3-[(6-Methylpyridin-3-yl)amino]-4-nitropyridin-1-ium-1-olate | Orange solid<br>Yield 1.04 g, 89.0%<br>LCMS (ES+): 247.0 [MH]+<br>HPLC: Rt 2.86 min, 64.5% purity |
| 8 | 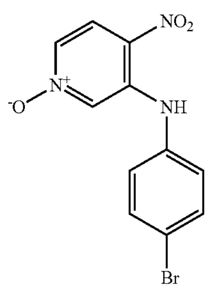 | 3-[(4-Bromophenyl)amino]-4-nitropyridin-1-ium-1-olate | Orange solid<br>Yield 1.55 g, crude<br>LCMS (ES+): 309.9 [MH]+<br>HPLC: Rt 5.66 min, 95.8% purity |
| 9 | 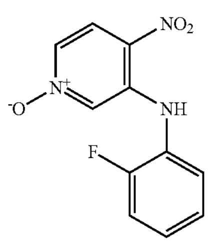 | 3-[(2-Fluorophenyl)amino]-4-nitropyridin-1-ium-1-olate | Orange solid<br>Yield 1.08 g, 91.3%<br>LCMS (ES+): 250.0 [MH]+<br>HPLC: Rt 5.14 min, 100% purity |
| 10 | 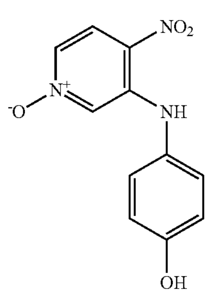 | 3-[(4-Hydroxyphenyl)amino]-4-nitropyridin-1-ium-1-olate | Dark orange solid<br>Yield 1.40 g, crude<br>LCMS (ES+): 248.0 [MH]+<br>HPLC: Rt 4.25 min, 96.8% purity |

TABLE 2-continued

SnAr formation of anilines

| Int | Structure | Name | Form, Yield, LCMS, HPLC |
|---|---|---|---|
| 11 | 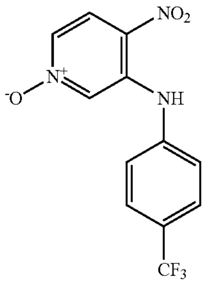 | 4-Nitro-3-{[4-(trifluoromethyl)phenyl]amino}pyridin-1-ium-1-olate | Orange solid Yield 1.38 g, 97.3% LCMS (ES$^+$): 300.0 [MH]$^+$ HPLC: Rt 5.84 min, 93.8% purity |
| 12 | 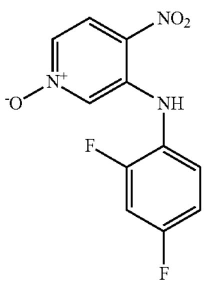 | 3-[(2,4-Difluorophenyl)amino]-4-nitropyridin-1-ium-1-olate | Yellow solid Yield 2.16 g, 63.9% LCMS (ES$^+$): 268.0 [MH]$^+$ HPLC: Rt 5.14 min, 99.3% purity |

Intermediate 13

N-(4-Chloro-3-fluorophenyl)-4-nitropyridin-3-amine

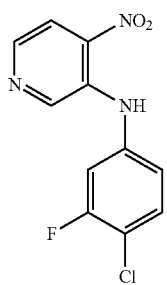 [SMILES: O=[N+]([O-])c1ccncc1Nc1ccc(Cl)c(F)c1]

NaH (422 mg, 60% dispersion in mineral oil, 10.6 mmol) was suspended in THF (20 mL) and 4-chloro-3-fluoroaniline (1.54 g, 10.6 mmol) and 3-fluoro-4-nitropyridine (500 mg, 3.52 mmol) were added. The reaction mixture was stirred for 18 h, quenched with sat. aq. NH$_4$Cl (2 mL), and concentrated in vacuo. The residue was partitioned between water (50 mL) and DCM (50 mL) and the organic fraction was dried (MgSO$_4$) and concentrated in vacuo. The residue was purified by column chromatography to give the title compound (207 mg, 22.0%) as an orange solid. LCMS (ES$^+$): 268.0 [MH]$^+$.

Intermediates 14-18

Intermediates 14-18 were prepared similarly to Intermediate 13, by coupling of 3-fluoro-4-nitropyridine with the appropriate aniline; see Table 3 below.

TABLE 3

SnAr formation of anilines

| Int | Structure | Name | Form, Yield, LCMS, HPLC |
|---|---|---|---|
| 14 | 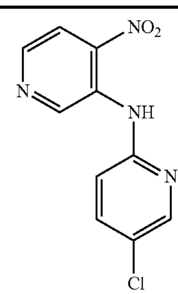 | N-(5-Chloropyridin-2-yl)-4-nitropyridin-3-amine | Orange gum Yield 221 mg, 25.1% LCMS (ES$^+$): 251.1 [MH]$^+$ HPLC: Rt 5.99 min, 93.6% purity |

TABLE 3-continued

SnAr formation of anilines

| Int | Structure | Name | Form, Yield, LCMS, HPLC |
|---|---|---|---|
| 15 | | 5-Fluoro-N-(4-nitropyridin-3-yl)pyridin-2-amine | Orange solid Yield 441 mg, 53.5% LCMS (ES+): 235.0 [MH]+ HPLC: Rt 5.40 min, 95.2% purity |
| 16 | | N-(4-Chloro-2-fluorophenyl)-4-nitropyridin-3-amine | Orange solid Yield 1.26 g, 66.9% LCMS (ES+): 268.1 [MH]+ |
| 17 | | N-(2,4-Difluorophenyl)-4-nitropyridin-3-amine | Orange solid Yield 752 mg, 42.5% LCMS (ES+): 252.0 [MH]+ HPLC: Rt 5.91 min, 77.8% purity |
| 18 | | 5-Methyl-N-(4-nitropyridin-3-yl)pyridin-2-amine | Dark red solid Yield 611 mg, 37.7% LCMS (ES+): 231.1 [MH]+ HPLC: Rt 4.61 min, 97.5% purity |

Intermediate 19

3-N-(4-Chlorophenyl)pyridine-3,4-diamine

Intermediate 1 (317 mg, 1.19 mmol) was dissolved in AcOH (10 mL) and iron powder (333 mg, 5.97 mmol) was added. The reaction mixture was heated at reflux for 1 h, diluted with water (50 mL), basified with $Na_2CO_3$ and extracted into DCM (3×50 mL). The combined organic fractions were dried ($MgSO_4$) and concentrated in vacuo to give the title compound as a red gum (254 mg, 96.9%). LCMS (ES+): 220.2 [MH]+. HPLC: Rt 4.31 min, 99.5% purity.

Intermediate 20

3-N-(4-Fluorophenyl)pyridine-3,4-diamine

Intermediate 20 was prepared similarly to Intermediate 19, using Intermediate 2 instead of Intermediate 1, to give the title compound (6.33 g, 91.3%) as a brown solid. LCMS (ES+): 204.1 [MH]+.

Intermediate 21

3-N-(4-Methylphenyl)pyridine-3,4-diamine

Intermediate 6 (6.00 g, 24.5 mmol) and ammonium formate (12.3 g, 196 mmol) were suspended in EtOH (200 mL), Raney Nickel (50% slurry in water; 11.0 mL) was added and the reaction mixture was heated at 85° C. for 2 h, filtered through Celite and concentrated in vacuo. The residue was partitioned between water (150 mL) and DCM/MeOH (150 mL/20 mL) and the aqueous fraction was extracted with DCM (100 mL). The combined organic fractions were dried (MgSO$_4$) and concentrated in vacuo to give the title compound (3.20 g, 65.6%) as a blue solid. LCMS (ES$^+$): 200.1 [MH]$^+$.

Intermediate 22

3-N-(4-Chloro-2-fluorophenyl)pyridine-3,4-diamine

Intermediate 22 was prepared similarly to Intermediate 21, using Intermediate 16 instead of Intermediate 6, to give the title compound (509 mg, 31.7%) as an orange solid. LCMS (ES$^+$): 238.1 [MH]$^+$.

Intermediate 23

3-N-(6-Methylpyridin-3-yl)pyridine-3,4-diamine

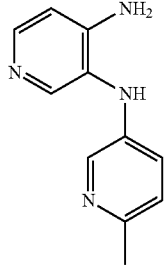

Intermediate 7 (1.40 g, 5.69 mmol) and hydrazine monohydrate (1.11 mL, 22.8 mmol) were suspended in THF (20 mL) and EtOH (20 mL), Raney nickel (50% slurry in water; 2 mL) was added slowly at 0° C. and the reaction mixture was warmed to RT and stirred for 2 h. The mixture was filtered through Celite washing with MeOH (80 mL) and the combined filtrate was concentrated in vacuo. The residue was purified by column chromatography to give the title compound (836 mg, 73.4%) as an off white solid. LCMS (ES$^+$): 201.1 [MH]$^+$.

Intermediate 24

3-N-(5-Methylpyridin-2-yl)pyridine-3,4-diamine

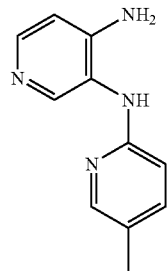

Intermediate 24 was prepared similarly to Intermediate 23, using Intermediate 18 instead of Intermediate 7, to give the title compound (741 mg, 70.1%) as a pale purple solid. LCMS (ES$^+$): 201.1 [MH]$^+$. HPLC: Rt 2.39 min, 98.5% purity.

Intermediate 25

3-N-(2,4-Difluorophenyl)pyridine-3,4-diamine

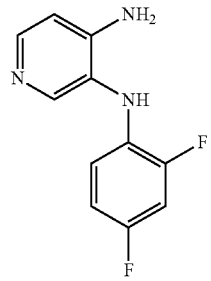 [SMILES: Nc1ccncc1Nc1ccc(F)cc1F]

Intermediate 25 was prepared similarly to Intermediate 23, using Intermediate 12 instead of Intermediate 7, to give the title compound (1.32 g, 73.6%) as a pink solid. LCMS (ES$^+$): 222.0 [MH]$^+$. HPLC: Rt 4.08 min, 99.2% purity.

Intermediate 26

Methyl 6-[(morpholin-4-yl)carbonyl]pyridine-3-carboxylate

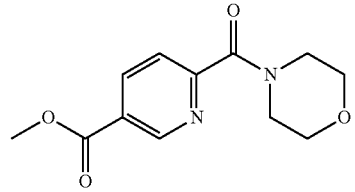 [SMILES: COC(=O)c1ccc(C(=O)N2CCOCC2)nc1]

5-(Methoxycarbonyl)pyridine-2-carboxylic acid (758 mg, 4.18 mmol) was dissolved in DMF (25 mL) and morpholine (603 uL, 5.23 mmol), Et$_3$N (2.45 mL, 16.7 mmol) and HBTU (1.67 g, 4.39 mmol) were added. The reaction mixture was stirred for 16 h and concentrated in vacuo. The residue was dissolved in EtOAc (100 mL), washed with sat. aq. Na$_2$CO$_3$ (100 mL), dried (MgSO$_4$) and concentrated in vacuo. The residue was purified by column chromatography to give the title compound (914 mg, 87.3%) as a yellow oil. LCMS (ES$^+$): 251.2 [MH]$^+$.

Intermediate 27

Methyl 6-(cyclopropylcarbamoyl)pyridine-3-carboxylate

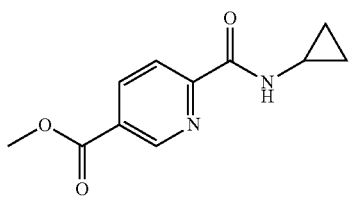 [SMILES: COC(=O)c1ccc(C(=O)NC2CC2)nc1]

Intermediate 27 was prepared similarly to Intermediate 26, using cyclopropylamine instead of morpholine, to give the title compound (774 mg, 42.4%) as a white solid. LCMS (ES$^+$): 221.2 [MH]$^+$.

Intermediate 28

Methyl 5-[(oxan-4-yl)amino]pyrazine-2-carboxylate

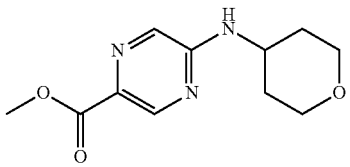 [SMILES: COC(=O)c1cnc(NC2CCOCC2)cn1]

Methyl 5-chloro-2-pyrazinecarboxylate (507 mg, 2.94 mmol), Et$_3$N (1.08 mL, 7.64 mmol) and 4-aminotetrahydropyran (395 uL, 3.82 mmol) were dissolved in dioxane (5 mL) and heated in a microwave reactor at 100° C. for 20 min. Water (50 mL) and brine (25 mL) were added and the reaction mixture was extracted into EtOAc (2×100 mL), dried (MgSO$_4$) and concentrated in vacuo to give the title compound (236 mg, 33.9%) as a yellow oil. LCMS (ES$^+$): 238.2 [MH]$^+$.

Intermediates 29-35

Intermediates 29-35 were prepared similarly to Intermediate 28, by coupling of with the appropriate aromatic ester with the appropriate amine; see Table 4 below.

TABLE 4

Coupling of with the appropriate aromatic ester with the appropriate amine

| Int | Structure | Name | Form, Yield, LCMS, HPLC |
|---|---|---|---|
| 29 | 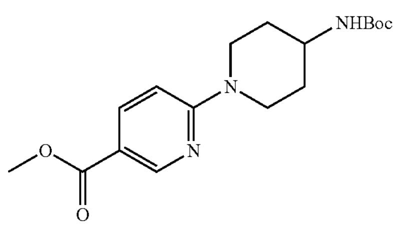 [SMILES: COC(=O)c1ccc(N2CCC(NC(=O)OC(C)(C)C)CC2)nc1] | Methyl 6-(4-{[(tert-butoxy)carbonyl]amino}piperidin-1-yl)pyridine-3-carboxylate | Off white solid Yield 1.66 g, 84.9% LCMS (ES$^+$): 336.1 [MH]$^+$ HPLC: Rt 4.73 min, 98.2% purity. |
| 30 | 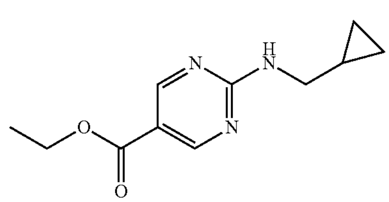 [SMILES: CCOC(=O)c1cnc(NCC2CC2)nc1] | Ethyl 2-[(cyclopropylmethyl)amino]pyrimidine-5-carboxylate | Yellow solid Yield 566 mg, 95.5% LCMS (ES$^+$): 222.1 [MH]$^+$ HPLC: Rt 5.79 min, 92.9% purity. |
| 31 | 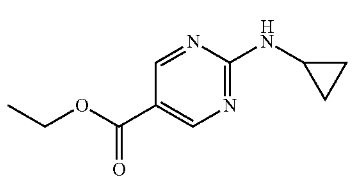 | Ethyl 2-(cyclopropylamino)pyrimidine-5-carboxylate | White solid Yield 526 mg, 94.7% LCMS (ES$^+$): 208.1 [MH]$^+$ HPLC: Rt 4.86 min, 93.7% purity. |

TABLE 4-continued

Coupling of with the appropriate aromatic ester with the appropriate amine

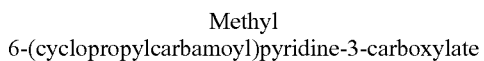

| Int | Structure | Name | Form, Yield, LCMS, HPLC |
|---|---|---|---|
| 32 | 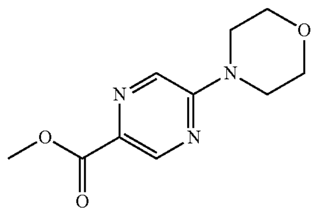 [SMILES: COC(=O)c1cnc(N2CCOCC2)cn1] | Methyl 5-(morpholin-4-yl)pyrazine-2-carboxylate | Pale yellow solid<br>Yield 628 mg, 95.8%<br>LCMS (ES$^+$): 224.2 [MH]$^+$ |
| 33 | 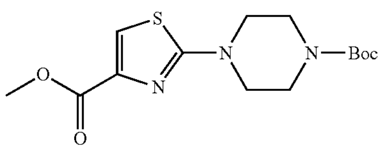 [SMILES: COC(=O)c1csc(N2CCN(C(=O)OC(C)(C)C)CC2)n1] | tert-Butyl 4-[4-(methoxycarbonyl)-1,3-thiazol-2-yl]piperazine-1-carboxylate | White solid<br>Yield 324 mg, 35.1%<br>LCMS (ES$^+$): 350.1 [MNa]$^+$. HPLC: Rt 6.04 min, 100% purity. |
| 34 | 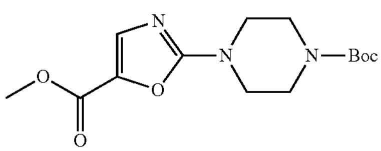 [SMILES: COC(=O)c1cnc(N2CCN(C(=O)OC(C)(C)C)CC2)o1] | tert-Butyl 4-[5-(methoxycarbonyl)-1,3-oxazol-2-yl]piperazine-1-carboxylate | Pale yellow solid<br>Yield 406 mg, 42.1%<br>LCMS (ES$^+$): 334.2 [MNa]$^+$. HPLC: Rt 5.81 min, 97.1% purity. |
| 35 | 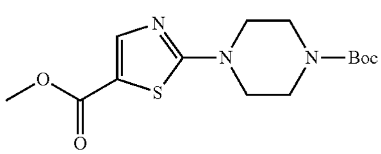 [SMILES: COC(=O)c1cnc(N2CCN(C(=O)OC(C)(C)C)CC2)s1] | tert-Butyl 4-[5-(methoxycarbonyl)-1,3-thiazol-2-yl]piperazine-1-carboxylate | White solid<br>Yield 712 mg, 64.4%<br>LCMS (ES$^+$): 350.2 [MNa]$^+$. HPLC: Rt 6.34 min, 99.0% purity. |

Intermediate 36

Methyl 6-(morpholin-4-yl methyl)pyridine-3-carboxylate

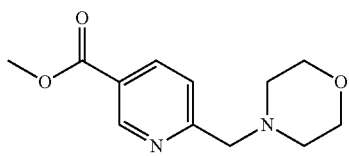 [SMILES: COC(=O)c1ccc(CN2CCOCC2)nc1]

Methyl 6-formylnicotinate (507 mg, 3.07 mmol) and morpholine (267 uL, 3.07 mmol) were dissolved in DCM (20 mL) and NaBH(OAc)$_3$ (976 mg, 4.60 mmol) was added. The reaction mixture was stirred for 2 h. The reaction mixture was diluted with DCM (40 mL) then washed with sat. aq. Na$_2$CO$_3$ (40 mL), dried (MgSO$_4$) and the solvents removed in vacuo to yield the title compound (660 mg, 91.0%) as a yellow oil. LCMS (ES$^+$): 237.2 [MH]$^+$.

Intermediate 37

Methyl 6-(cyclopropylcarbamoyl)pyridine-3-carboxylate

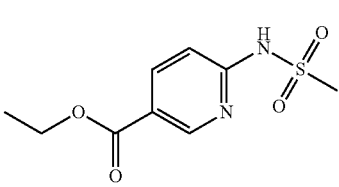 [SMILES: CCOC(=O)c1ccc(NS(C)(=O)=O)nc1]

Ethyl 6-aminopyridine-3-carboxylate (738 mg, 4.44 mmol) was dissolved in pyridine (20 mL), cooled to 0° C. and methanesulfonyl chloride (1.72 mL, 22.2 mmol) was added. The reaction mixture was stirred at RT for 16 h, concentrated in vacuo and partitioned between DCM (50 mL) and 1M aq. citric acid (50 mL). The organic fraction was dried (MgSO$_4$) and concentrated in vacuo to give the title compound (1.34 g, crude) as a brown solid. LCMS (ES$^+$): 245.1 [MH]$^+$.

Intermediate 38

2-[(Oxan-4-yl)amino]pyrimidine-5-carboxylic Acid

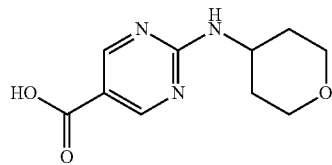 [SMILES: O=C(O)c1cnc(NC2CCOCC2)nc1]

2-Chloropyrimidine-5-carboxylic acid (500 mg, 3.15 mmol), Et$_3$N (1.15 mL, 8.20 mmol) and 4-aminotetrahydropyran (335 mg, 3.31 mmol) were dissolved in dioxane (10 mL) and heated in a microwave reactor at 150° C. for 30 min. The reaction mixture was concentrated in vacuo to give the title compound (701 mg, crude) as a beige solid. LCMS (ES$^+$): 224.1 [MH]$^+$.

Intermediates 39-50

Intermediates 39-50 were prepared similarly to Intermediate 38, by coupling of with the appropriate carboxylic acid with the appropriate amine; see Table 5 below.

TABLE 5

Coupling of with the appropriate carboxylic acid with the appropriate amine.

| Int | Structure | Name | Form, Yield, LCMS, HPLC |
|---|---|---|---|
| 39 | 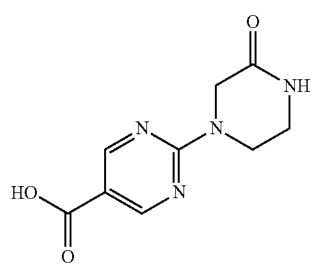 [SMILES: O=C1CN(c2ncc(C(=O)O)cn2)CCN1] | 2-(3-Oxopiperazin-1-yl)pyrimidine-5-carboxylic acid | Beige solid<br>Yield 701 mg, crude<br>LCMS (ES$^+$): 223.0 [MH]$^+$ |
| 40 | 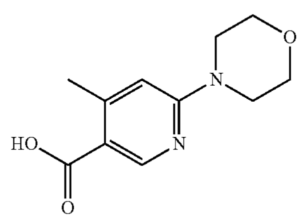 [SMILES: Cc1cc(N2CCOCC2)ncc1C(=O)O] | 4-Methyl-6-(morpholin-4-yl)pyridine-3-carboxylic acid | Off white solid<br>Yield 401 mg, 31.0%<br>LCMS (ES$^+$): 223.1 [MH]$^+$<br>HPLC: Rt 3.12 min, 80.5% purity |
| 41 | 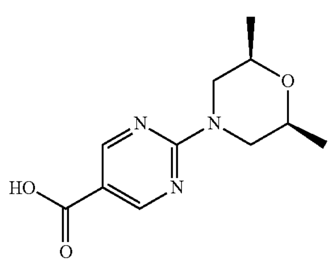 [SMILES: C[C@@H]1CN(c2ncc(C(=O)O)cn2)C[C@H](C)O1] | 2-[(2R,6S)-2,6-Dimethylmorpholin-4-yl]pyrimidine-5-carboxylic acid | Yellow gum<br>Yield 750 mg, 100%<br>LCMS (ES$^+$): 238.1 [MH]$^+$<br>HPLC: Rt 4.75 min, 96.5% purity |
| 42 | 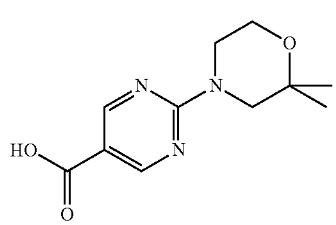 [SMILES: CC1(C)CN(c2ncc(C(=O)O)cn2)CCO1] | 2-(2,2-Dimethylmorpholin-4-yl)pyrimidine-5-carboxylic acid | Yellow gum<br>Yield 224 mg, 99.8%<br>LCMS (ES$^+$): 238.1 [MH]$^+$<br>HPLC: Rt 4.57 min, 96.2% purity |

TABLE 5-continued

Coupling of with the appropriate carboxylic acid with the appropriate amine.

| Int | Structure | Name | Form, Yield, LCMS, HPLC |
|---|---|---|---|
| 43 | 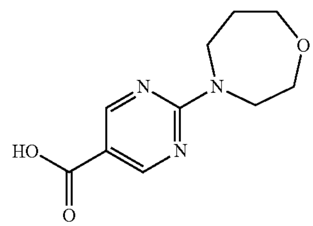 [SMILES: O=C(O)c1cnc(N2CCCOCC2)nc1] | 2-(1,4-Oxazepan-4-yl)pyrimidine-5-carboxylic acid | Beige solid<br>Yield 1.50 mg, 100%<br>LCMS (ES+): 224.1 [MH]+ |
| 44 | 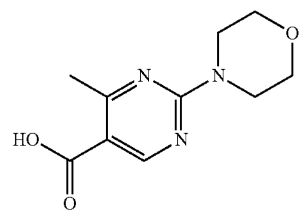 [SMILES: Cc1nc(N2CCOCC2)ncc1C(=O)O] | 4-Methyl-2-(morpholin-4-yl)pyrimidine-5-carboxylic acid | Yellow solid<br>Yield 540 mg, 83.5%<br>LCMS (ES+): 224.1 [MH]+<br>HPLC: Rt 4.28 min, 98.2% purity |
| 45 | 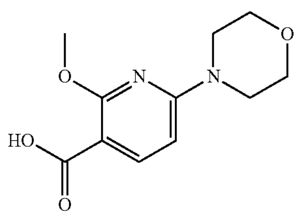 [SMILES: COc1nc(N2CCOCC2)ccc1C(=O)O] | 2-Methoxy-6-(morpholin-4-yl)pyridine-3-carboxylic acid | White solid<br>Yield 151 mg, 23.8%<br>LCMS (ES+): 239.1 [MH]+<br>HPLC: Rt 4.55 min, 84.0% purity |
| 46 | 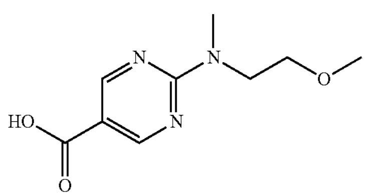 | 2-[(2-methoxyethyl)(methyl)amino]pyrimidine-5-carboxylic acid | Pale orange solid<br>Yield 752 mg, crude<br>LCMS (ES+): 212.0 [MH]+<br>HPLC: Rt 4.10 min, 94.9% purity |
| 47 | 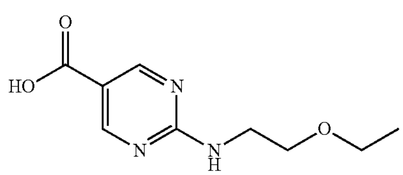 | 2-[(2-Ethoxyethyl)amino]pyrimidine-5-carboxylic acid | Orange solid<br>Yield 1.34 g, crude<br>LCMS (ES+): 212.1 [MH]+<br>HPLC: Rt 3.84 min, 87.0% purity |
| 48 | 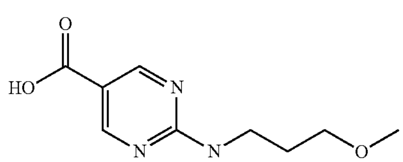 | 2-[(3-Methoxypropyl)amino]pyrimidine-5-carboxylic acid | Pale yellow solid<br>Yield 758 mg, crude<br>LCMS (ES+): 212.1 [MH]+<br>HPLC: Rt 3.67 min, 97.7% purity |
| 49 | 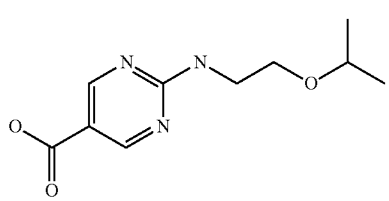 [SMILES: CC(C)OCCNc1ncc(C(=O)O)cn1] | 2-{[2-(Propan-2-yloxy)ethyl]amino}pyrimidine-5-carboxylic acid | Orange solid<br>Yield 1.79 g, crude<br>LCMS (ES+): 226.1 [MH]+<br>HPLC: Rt 4.25 min, 98.4% purity |

TABLE 5-continued

Coupling of with the appropriate carboxylic acid with the appropriate amine.

| Int | Structure | Name | Form, Yield, LCMS, HPLC |
|---|---|---|---|
| 50 | (structure shown) | 2-(4-Methyl-3-oxopiperazin-1-yl)pyrimidine-5-carboxylic acid | White solid<br>Yield 1.95 g, 87.0%<br>LCMS (ES$^+$): 237.1 [MH]$^+$<br>HPLC: Rt 3.63 min, 99.8% purity |

Intermediate 51

6-[(Morpholin-4-yl)carbonyl]pyridine-3-carboxylic Acid

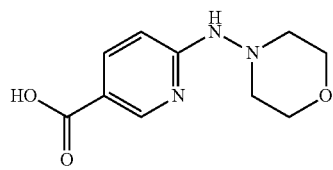 [SMILES: O=C(O)c1ccc(NN2CCOCC2)nc1]

Intermediate 26 (914 mg, 3.65 mmol) was dissolved in THF/water (24 mL, 1:1), lithium hydroxide monohydrate (184 mg, 4.38 mmol) was added and the reaction mixture was stirred for 20 min. 1M aq. HCl (5 mL) was added and the reaction mixture was extracted with EtOAc (2×100 mL), dried (MgSO$_4$) and concentrated in vacuo to give the title compound (633 mg, 73.4%) as a white solid. LCMS (ES$^+$): 237.1 [MH]$^+$.

Intermediates 52-62

Intermediates 52-62 were prepared similarly to Intermediate 51, by LiOH mediated ester hydrolysis; see Table 6 below.

TABLE 6

Ester hydrolyses

| Int | Structure | Name | Intermediate(s), Form, Yield, LCMS, HPLC |
|---|---|---|---|
| 52 | (structure shown) | Lithium 5-[(oxan-4-yl)amino]pyrazine-2-carboxylate | From Intermediate 28<br>Yellow solid<br>Yield 222 mg, 100%<br>LCMS (ES$^+$): 224.1 [MH]$^+$ |
| 53 | (structure shown) | Lithium 6-(4-{[(tert-butoxy)carbonyl] amino}piperidin-1-yl)pyridine-3-carboxylate | From Intermediate 29<br>White solid<br>Used crude<br>LCMS (ES$^+$): 322.1 [MH]$^+$ HPLC: Rt 4.20 min, 96.8% purity |

TABLE 6-continued

Ester hydrolyses

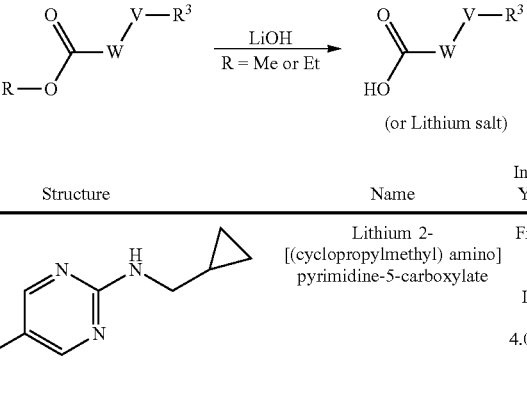

(or Lithium salt)

| Int | Structure | Name | Intermediate(s), Form, Yield, LCMS, HPLC |
|---|---|---|---|
| 54 | 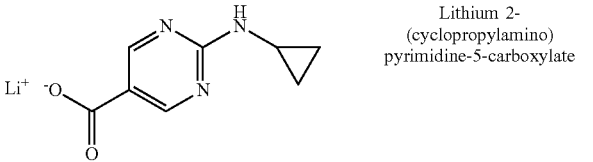 | Lithium 2-[(cyclopropylmethyl) amino] pyrimidine-5-carboxylate | From Intermediate 30 Off white solid Used crude LCMS (ES$^+$): 194.1 [MH]$^+$ HPLC: Rt 4.09 min, 97.4% purity |
| 55 | 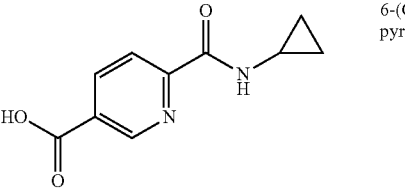 | Lithium 2-(cyclopropylamino) pyrimidine-5-carboxylate | From Intermediate 31 Off white solid Used crude LCMS (ES$^+$): 180.1 [MH]$^+$ HPLC: Rt 3.23 min, 100% purity |
| 56 | 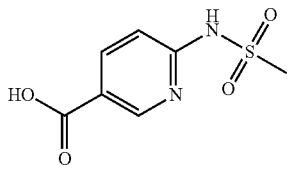 | 6-(Cyclopropylcarbamoyl) pyridine-3-carboxylic acid | From Intermediate 27 Pink solid Yield 559 mg, 77.1% LCMS (ES$^+$): 207.1 [MH]$^+$ |
| 57 | 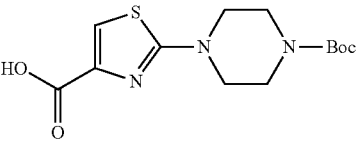 [SMILES: CC(C)(C)OC(=O)N1CCN(c2nc(C(=O)O)cs2)CC1] | 6-Methanesulfonamido pyridine-3-carboxylic acid | From Intermediate 37 Beige solid Yield 737 mg, 76.4% LCMS (ES$^+$): 217.0 [MH]$^+$ |
| 58 | 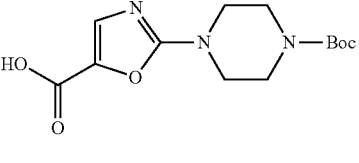 [SMILES: CC(C)(C)OC(=O)N1CCN(c2ncc(C(=O)O)o2)CC1] | 2-{4-[(tert-Butoxy)carbonyl] piperazin-1-yl}-1,3-thiazole-4-carboxylic acid | From Intermediate 33 White solid Yield 275 mg, 88.7% LCMS (ES$^+$): 336.1 [MNa]$^+$ HPLC: Rt 5.12 min, 100% purity |
| 59 | 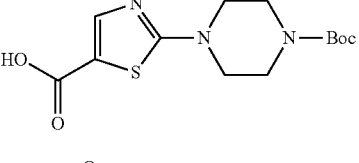 | 2-{4-[(tert-Butoxy)carbonyl] piperazin-1-yl}-1,3-oxazole-5-carboxylic acid | From Intermediate 34 White solid Yield 324 mg, 84.4% LCMS (ES$^+$): 320.1 [MNa]$^+$ HPLC: Rt 4.77 min, 100% purity |
| 60 | 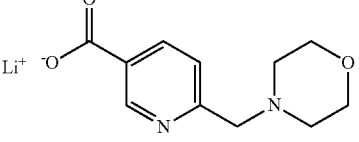 | 2-{4-[(tert-Butoxy)carbonyl] piperazin-1-yl}-1,3-thiazole-5-carboxylic acid | From Intermediate 35 White solid Yield 656 mg, 97.9% LCMS (ES$^+$): 336.1 [MNa]$^+$ HPLC: Rt 5.19 min, 99.3% purity |
| 61 | 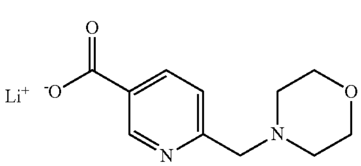 | Lithium 6-(morpholin-4-yl methyl)pyridine-3-carboxylate | From Intermediate 36 Yellow solid Used crude LCMS (ES$^+$): 223.1 [MH]$^+$ |

TABLE 6-continued

Ester hydrolyses $$R-O-\overset{O}{\underset{}{C}}-W\overset{V-R^3}{\underset{}{}} \xrightarrow[R = Me\ or\ Et]{LiOH} HO-\overset{O}{\underset{}{C}}-W\overset{V-R^3}{\underset{}{}}$$

(or Lithium salt)

| Int | Structure | Name | Intermediate(s), Form, Yield, LCMS, HPLC |
|---|---|---|---|
| 62 | 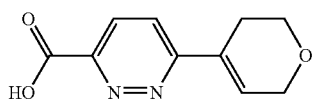 | Lithium 5-(morpholin-4-yl)pyrazine-2-carboxylate | From Intermediate 32 Yellow solid Used crude LCMS (ES$^+$): 210.1 [MH]$^+$ |

Intermediate 63

6-(3,6-Dihydro-2H-pyran-4-yl)pyridazine-3-carboxylic Acid

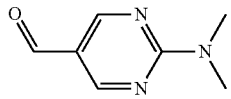

Methyl 6-chloropyridazine-3-carboxylate (1.00 g, 5.79 mmol), 4-(4,4,5,5-tetramethyl-1,3,2-dioxaborolan-2-yl)-3,6-dihydro-2H-pyran (1.22 g, 5.79 mmol), Pd(PPh$_3$)$_4$ (536 mg, 0.464 mmol) and Cs$_2$CO$_3$ (3.40 g, 10.4 mmol) were suspended in dioxane (8 mL) and water (8 mL) and heated in a microwave reactor at 125° C. for 30 min. 1M aq. HCl (10 mL) was added, the precipitate was removed by filtration and the filtrate was concentrated in vacuo. The residue was passed through a silica pad eluting with 30% MeOH in DCM and concentrated in vacuo to give the title compound as a white solid (946 mg, 79.2%). LCMS (ES$^+$): 207.1 [MH]$^+$. HPLC: Rt 3.30 min, 49.9% purity.

Intermediate 64

2-(Dimethylamino)pyrimidine-5-carbaldehyde

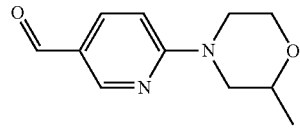

2-Chloropyrimidine-5-carbaldehyde (412 mg, 2.89 mmol) and Et$_3$N (482 uL, 3.47 mmol) were dissolved in dioxane (20 mL) and a solution of Me$_2$NH in THF (1.59 mL, 2.0M, 3.18 mmol) was added. The reaction mixture was stirred for 1 h, filtered, washed with dioxane (5 mL), and concentrated in vacuo to give the title compound (427 mg, 97.7%) as a yellow solid. LCMS (ES$^+$): 152.2 [MH]$^+$. HPLC: Rt 4.14 min, 97.9% purity.

Intermediate 65

6-(2-Methylmorpholin-4-yl)pyridine-3-carbaldehyde

2-Chloro-5-pyridinecarboxaldehyde (500 mg, 3.53 mmol) and 2-methylmorpholine (750 mg, 7.42 mmol) were dissolved in DMF (2 mL) and the reaction mixture was heated at 100° C. in a microwave reactor for 20 min and concentrated in vacuo. The residue was suspended in dioxane (5 mL), filtered and concentrated in vacuo to give the title compound (730 mg, 100%) as an orange gum. LCMS (ES$^+$): 207.1 [MH]$^+$.

Intermediate 66

N-{3-[(4-Chlorophenyl)amino]pyridin-4-yl}pyridine-3-carboxamide

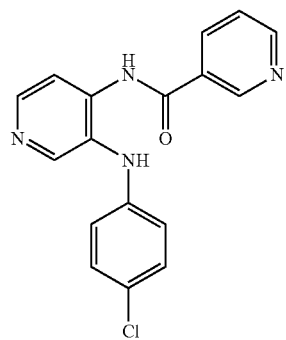 [SMILES: O=C(Nc1ccncc1Nc1ccc(Cl)cc1)c1cccnc1]

Intermediate 19 (234 mg, 1.07 mmol), pyridine-4-carboxylic acid (393 mg, 3.20 mmol) and DIPEA (741 uL, 4.26 mmol) were dissolved in DMF (10 mL) and EDC (613 mg, 3.20 mmol) was added. The reaction mixture was stirred for 18 h and further pyridine-3-carboxylic acid (393 mg, 3.20 mmol) and EDC (613 mg, 3.20 mmol) were added. The reaction mixture was stirred for 5 h, diluted with 1M aq. Na$_2$CO$_3$ (50 mL) and extracted into DCM (3×50 mL). The combined organic fractions were dried (MgSO$_4$) and concentrated in vacuo. The residue was purified by column chromatography to give the title compound as a red gum (297 mg, 85.8%). LCMS (ES$^+$): 325.1 [MH]$^+$. HPLC: Rt 4.08 min, 99.0% purity.

Intermediates 67-123

Intermediates 67-123 were prepared similarly to Intermediate 66, by coupling of Intermediates 19-25 with the appropriate carboxylic acid; see Table 7 below.

TABLE 7

Amide couplings

| Int | Structure | Name | Intermediate(s), Form, Yield, LCMS, HPLC |
|---|---|---|---|
| 67 | 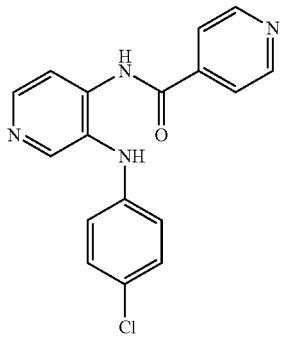 [SMILES: O=C(Nc1ccncc1Nc1ccc(Cl)cc1)c1ccncc1] | N-{3-[(4-Chlorophenyl)amino]pyridin-4-yl}pyridine-4-carboxamide | From Intermediate 19<br>Yellow solid<br>Yield 219 mg, 58.3%<br>LCMS (ES$^+$): 325.2 [MH]$^+$<br>HPLC: Rt 4.18 min, 95.8% purity |
| 68 | 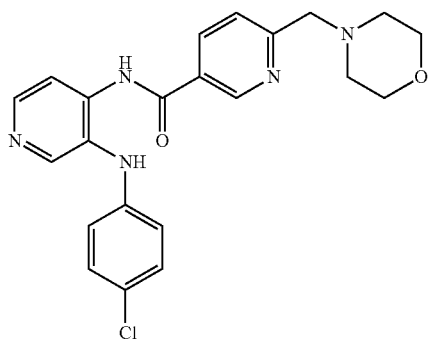 [SMILES: O=C(Nc1ccncc1Nc1ccc(Cl)cc1)c1ccc(CN2CCOCC2)nc1] | N-{3-[(4-Chlorophenyl)amino]pyridin-4-yl}-6-(morpholin-4-ylmethyl)pyridine-3-carboxamide | From Intermediates 19 and 61<br>Yellow solid<br>Yield 282 mg, 21.1%<br>LCMS (ES$^+$): 424.1 [MH]$^+$ |

TABLE 7-continued

Amide couplings

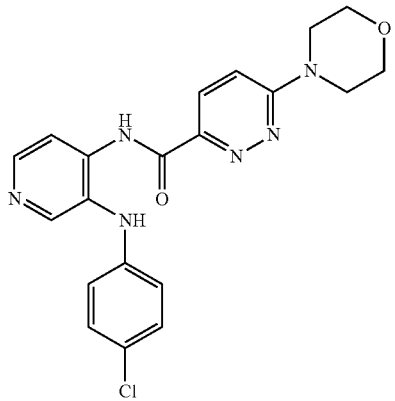 [SMILES: O=C(Nc1ccncc1Nc1ccc(Cl)cc1)c1ccc(N2CCOCC2)nn1]

| Int | Structure | Name | Intermediate(s), Form, Yield, LCMS, HPLC |
|---|---|---|---|
| 69 | 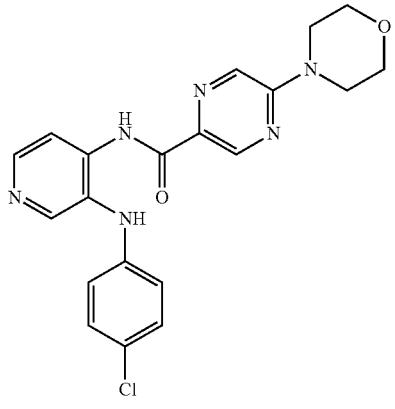 [SMILES: O=C(Nc1ccncc1Nc1ccc(Cl)cc1)c1cnc(N2CCOCC2)cn1] | N-{3-[(4-Chlorophenyl)amino]pyridin-4-yl}-6-(morpholin-4-yl)pyridazine-3-carboxamide | From Intermediate 19<br>Yellow solid<br>Yield 500 mg, 58.2%<br>LCMS (ES$^+$): 411.0 [MH]$^+$ |
| 70 | 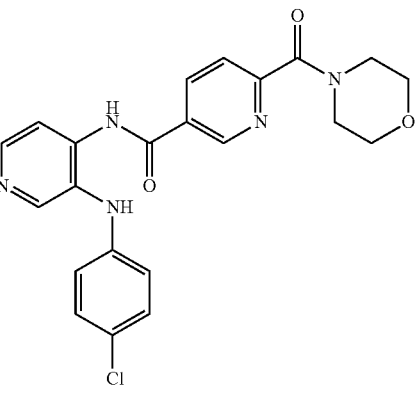 | N-{3-[(4-Chlorophenyl)amino]pyridin-4-yl}-5-(morpholin-4-yl)pyrazine-2-carboxamide | From Intermediates 19 and 62<br>Yellow oil<br>Yield 633 mg, 73.5%<br>LCMS (ES$^+$): 411.0 [MH]$^+$ |
| 71 | 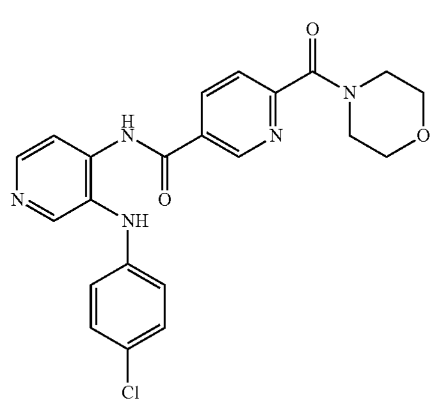 [SMILES: O=C(Nc1ccncc1Nc1ccc(Cl)cc1)c1ccc(C(=O)N2CCOCC2)nc1] | N-{3-[(4-Chlorophenyl)amino]pyridin-4-yl}-6-[(morpholin-4-yl)carbonyl]pyridine-3-carboxamide | From Intermediates 19 and 51<br>Yellow oil<br>Yield 437 mg, 54.9%<br>LCMS (ES$^+$): 438.0 [MH]$^+$ |

TABLE 7-continued

Amide couplings

| Int | Structure | Name | Intermediate(s), Form, Yield, LCMS, HPLC |
|---|---|---|---|
| 72 | 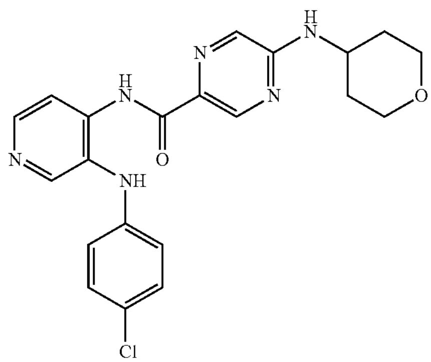 [SMILES: O=C(Nc1ccncc1Nc1ccc(Cl)cc1)c1cnc(NC2CCOCC2)cn1] | N-{3-[(4-Chlorophenyl)amino]pyridin-4-yl}-5-[(oxan-4-yl)amino]pyrazine-2-carboxamide | From Intermediates 19 and 52<br>Yellow oil<br>Yield 174 mg, 45.6%<br>LCMS (ES$^+$): 425.1 [MH]$^+$ |
| 73 | 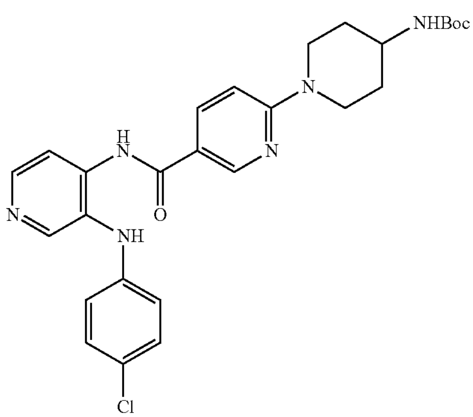 [SMILES: CC(C)(C)OC(=O)NC1CCN(c2ccc(C(=O)Nc3ccncc3Nc3ccc(Cl)cc3)cn2)CC1] | tert-Butyl N-{1-[5-({3-[(4-chlorophenyl)amino]pyridin-4-yl}carbamoyl)pyridin-2-yl]piperidin-4-yl}carbamate | From Intermediates 19 and 53<br>Off white solid<br>Yield 954 mg, 76.4%<br>LCMS (ES$^+$): 523.1 [MH]$^+$<br>HPLC: Rt 5.16 min, 97.8% purity |
| 74 | 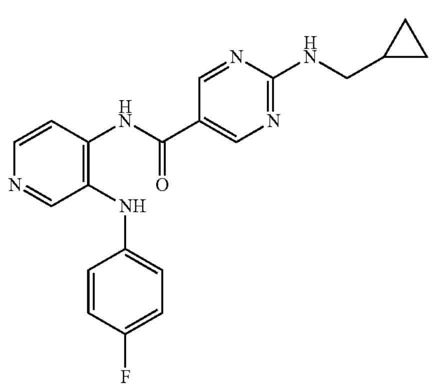 [SMILES: O=C(Nc1ccncc1Nc1ccc(F)cc1)c1cnc(NCC2CC2)nc1] | 2-[(Cyclopropylmethyl)amino]-N-{3-[(4-fluorophenyl)amino]pyridin-4-yl}pyrimidine-5-carboxamide | From Intermediates 20 and 54<br>Yellow solid<br>Yield 312 mg, 32.3%<br>LCMS (ES$^+$): 379.2 [MH]$^+$<br>HPLC: Rt 4.91 min, 96.3% purity |

TABLE 7-continued

Amide couplings

| Int | Structure | Name | Intermediate(s), Form, Yield, LCMS, HPLC |
|---|---|---|---|
| 75 | 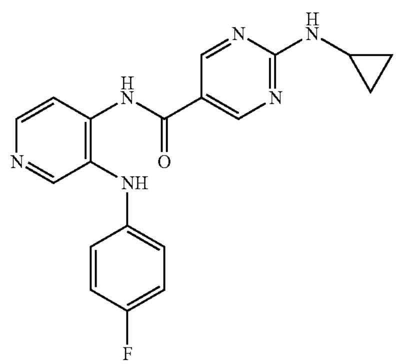 [SMILES: O=C(Nc1ccncc1Nc1ccc(F)cc1)c1cnc(NC2CC2)nc1] | 2-(Cyclopropylamino)-N-{3-[(4-fluorophenyl)amino]pyridin-4-yl}pyrimidine-5-carboxamide | From Intermediates 20 and 55<br>Yellow solid<br>Yield 659 mg, 71.2%<br>LCMS (ES$^+$): 365.1 [MH]$^+$<br>HPLC: Rt 4.41 min, 68.3% purity |
| 76 | 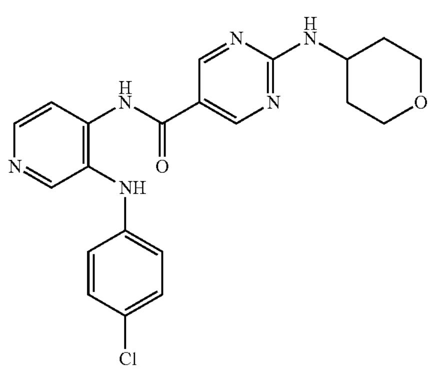 [SMILES: O=C(Nc1ccncc1Nc1ccc(Cl)cc1)c1cnc(NC2CCOCC2)nc1] | N-{3-[(4-Chlorophenyl)amino]pyridin-4-yl}-2-[(oxan-4-yl)amino]pyrimidine-5-carboxamide | From Intermediates 19 and 38<br>Yellow oil<br>Yield 917 mg, 86.3%<br>LCMS (ES$^+$): 425.1 [MH]$^+$ |
| 77 | 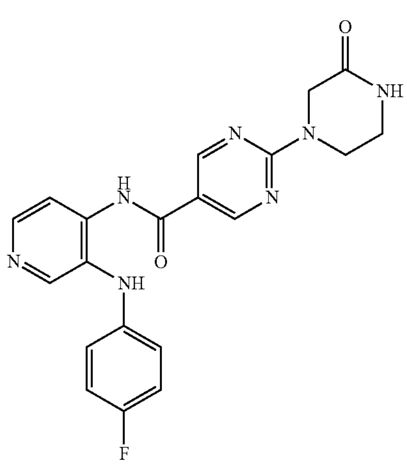 [SMILES: O=C1CN(c2ncc(C(=O)Nc3ccncc3Nc3ccc(F)cc3)cn2)CCN1] | N-{3-[(4-Fluorophenyl)amino]pyridin-4-yl}-2-(3-oxopiperazin-1-yl)pyrimidine-5-carboxamide | From Intermediates 20 and 39<br>Yellow gum<br>Used crude (1.88 g)<br>LCMS (ES$^+$): 408.1 [MH]$^+$ |

TABLE 7-continued

Amide couplings

| Int | Structure | Name | Intermediate(s), Form, Yield, LCMS, HPLC |
|---|---|---|---|
| 78 | 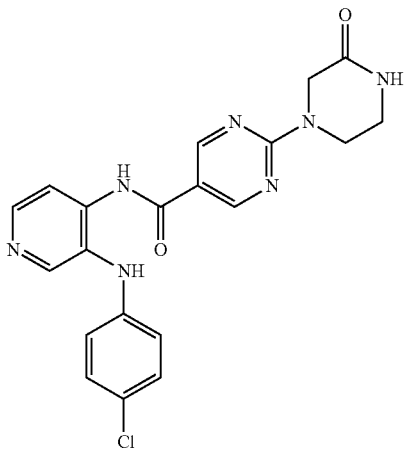 [SMILES: O=C1CN(c2ncc(C(=O)Nc3ccncc3Nc3ccc(Cl)cc3)cn2)CCN1] | N-{3-[(4-Chlorophenyl)amino]pyridin-4-yl}-2-(3-oxopiperazin-1-yl)pyrimidine-5-carboxamide | From Intermediates 19 and 39<br>Yellow solid<br>Yield 712 mg, 58.8%<br>LCMS (ES$^+$): 424.1 [MH]$^+$ |
| 79 | 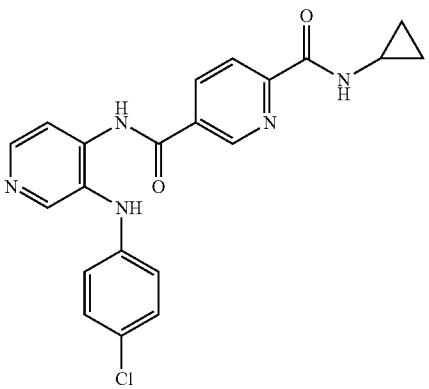 [SMILES: O=C(Nc1ccncc1Nc1ccc(Cl)cc1)c1ccc(C(=O)NC2CC2)nc1] | 5-N-{3-[(4-Chlorophenyl)amino]pyridin-4-yl}-2-N-cyclopropylpyridine-2,5-dicarboxamide | From Intermediates 19 and 56<br>Yellow solid<br>Yield 790 mg, 84.9%<br>LCMS (ES$^+$): 408.1 [MH]$^+$ |
| 80 | 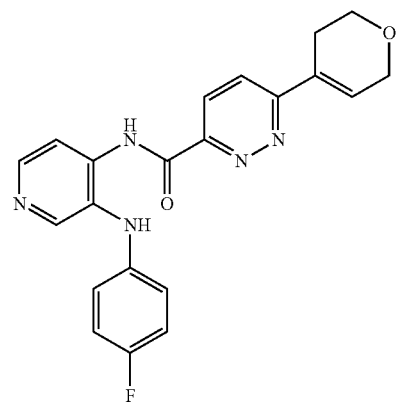 [SMILES: O=C(Nc1ccncc1Nc1ccc(F)cc1)c1ccc(C2=CCOCC2)nn1] | 6-(3,6-Dihydro-2H-pyran-4-yl)-N-{3-[(4-fluorophenyl)amino]pyridin-4-yl}pyridazine-3-carboxamide | From Intermediates 20 and 63<br>Orange semi-solid<br>Yield 467 mg, 54.7%<br>LCMS (ES$^+$): 392.2 [MH]$^+$<br>HPLC: Rt 4.87 min, 50.9% purity |

TABLE 7-continued

Amide couplings

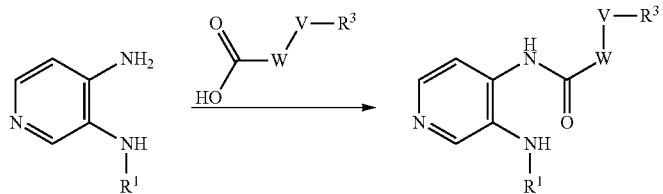

| Int | Structure | Name | Intermediate(s), Form, Yield, LCMS, HPLC |
|---|---|---|---|
| 81 | 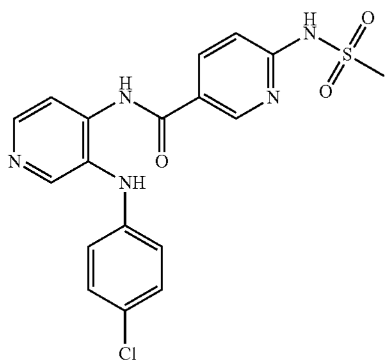 [SMILES: CS(=O)(=O)Nc1ccc(C(=O)Nc2ccncc2Nc2ccc(Cl)cc2)cn1] | N-{3-[(4-Chlorophenyl)amino]pyridin-4-yl}-6-methanesulfonamidopyridine-3-carboxamide | From Intermediates 19 and 57<br>Beige solid<br>Yield 348 mg, 40.6%<br>LCMS (ES$^+$): 418.0 [MH]$^+$ |
| 82 | 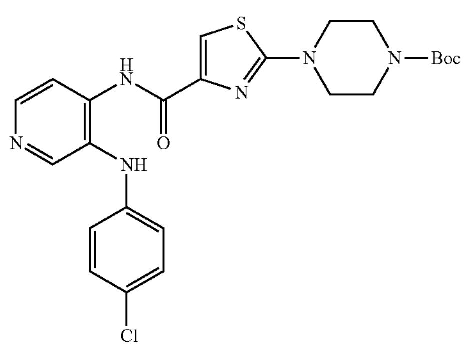 [SMILES: CC(C)(C)OC(=O)N1CCN(c2nc(C(=O)Nc3ccncc3Nc3ccc(Cl)cc3)cs2)CC1] | tert-Butyl 4-[4-({3-[(4-chlorophenyl)amino]pyridin-4-yl}carbamoyl)-1,3-thiazol-2-yl]piperazine-1-carboxylate | From Intermediates 19 and 58<br>White solid<br>Yield 302 mg, 66.8%<br>LCMS (ES$^+$): 515.0 [MH]$^+$<br>HPLC: Rt 6.37 min, 94.2% purity |
| 83 | 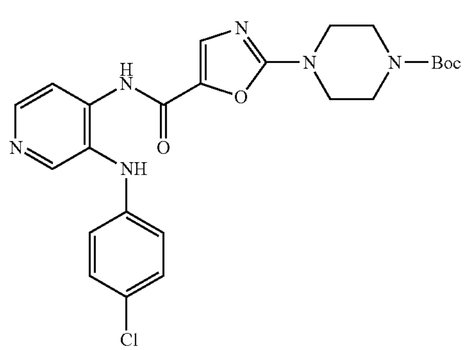 [SMILES: CC(C)(C)OC(=O)N1CCN(c2ncc(C(=O)Nc3ccncc3Nc3ccc(Cl)cc3)o2)CC1] | tert-Butyl 4-[5-({3-[(4-chlorophenyl)amino]pyridin-4-yl}carbamoyl)-1,3-oxazol-2-yl]piperazine-1-carboxylate | From Intermediates 19 and 59<br>Orange solid<br>Used crude (602 mg)<br>LCMS (ES$^+$): 499.0 [MH]$^+$<br>HPLC: Rt 5.76 min, 76.4% purity |

TABLE 7-continued

Amide couplings

| Int | Structure | Name | Intermediate(s), Form, Yield, LCMS, HPLC |
|---|---|---|---|
| 84 | 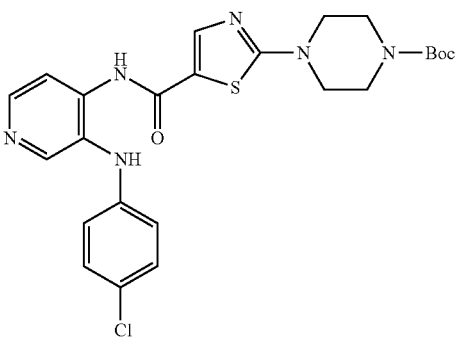 [SMILES: CC(C)(C)OC(=O)N1CCN(c2ncc(C(=O)Nc3ccncc3Nc3ccc(Cl)cc3)s2)CC1] | tert-Butyl 4-[5-({3-[(4-chlorophenyl)amino]pyridin-4-yl}carbamoyl)-1,3-thiazol-2-yl]piperazine-1-carboxylate | From Intermediates 19 and 60<br>Yellow solid<br>Yield 417 mg, 39.2%<br>LCMS (ES$^+$): 515.1 [MH]$^+$<br>HPLC: Rt 5.95 min, 39.1% purity |
| 85 | 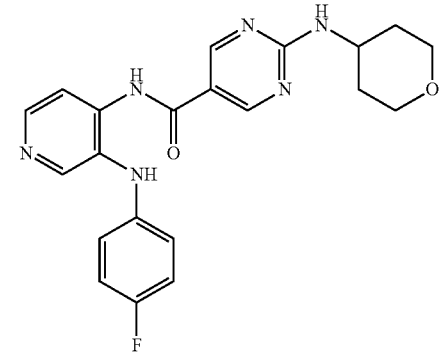 [SMILES: O=C(Nc1ccncc1Nc1ccc(F)cc1)c1cnc(NC2CCOCC2)nc1] | N-{3-[(4-fluorophenyl)amino]pyridin-4-yl}-2-[(oxan-4-yl)amino]pyrimidine-5-carboxamide | From Intermediates 20 and 38<br>Beige solid<br>Yield 593 mg, 59.0%<br>LCMS (ES$^+$): 409.1 [MH]$^+$ |
| 86 | 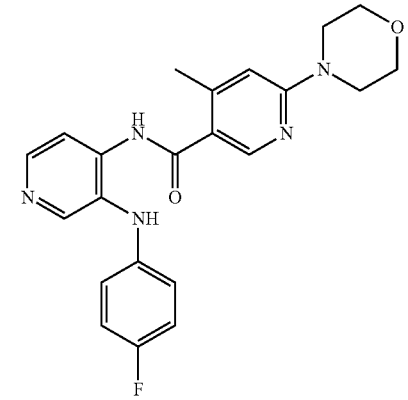 | N-{3-[(4-Fluorophenyl)amino]pyridin-4-yl}-4-methyl-6-(morpholin-4-yl)pyridine-3-carboxamide | From Intermediates 20 and 40<br>Light brown oil<br>Yield 645 mg, crude<br>LCMS (ES$^+$): 408.2 [MH]$^+$ |

TABLE 7-continued

Amide couplings

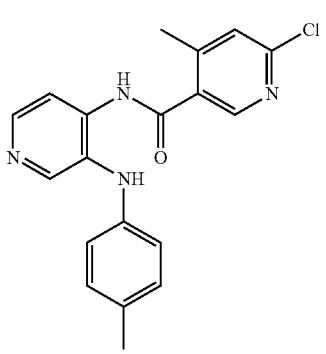 [SMILES: Cc1ccc(Nc2cnccc2NC(=O)c2cnc(Cl)cc2C)cc1]

| Int | Structure | Name | Intermediate(s), Form, Yield, LCMS, HPLC |
|---|---|---|---|
| 87 | 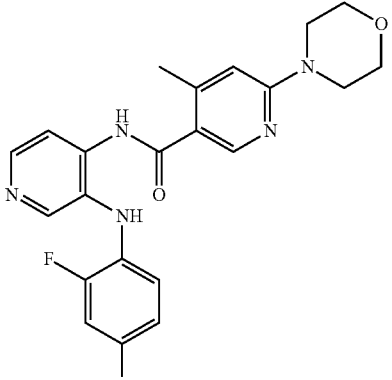 | 6-Chloro-4-methyl-N-{3-[(4-methylphenyl)amino]pyridin-4-yl}pyridine-3-carboxamide | From Intermediates 21<br>Dark oil<br>used crude<br>LCMS (ES$^+$): 353.0 [MH]$^+$ |
| 88 | 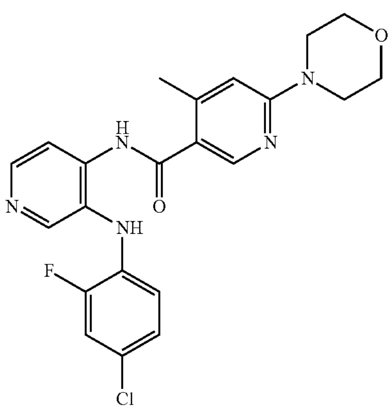 [SMILES: Cc1cc(N2CCOCC2)ncc1C(=O)Nc1ccncc1Nc1ccc(Cl)cc1F] | N-{3-[(4-Chloro-2-fluorophenyl)amino]pyridin-4-yl}-4-methyl-6-(morpholin-4-yl)pyridine-3-carboxamide | From Intermediates 22 and 40<br>Orange oil<br>used crude<br>LCMS (ES$^+$): 442.1 [MH]$^+$ |
| 89 | 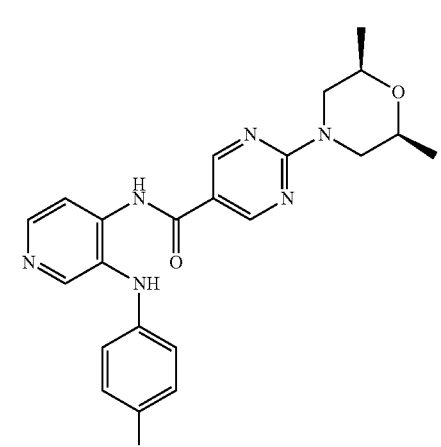 | 2-[(2R,6S)-2,6-Dimethylmorpholin-4-yl]-N-{3-[(4-fluorophenyl)amino]pyridin-4-yl}pyrimidine-5-carboxamide | From Intermediates 20 and 41<br>Yellow gum<br>Yield 422 mg, 79.0%<br>LCMS (ES$^+$): 423.1 [MH]$^+$<br>HPLC: Rt 5.25 min, 67.8% purity |

TABLE 7-continued

Amide couplings

| Int | Structure | Name | Intermediate(s), Form, Yield, LCMS, HPLC |
|---|---|---|---|
| 90 | 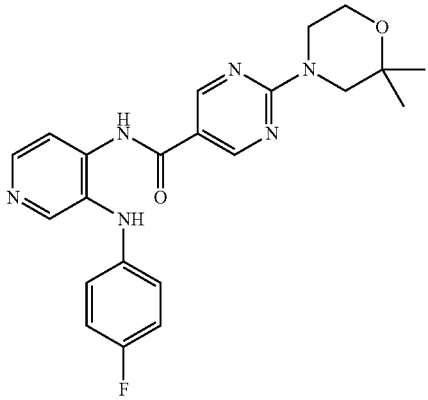 [SMILES: CC1(C)CN(c2ncc(C(=O)Nc3ccncc3Nc3ccc(F)cc3)cn2)CCO1] | 2-(2,2-Dimethylmorpholin-4-yl)-N-{3-[(4-fluorophenyl)amino]pyridin-4-yl}pyrimidine-5-carboxamide | From Intermediates 20 and 42<br>Yellow gum<br>Yield 338 mg, 84.7%<br>LCMS (ES+): 423.1 [MH]+<br>HPLC: Rt 5.12 min, 75.5% purity |
| 91 | 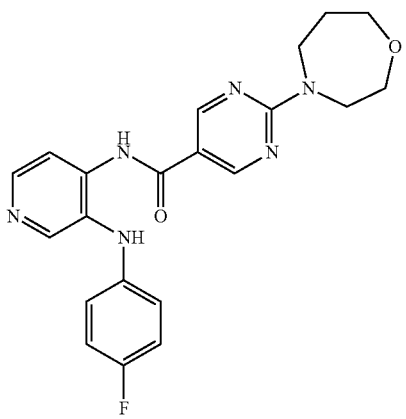 [SMILES: O=C(Nc1ccncc1Nc1ccc(F)cc1)c1cnc(N2CCCOCC2)nc1] | N-{3-[(4-Fluorophenyl)amino]pyridin-4-yl}-2-(1,4-oxazepan-4-yl)pyrimidine-5-carboxamide | From Intermediates 20 and 43<br>Yellow solid<br>Yield 1.96 g, 97.7%<br>LCMS (ES+): 409.2 [MH]+ |
| 92 | 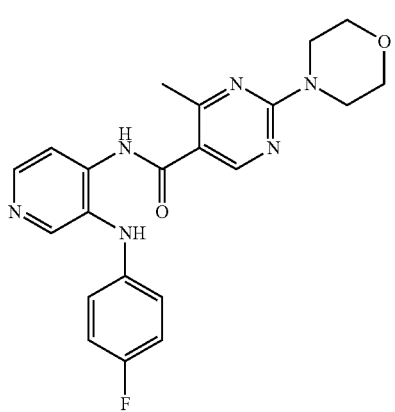 [SMILES: Cc1nc(N2CCOCC2)ncc1C(=O)Nc1ccncc1Nc1ccc(F)cc1] | N-{3-[(4-Fluorophenyl)amino]pyridin-4-yl}-4-methyl-2-(morpholin-4-yl)pyrimidine-5-carboxamide | From Intermediates 20 and 44<br>Orange oil<br>used crude<br>LCMS (ES+): 409.2 [MH]+ |

TABLE 7-continued

Amide couplings

| Int | Structure | Name | Intermediate(s), Form, Yield, LCMS, HPLC |
|---|---|---|---|
| 93 | 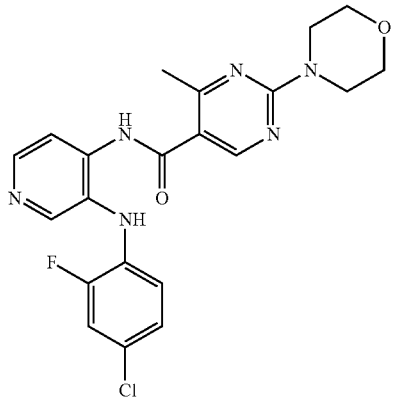 | N-{3-[(4-Chloro-2-fluorophenyl)amino]pyridin-4-yl}-4-methyl-2-(morpholin-4-yl)pyrimidine-5-carboxamide | From Intermediates 22 and 44<br>Orange oil<br>used crude<br>LCMS (ES$^+$): 443.1 [MH]$^+$ |
| 94 | 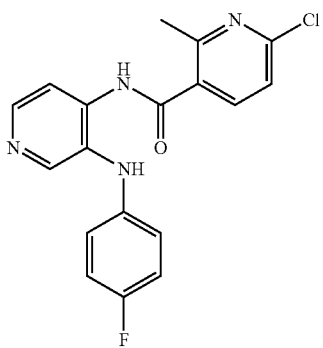 [SMILES: Cc1nc(Cl)ccc1C(=O)Nc1ccncc1Nc1ccc(F)cc1] | 6-Chloro-N-{3-[(4-fluorophenyl)amino]pyridin-4-yl}-2-methylpyridine-3-carboxamide | From Intermediate 20<br>Orange oil<br>used crude<br>LCMS (ES$^+$): 357.1 [MH]$^+$ |
| 95 | 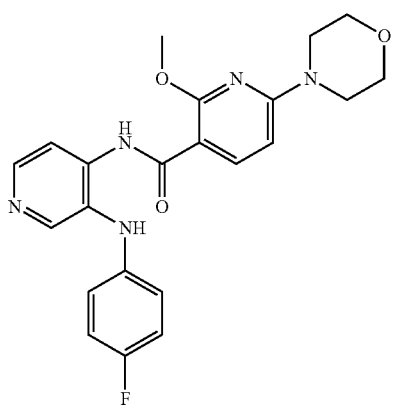 [SMILES: COc1nc(N2CCOCC2)ccc1C(=O)Nc1ccncc1Nc1ccc(F)cc1] | N-{3-[(4-Fluorophenyl)amino]pyridin-4-yl}-2-methoxy-6-(morpholin-4-yl)pyridine-3-carboxamide | From Intermediates 20 and 45<br>Yellow solid<br>Yield 119 mg, 44.3%<br>LCMS (ES$^+$): 424.1 [MH]$^+$<br>HPLC: Rt 5.46 min, 100% purity |

TABLE 7-continued

Amide couplings

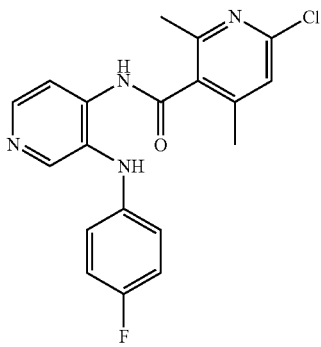 [SMILES: Cc1cc(Cl)nc(C)c1C(=O)Nc1ccncc1Nc1ccc(F)cc1]

| Int | Structure | Name | Intermediate(s), Form, Yield, LCMS, HPLC |
|---|---|---|---|
| 96 | 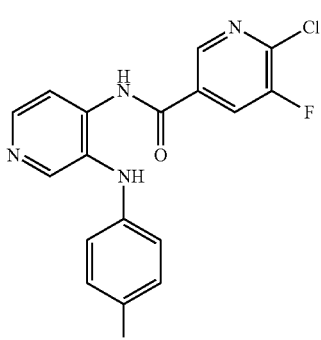 | 6-Chloro-N-{3-[(4-fluorophenyl)amino]pyridin-4-yl}-2,4-dimethylpyridine-3-carboxamide | From Intermediate 20 used crude LCMS (ES$^+$): 371.0 [MH]$^+$ |
| 97 | 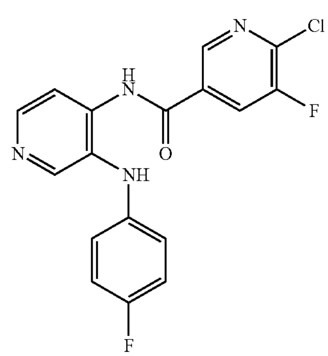 [SMILES: O=C(Nc1ccncc1Nc1ccc(F)cc1)c1cnc(Cl)c(F)c1] | 6-Chloro-5-fluoro-N-{3-[(4-fluorophenyl)amino]pyridin-4-yl}pyridine-3-carboxamide | From Intermediate 20 used crude LCMS (ES$^+$): 360.9 [MH]$^+$ |
| 98 | 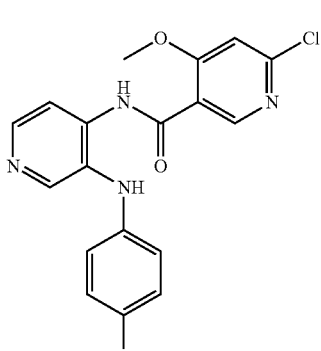 | 6-Chloro-N-{3-[(4-fluorophenyl)amino]pyridin-4-yl}-4-methoxypyridine-3-carboxamide | From Intermediate 20 used crude LCMS (ES$^+$): 373.0 [MH]$^+$ |

TABLE 7-continued

Amide couplings

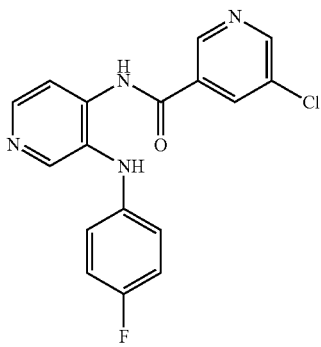 [SMILES: O=C(Nc1ccncc1Nc1ccc(F)cc1)c1cncc(Cl)c1]

| Int | Structure | Name | Intermediate(s), Form, Yield, LCMS, HPLC |
|---|---|---|---|
| 99 | 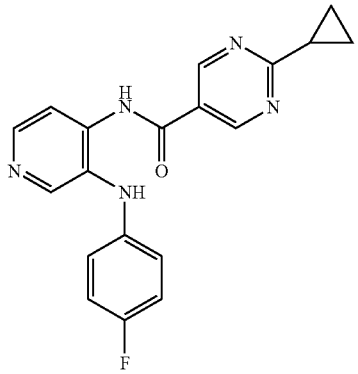 | 2-Chloro-N-{3-[(4-fluorophenyl)amino]pyridin-4-yl}pyridine-4-carboxamide | From Intermediate 20<br>Yellow solid<br>Yield 608 mg, 76.6%<br>LCMS (ES$^+$): 343.1 [MH]$^+$ |
| 100 | 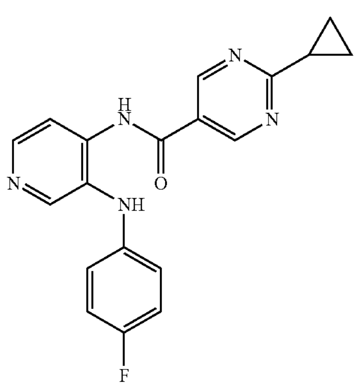 [SMILES: O=C(Nc1ccncc1Nc1ccc(F)cc1)c1cnc(C2CC2)nc1] | 2-Cyclopropyl-N-{3-[(4-fluorophenyl)amino]pyridin-4-yl}pyrimidine-5-carboxamide | From Intermediate 20<br>Brown gum<br>Yield 519 mg, crude<br>LCMS (ES$^+$): 349.8 [MH]$^+$ |
| 101 | 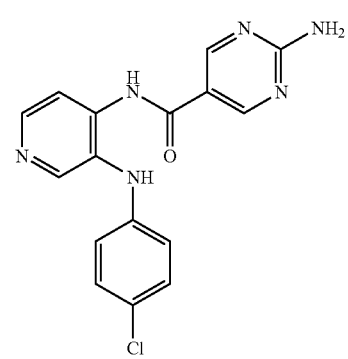 [SMILES: Nc1ncc(C(=O)Nc2ccncc2Nc2ccc(Cl)cc2)cn1] | 2-Amino-N-{3-[(4-chlorophenyl)amino]pyridin-4-yl}pyrimidine-5-carboxamide | From Intermediate 19<br>Orange oil<br>used crude<br>LCMS (ES$^+$): 340.7 [MH]$^+$ |

TABLE 7-continued

Amide couplings

| Int | Structure | Name | Intermediate(s), Form, Yield, LCMS, HPLC |
|---|---|---|---|
| 102 | 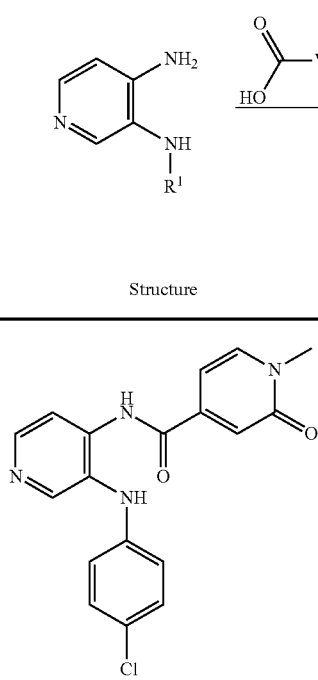 | N-{3-[(4-Chlorophenyl)amino]pyridin-4-yl}-1-methyl-2-oxo-1,2-dihydropyridine-4-carboxamide | From Intermediate 19<br>Orange oil<br>used crude<br>LCMS (ES$^+$): 355.1 [MH]$^+$ |
| 103 | 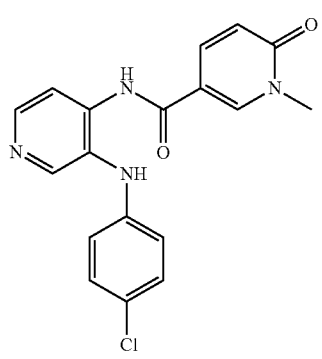 [SMILES: Cn1cc(C(=O)Nc2ccncc2Nc2ccc(Cl)cc2)ccc1=O] | N-{3-[(4-Chlorophenyl)amino]pyridin-4-yl}-1-methyl-6-oxo-1,6-dihydropyridine-3-carboxamide | From Intermediate 19<br>Orange oil<br>used crude<br>LCMS (ES$^+$): 355.1 [MH]$^+$ |
| 104 | 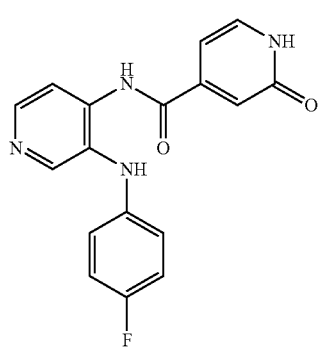 [SMILES: O=C(Nc1ccncc1Nc1ccc(F)cc1)c1cc[nH]c(=O)c1] | N-{3-[(4-Fluorophenyl)amino]pyridin-4-yl}-2-oxo-1,2-dihydropyridin-4-carboxamide | From Intermediate 20<br>Orange oil<br>used crude<br>LCMS (ES$^+$): 325.1 [MH]$^+$ |

TABLE 7-continued

Amide couplings

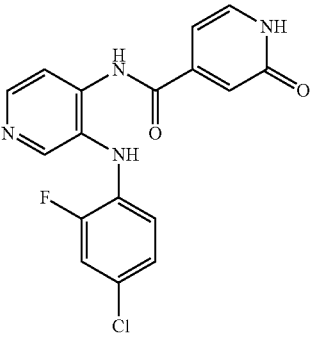 [SMILES: O=C(Nc1ccncc1Nc1ccc(Cl)cc1F)c1cc[nH]c(=O)c1]

| Int | Structure | Name | Intermediate(s), Form, Yield, LCMS, HPLC |
|---|---|---|---|
| 105 | 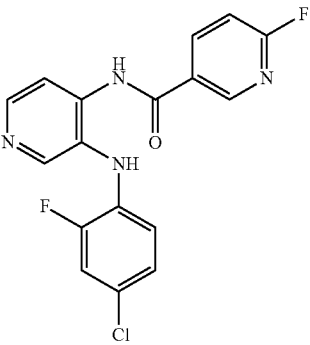 [SMILES: O=C(Nc1ccncc1Nc1ccc(Cl)cc1F)c1ccc(F)nc1] | N-{3-[(4-Chloro-2-fluorophenyl)amino]pyridin-4-yl}-2-oxo-1,2-dihydropyridine-4-carboxamide | From Intermediate 22<br>Orange oil<br>used crude<br>LCMS (ES$^+$): 359.1 [MH]$^+$ |
| 106 | 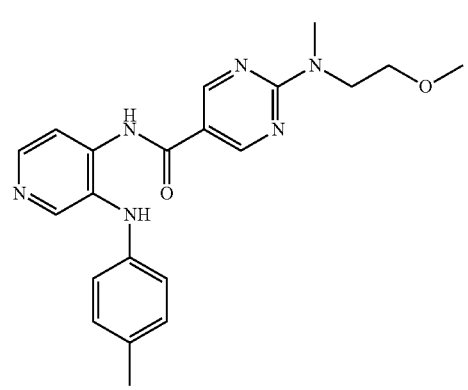 | N-{3-[(4-Chloro-2-fluorophenyl)amino]pyridin-4-yl}-6-fluoropyridine-3-carboxamide | From Intermediate 22<br>Orange oil<br>used crude<br>LCMS (ES$^+$): 361.1 [MH]$^+$ |
| 107 | 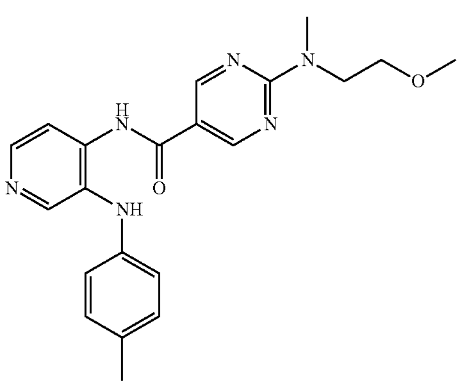 [SMILES: COCCN(C)c1ncc(C(=O)Nc2ccncc2Nc2ccc(C)cc2)cn1] | 2-[(2-Methoxyethyl)(methyl)amino]-N-{3-[(4-methylphenyl)amino]pyridin-4-yl}pyrimidine-5-carboxamide | From Intermediates 21 and 46<br>Dark oil<br>used crude<br>LCMS (ES$^+$): 393.0 [MH]$^+$ |

TABLE 7-continued

Amide couplings

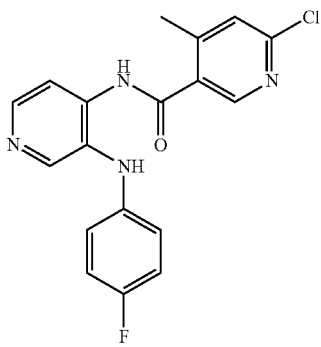 [SMILES: Cc1cc(Cl)ncc1C(=O)Nc1ccncc1Nc1ccc(F)cc1]

| Int | Structure | Name | Intermediate(s), Form, Yield, LCMS, HPLC |
|---|---|---|---|
| 108 | 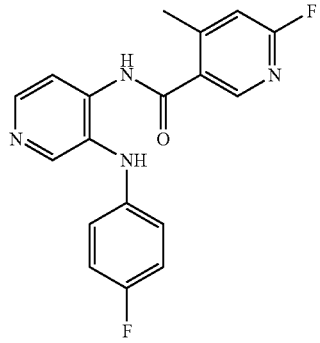 | 6-Chloro-N-{3-[(4-fluorophenyl)amino]pyridin-4-yl}-4-methylpyridine-3-carboxamide | From Intermediate 20 used crude LCMS (ES$^+$): 357.3 [MH]$^+$ |
| 109 | | 6-Fluoro-N-{3-[(4-fluorophenyl)amino]pyridin-4-yl}-4-methylpyridine-3-carboxamide | From Intermediate 20 Pale yellow solid Yield 1.11 g, 66.0% LCMS (ES$^+$): 341.0 [MH]$^+$ |
| 110 | 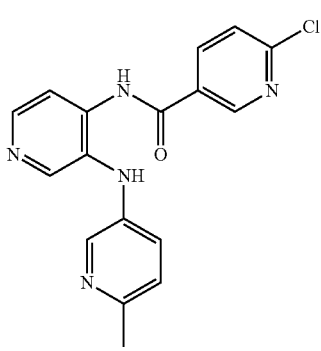 [SMILES: Cc1ccc(Nc2cnccc2NC(=O)c2ccc(Cl)nc2)cn1] | 6-Chloro-N-{3-[(6-methylpyridin-3-yl)amino]pyridin-4-yl}pyridine-3-carboxamide | From Intermediate 23 Dark oil used crude LCMS (ES$^+$): 340.0 [MH]$^+$ |

TABLE 7-continued

Amide couplings

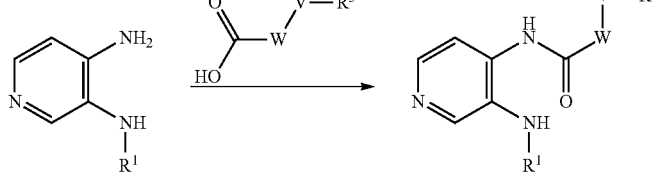

| Int | Structure | Name | Intermediate(s), Form, Yield, LCMS, HPLC |
|---|---|---|---|
| 111 | 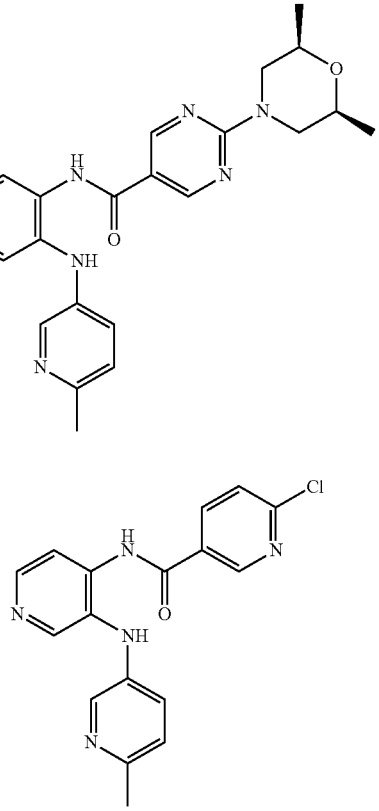 | 2-[(2R,6S)-2,6-Dimethylmorpholin-4-yl]-N-{3-[(6-methylpyridin-3-yl)amino]pyridin-4-yl}pyrimidine-5-carboxamide | From Intermediates 23 and 41<br>Dark orange oil<br>used crude<br>LCMS (ES$^+$): 420.1 [MH]$^+$ |
| 112 | 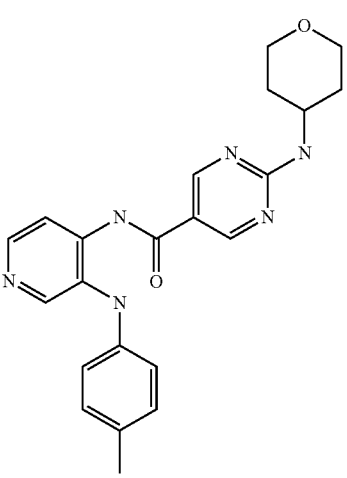 | 6-Chloro-N-{3-[(5-methylpyridin-2-yl)amino]pyridin-4-yl}pyridine-3-carboxamide | From Intermediate 24<br>Dark oil<br>used crude<br>LCMS (ES$^+$): 340.0 [MH]$^+$ |
| 113 | 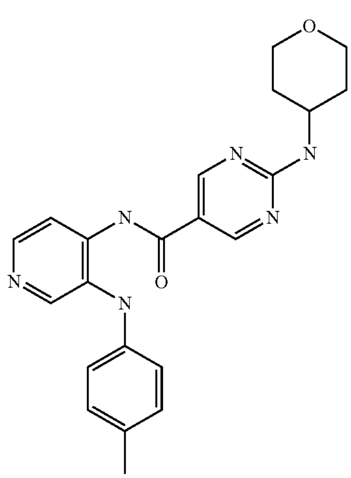 [SMILES: Cc1ccc(Nc2cnccc2NC(=O)c2cnc(NC3CCOCC3)nc2)cc1] | N-{3-[(4-Methylphenyl)amino]pyridin-4-yl}-2-[(oxan-4-yl)amino]pyrimidine-5-carboxamide | From Intermediates 21 and 38<br>Dark oil<br>used crude<br>LCMS (ES$^+$): 405.0 [MH]$^+$ |

TABLE 7-continued

Amide couplings

| Int | Structure | Name | Intermediate(s), Form, Yield, LCMS, HPLC |
|---|---|---|---|
| 114 | 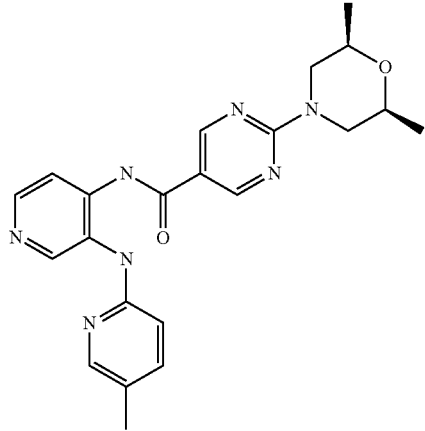 [SMILES: Cc1ccc(Nc2cnccc2NC(=O)c2cnc(N3C[C@@H](C)O[C@@H](C)C3)nc2)nc1] | 2-[(2R,6S)-2,6-Dimethylmorpholin-4-yl]-N-{3-[(5-methylpyridin-2-yl)amino]pyridin-4-yl}pyrimidine-5-carboxamide | From Intermediates 24 and 41<br>Orange oil<br>used crude<br>LCMS (ES+): 420.0 [MH]+ |
| 115 | 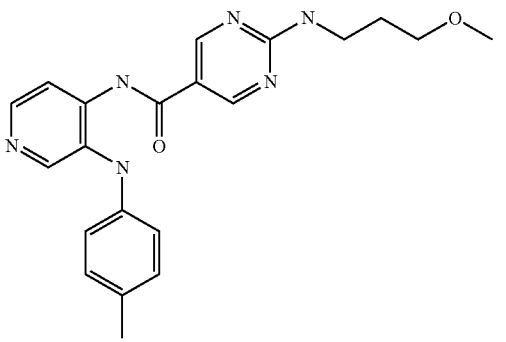 [SMILES: COCCCNc1ncc(C(=O)Nc2ccncc2Nc2ccc(C)cc2)cn1] | 2-[(3-Methoxypropyl)amino]-N-{3-[(4-methylphenyl)amino]pyridin-4-yl}pyrimidine-5-carboxamide | From Intermediates 21 and 48<br>Dark oil<br>used crude<br>LCMS (ES+): 393.1 [MH]+ |
| 116 | 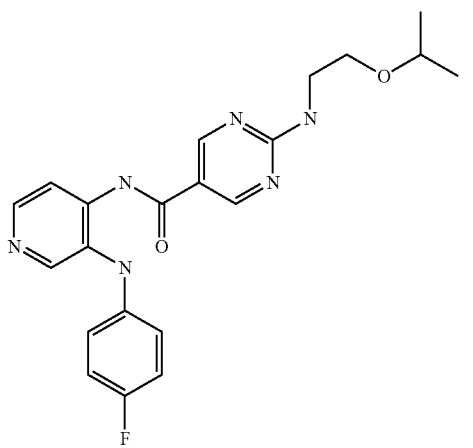 [SMILES: CC(C)OCCNc1ncc(C(=O)Nc2ccncc2Nc2ccc(F)cc2)cn1] | N-{3-[(4-Fluorophenyl)amino]pyridin-4-yl}-2-{[2-(propan-2-yloxy)ethyl]amino}pyrimidine-5-carboxamide | From Intermediates 20 and 49<br>Dark oil<br>used crude<br>LCMS (ES+): 411.0 [MH]+ |

TABLE 7-continued

Amide couplings

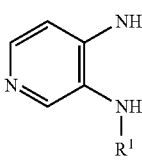

| Int | Structure | Name | Intermediate(s), Form, Yield, LCMS, HPLC |
|---|---|---|---|
| 117 | 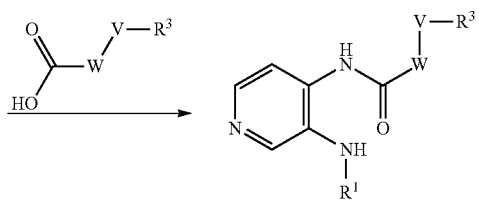 | N-{3-[(4-Methylphenyl)amino]pyridin-4-yl}-2-{[2-(propan-2-yloxy)ethyl]amino}pyrimidine-5-carboxamide | From Intermediates 21 and 49<br>Dark oil<br>used crude<br>LCMS (ES+): 407.1 [MH]+ |
| 118 | 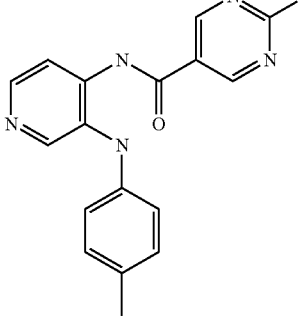 | N-{3-[(4-Fluorophenyl)amino]pyridin-4-yl}-2-(4-methyl-3-oxopiperazin-1-yl)pyrimidine-5-carboxamide | From Intermediates 20 and 50<br>Dark oil<br>used crude<br>LCMS (ES+): 422.1 [MH]+ |
| 119 | 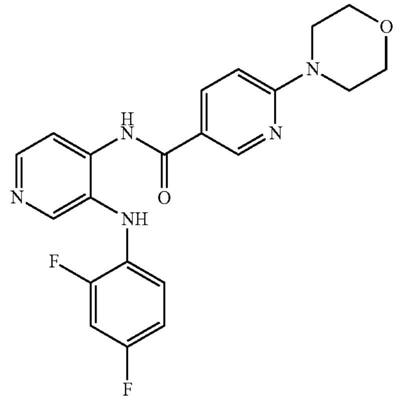 [SMILES: O=C(Nc1ccncc1Nc1ccc(F)cc1F)c1ccc(N2CCOCC2)nc1] | N-{3-[(2,4-Difluorophenyl)amino]pyridin-4-yl}-6-(morpholin-4-yl)pyridine-3-carboxamide | From Intermediate 25<br>Orange oil<br>used crude<br>LCMS (ES+): 412.0 [MH]+ |

TABLE 7-continued

Amide couplings

| Int | Structure | Name | Intermediate(s), Form, Yield, LCMS, HPLC |
|-----|-----------|------|-------------------------------------------|
| 120 | 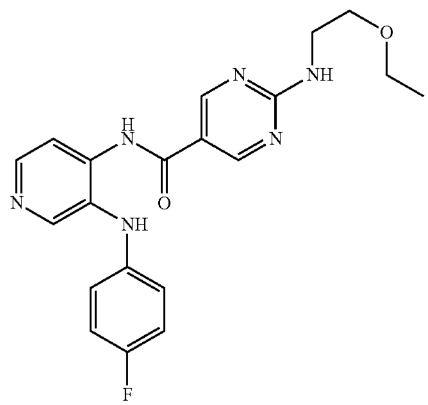 [SMILES: CCOCCNc1ncc(C(=O)Nc2ccncc2Nc2ccc(F)cc2)cn1] | 2-[(2-Ethoxyethyl)amino]-N-{3-[(4-fluorophenyl)amino]pyridin-4-yl}pyrimidine-5-carboxamide | From Intermediate 20 and 47<br>Orange oil<br>used crude<br>LCMS (ES$^+$): 397.1 [MH]$^+$ |
| 121 | 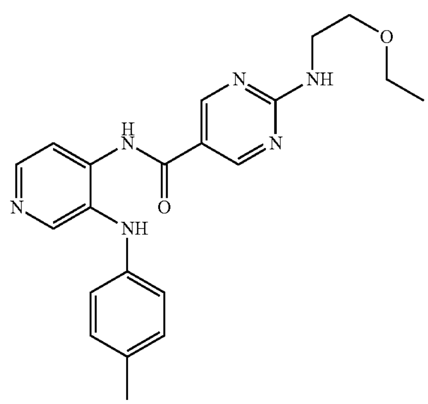 [SMILES: CCOCCNc1ncc(C(=O)Nc2ccncc2Nc2ccc(C)cc2)cn1] | 2-[(2-Ethoxyethyl)amino]-N-{3-[(4-methylphenyl)amino]pyridin-4-yl}pyrimidine-5-carboxamide | From Intermediate 21 and 47<br>Dark oil<br>used crude<br>LCMS (ES$^+$): 393.1 [MH]$^+$ |
| 122 | 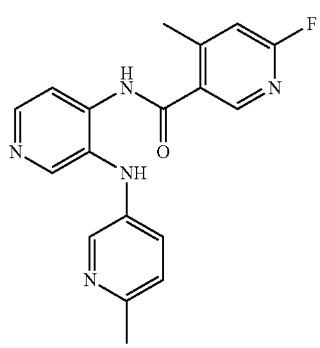 [SMILES: Cc1ccc(Nc2cnccc2NC(=O)c2cnc(F)cc2C)cn1] | 6-Fluoro-4-methyl-N-{3-[(6-methylpyridin-3-yl)amino]pyridin-4-yl}pyridine-3-carboxamide | From Intermediate 23<br>Dark oil<br>used crude<br>LCMS (ES$^+$): 338.0 [MH]$^+$ |

TABLE 7-continued

Amide couplings

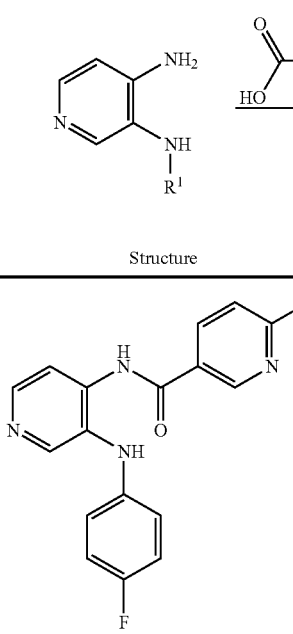

| Int | Structure | Name | Intermediate(s), Form, Yield, LCMS, HPLC |
|---|---|---|---|
| 123 | 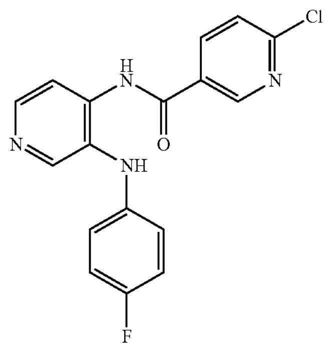 [SMILES: O=C(Nc1ccncc1Nc1ccc(F)cc1)c1ccc(Cl)nc1] | 6-Chloro-N-{3-[(4-fluorophenyl)amino]pyridin-4-yl}pyridine-3-carboxamide | From Intermediate 20<br>Yellow solid<br>Yield 1.06 g, 63.0%<br>LCMS (ES$^+$): 342.9 [MH]$^+$<br>HPLC: Rt 4.86 min, 91.2% purity |

Intermediate 124

N-{3-[(4-Fluorophenyl)amino]pyridin-4-yl}-2,4-dimethyl-6-(morpholin-4-yl)pyridine-3-carboxamide

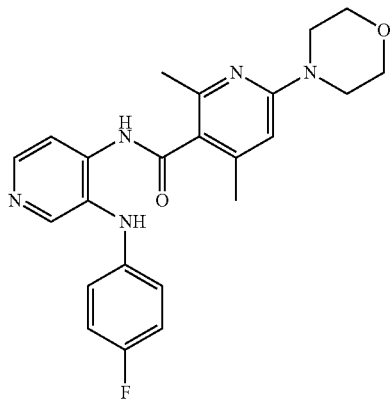 [SMILES: Cc1cc(N2CCOCC2)nc(C)c1C(=O)Nc1ccncc1Nc1ccc(F)cc1]

Intermediate 125

N-{3-[(4-Fluorophenyl)amino]pyridin-4-yl}-6-(oxan-4-yl)pyridazine-3-carboxamide

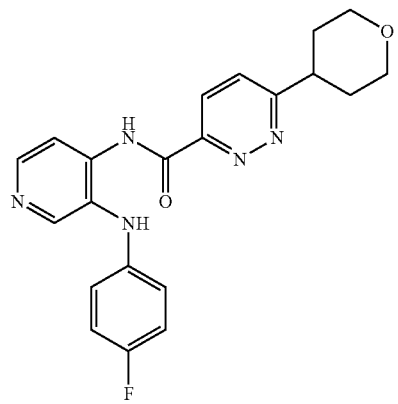 [SMILES: O=C(Nc1ccncc1Nc1ccc(F)cc1)c1ccc(C2CCOCC2)nn1]

Intermediate 96 (crude) was dissolved in NMP (2 mL) and morpholine (1.70 mL, 19.7 mmol) and Et$_3$N (708 uL, 5.08 mmol) were added. The reaction mixture was heated at 190 t in a microwave reactor for 30 min and partitioned between EtOAc (50 mL) and water (50 mL). The organic fraction was washed with water (50 mL), brine (50 mL), dried (MgSO$_4$), concentrated in vacuo and purified by column chromatography to give the title compound (783 mg, 47.1%) as a yellow solid; LCMS (ES$^+$): 422.0 [MH]$^+$, HPLC: Rt: 3.99 min, 83.2% purity.

Intermediate 80 (220 mg, 0.562 mmol) was dissolved in MeOH (10 mL), Pd/C (cat) was added and the reaction mixture was stirred under hydrogen for 2 h. The reaction mixture was filtered through Celite and concentrated in vacuo to give the crude title compound which was used without purification. LCMS (ES$^+$): 394.2 [MH]$^+$.

Intermediate 126

1-{5-[3-(4-Fluorophenyl)-3H-imidazo[4,5-c]pyridin-2-yl]pyridin-2-yl}piperazine Trihydrochloride

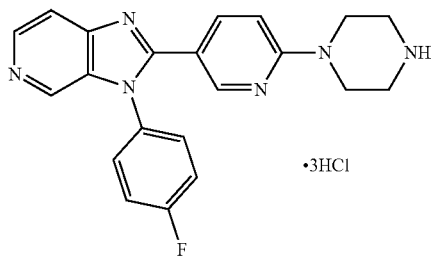 [SMILES: Fc1ccc(-n2c(-c3ccc(N4CCNCC4)nc3)nc3ccncc32)cc1]

Intermediate 126 was prepared similarly to Example 50, using Intermediate 2 instead of Intermediate 1, to give the title compound (684 mg, 100%) as a white solid. LCMS (ES$^+$): 375.1 [MH]$^+$.

Intermediate 127

2-Chloro-5-[3-(4-fluorophenyl)-3H-imidazo[4,5-c]pyridin-2-yl]pyridine

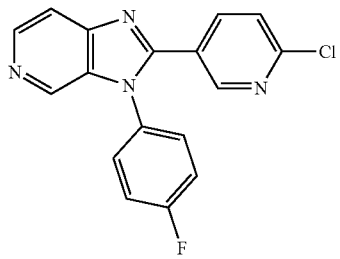 [SMILES: Fc1ccc(-n2c(-c3ccc(Cl)nc3)nc3ccncc32)cc1]

Intermediate 2 (1.00 g, 4.01 mmol) and 2-chloro-5-pyridinecarboxaldehyde (682 mg, 4.82 mmol) were dissolved in EtOH (8 mL) and Na$_2$S$_2$O$_4$ (2.79 g, 16.1 mmol) was added. The reaction mixture was heated in a microwave reactor at 160° C. for 1 h, diluted with water (25 mL) and NaHCO$_3$ (25 mL) and extracted into DCM (3×50 mL). The combined organic fractions were dried (MgSO$_4$) and concentrated in vacuo. The residue was purified by column chromatography to give the title compound (375 mg, 28.8%) as a yellow oil. LCMS (ES$^+$): 325.1 [MH]$^+$.

Intermediate 128

2-Chloro-5-[3-(4-chlorophenyl)-3H-imidazo[4,5-c]pyridin-2-yl]pyridine

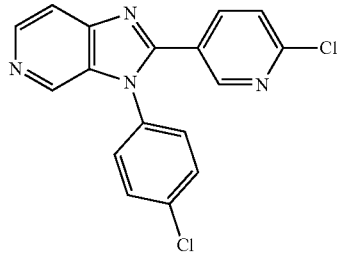 [SMILES: Clc1ccc(-n2c(-c3ccc(Cl)nc3)nc3ccncc32)cc1]

Intermediate 128 was prepared similarly to Intermediate 127, using Intermediate 1 instead of Intermediate 2, to give the title compound (81.0 mg, 8.41%) as a yellow solid. LCMS (ES$^+$): 341.1 [MH]$^+$. HPLC: Rt: 5.10 min, 97.0% purity.

Intermediate 129

1-{5-[3-(4-Fluorophenyl)-3H-imidazo[4,5-c]pyridin-2-yl]pyridin-2-yl}-1,4-diazepane

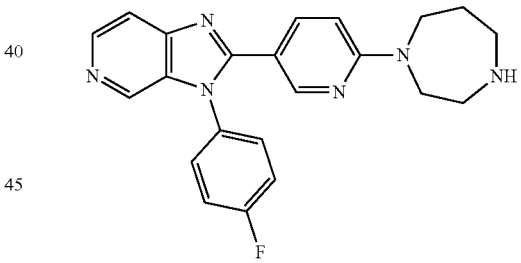

Intermediate 127 (375 mg, 1.15 mmol) and homopiperazine (578 mg, 5.77 mmol) were dissolved in DMA (6 mL) and the reaction mixture was heated in a microwave reactor at 1800° C. for 30 min and concentrated in vacuo. The residue was partitioned between DCM (50 mL) and sat. aq. Na$_2$CO$_3$ (50 mL) and the organic fraction dried (MgSO$_4$) and concentrated in vacuo to give the title compound (410 mg, 91.5%) as a red oil. LCMS (ES$^+$): 389.2 [MH]$^+$.

Intermediates 130-133

Intermediates 130-133 were prepared similarly to Example 1, by cyclisation of Intermediates 94, 99, 104 and 108; see Table 8 below.

TABLE 8

Cyclisation of Intermediates 94, 99, 104 and 108

| Ex | Structure | Name | Intermediates(s), Form, Yield, LCMS, HPLC |
|---|---|---|---|
| 130 | 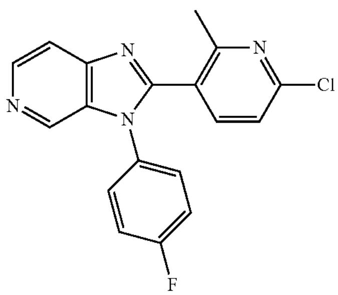 [SMILES: Cc1nc(Cl)ccc1-c1nc2ccncc2n1-c1ccc(F)cc1] | 6-Chloro-3-[3-(4-fluorophenyl)-3H-imidazo[4,5-c]pyridin-2-yl]-2-methylpyridine | From Intermediate 94<br>Pale brown gum<br>Yield 123 mg, 29.5%<br>LCMS (ES+): 339.1 [MH]+<br>HPLC: Rt 4.64 min, 74.0% purity |
| 131 | 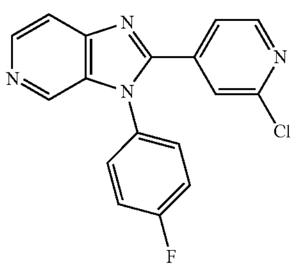 [SMILES: Fc1ccc(-n2c(-c3ccnc(Cl)c3)nc3ccncc32)cc1] | 2-Chloro-4-[3-(4-fluorophenyl)-3H-imidazo[4,5-c]pyridin-2-yl]pyridine | From Intermediate 99<br>Yellow solid<br>Yield 397 mg, 68.9%<br>LCMS (ES+): 325.1 [MH]+<br>HPLC: Rt 4.48 min, 80.2% purity |
| 132 | 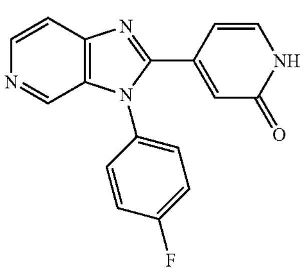 [SMILES: O=c1cc(-c2nc3ccncc3n2-c2ccc(F)cc2)cc[nH]1] | 4-[3-(4-Fluorophenyl)-3H-imidazo[4,5-c]pyridin-2-yl]-1,2-dihydropyridin-2-one | From Intermediate 104<br>Pale pink solid<br>Yield 172 mg, 22.7%<br>LCMS (ES+): 307.2 [MH]+<br>HPLC: Rt 3.42 min, 99.7% purity |
| 133 | 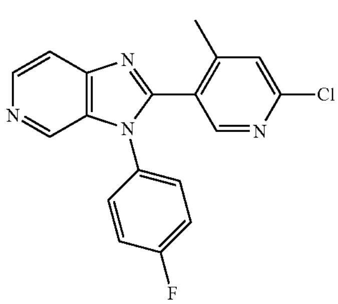 [SMILES: Cc1cc(Cl)ncc1-c1nc2ccncc2n1-c1ccc(F)cc1] | 2-Chloro-5-[3-(4-fluorophenyl)-3H-imidazo[4,5-c]pyridin-2-yl]-4-methylpyridine | From Intermediate 108<br>Yellow gum<br>Yield 218 mg, 63.1%<br>LCMS (ES+): 338.7 [MH]+ |

Intermediate 134

1-(4-Chlorophenyl)-1H-pyrrolo[2,3-c]pyridine

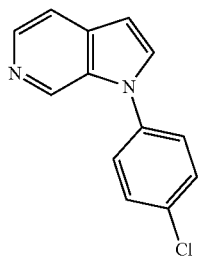 [SMILES: Clc1ccc(-n2ccc3ccncc32)cc1]

6-Azaindole (5.00 g, 42.3 mmol) was dissolved in DMF (150 mL) under nitrogen and 1-chloro-4-iodo-benzene (12.1 g, 50.8 mmol), N,N-dimethylethylenediamine (911 uL, 8.46 mmol), $K_3PO_4$ (18.9 g, 88.9 mmol) and CuI (806 mg, 4.23 mmol) were added. The reaction mixture was heated at 150° C. for 18 h. The reaction mixture was filtered and the filtrate was concentrated in vacuo. The residue was suspended in 1M aq. $Na_2CO_3$ (250 mL) and extracted into DCM (2×250 mL). The combined organic fractions were dried ($MgSO_4$) and concentrated in vacuo. The residue was purified by column chromatography to give the title compound as a yellow solid (8.58 g, 88.6%). LCMS ($ES^+$): 229.1 $[MH]^+$. HPLC: Rt 4.48 min, 98.6% purity.

Intermediate 135-138

Intermediates 135-138 were prepared similarly to Intermediate 134, by arylation of 6-azaindole with the appropriate aryl or heteroaryl iodide or bromide; see Table 9 below.

TABLE 9

Arylations of 6-azaindole

| Ex | Structure | Name | Intermediate(s), Form, Yield, LCMS, HPLC |
|---|---|---|---|
| 135 | 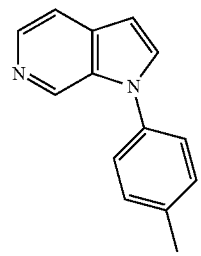 [SMILES: Cc1ccc(-n2ccc3ccncc32)cc1] | 1-(4-Methylphenyl)-1H-pyrrolo[2,3-c]pyridine | Green gum<br>Yield 800 mg, 45.4%<br>LCMS ($ES^+$): 209.1 $[MH]^+$<br>HPLC: Rt 4.65 min, 99.7% purity. |
| 136 | 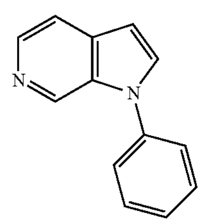 [SMILES: c1ccc(-n2ccc3ccncc32)cc1] | 1-Phenyl-1H-pyrrolo[2,3-c]pyridine | Green gum<br>Yield 890 mg, 54.0%<br>LCMS ($ES^+$): 195.1 $[MH]^+$<br>HPLC: Rt 4.19 min, 99.6% purity. |

TABLE 9-continued

Arylations of 6-azaindole

| Ex | Structure | Name | Intermediate(s), Form, Yield, LCMS, HPLC |
|---|---|---|---|
| 137 | 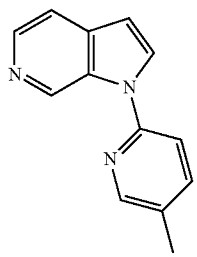 [SMILES: Cc1ccc(-n2ccc3ccncc32)nc1] | 5-Methyl-2-{1H-pyrrolo[2,3-c]pyridin-1-yl}pyridine | Light yellow solid<br>Yield 113 mg, 6.38%<br>LCMS (ES$^+$): 210.1 [MH]$^+$<br>HPLC: Rt 4.45 min, 100% purity. |
| 138 | 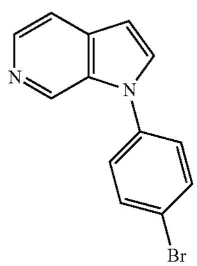 [SMILES: Brc1ccc(-n2ccc3ccncc32)cc1] | 1-(4-Bromophenyl)-1H-pyrrolo[2,3-c]pyridine | Green solid<br>Yield 1.14 g, 24.7%<br>LCMS (ES$^+$): 273.0 [MH]$^+$<br>HPLC: Rt 4.78 min, 98.5% purity. |

Intermediate 139

1-[(4-Iodophenyl)carbonyl]-4-methylpiperazine

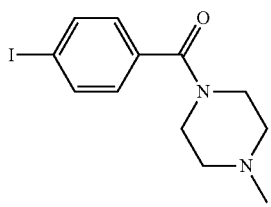 [SMILES: CN1CCN(C(=O)c2ccc(I)cc2)CC1]

4-Iodobenzoic acid (500 mg, 2.02 mmol) and DMF (50 uL) were dissolved in DCM (24 mL), oxalyl chloride (182 uL, 2.12 mmol) was added drop-wise and the reaction mixture was stirred for 30 min. DIPEA (421 uL, 2.42 mmol) and a solution of N-methylpiperazine (222 mg, 2.22 mmol) in DCM (1 mL) were added and the reaction mixture was stirred for 30 min, washed with sat. aq. NaHCO$_3$ (2×75 mL), dried (MgSO$_4$) and concentrated in vacuo to give the title compound (660 mg, 99.2%) as a yellow solid. LCMS (ES$^+$): 331.0 [MH]$^+$. HPLC: Rt 4.05 min, 99.6% purity.

Intermediate 140

4-(5-Bromopyrimidin-2-yl)piperazin-2-one

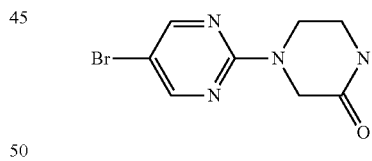

5-Bromo-2-chloropyrimidine (750 mg, 3.88 mmol), DIPEA (878 uL, 5.04 mmol) and piperazin-2-one (427 mg, 4.26 mmol) were dissolved in MeCN (20 mL). The reaction mixture was heated at 95 C for 1 h then allowed to cool to RT overnight. The resulting solid was collected by filtration, washed with water (2×20 mL) to give the title compound (546 mg, 54.8%) as a white solid. LCMS (ES$^+$): 257.1 and 259.1 [MH]$^+$. HPLC: Rt 4.68 min, 98.6% purity.

Intermediate 141-142

Intermediates 141-142 were prepared similarly to Intermediate 140, by coupling of 5-bromo-2-chloropyrimidine with the appropriate amine; see Table 10 below.

TABLE 10

SNAr with 5-bromo-2-chloropyrimidine

| Ex | Structure | Name | Intermediate(s), Form, Yield, LCMS, HPLC |
|---|---|---|---|
| 141 | 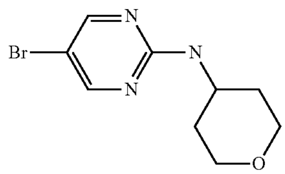 [SMILES: Brc1cnc(NC2CCOCC2)nc1] | 5-Bromo-N-(oxan-4-yl)pyrimidin-2-amine | White solid<br>Yield 645 mg, 48.4%<br>LCMS (ES$^+$): 258.0 [MH]$^+$ |
| 142 | 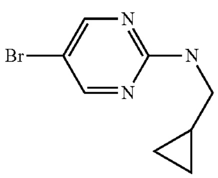 [SMILES: Brc1cnc(NCC2CC2)nc1] | 5-Bromo-N-(cyclopropylmethyl)pyrimidin-2-amine | Light yellow solid<br>Yield 476 mg, 80.7%<br>LCMS (ES$^+$): 228.1 [MH]$^+$<br>HPLC: Rt 6.48 min, 83.9% purity. |

Intermediate 143

4-(5-Bromo-4-methylpyridin-2-yl)morpholine

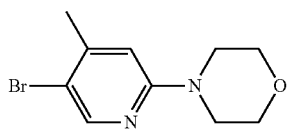

5-Bromo-2-fluoro-4-methylpyridine (1.00 g, 5.26 mmol) and morpholine (1.38 mL, 15.8 mmol) were dissolved in MeCN (3.0 mL) and the reaction mixture heated by microwave reactor at 140-160° C. for 1.5 h. The reaction mixture was dilute d with EtOAc (40 mL), washed with sat. aq. NaHCO$_3$ (40 mL), dried (MgSO$_4$) and the solvents removed in vacuo to give the title compound (1.20 g, 88.7%) as a white solid. LCMS (ES$^+$): 257.0 [MH]$^+$. HPLC: Rt 4.40 min, 95.1% purity.

Intermediate 144

1-Cyclopropyl-4-iodo-1,2-dihydropyridin-2-one

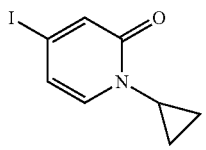 [SMILES: O=c1cc(I)ccn1C1CC1]

4-Iodo-1,2-dihydropyridin-2-one (1.00 g, 4.52 mmol), copper (II) acetate (879 mg, 4.84 mmol), 4,4-dipyridyl (756 mg, 4.84 mmol), cyclopropylboronic acid (875 mg, 10.2 mmol) and Na$_2$CO$_3$ (1.09 g, 10.3 mmol) in DCE (40 mL) was stirred at 70° C. for 18 h. The reaction was quenched with sat. NH$_4$Cl (20 mL) and water (50 mL) and extracted with DCM (2×50 mL), dried MgSO$_4$ and concentrated in vacuo. The crude material was purified by column chromatography to give the title compound (585 mg, 49.5%) as a yellow oil. LCMS (ES$^+$): 262.0 [MH]$^+$.

Intermediate 145

4-[(5-Bromopyridin-2-yl)methyl]morpholine

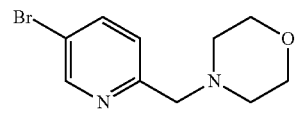

5-Bromo-pyridine-2-carbaldehyde (1.00 g, 5.38 mmol) and morpholine (464 uL, 5.38 mmol) were dissolved in DCM (20 mL) and NaBH(OAc)$_3$ (1.71 g, 8.06 mmol) was added. The reaction mixture was stirred at RT for 4 d then heated at 50° C. for 7 h. Morpholine (464 uL, 5.38 mmol) and NaBH(OAc)$_3$ (1.71 g, 8.06 mmol) were added and the reaction was heated at 50° C. for 16 h. Water (50 mL) and sat. aq. Na$_2$CO$_3$ sol. (50 mL) were added and the aqueous fraction was then extracted with DCM (2×100 mL) dried (MgSO$_4$), filtered and the solvent removed in vacuo. The crude material was purified by column chromatography to give the title compound (1.31 g, 94.8%) as a yellow oil. LCMS (ES$^+$): 257.0 [MH]$^+$.

Intermediate 146

4-Iodo-1-methyl-1,2-dihydropyridin-2-one

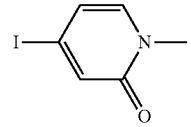

4-Iodo-1,2-dihydropyridin-2-one (500 mg, 2.26 mmol), MeI (296 uL, 4.75 mmol) and K₂CO₃ (688 mg, 4.98 mmol) were suspended in MeCN (20 mL) and stirred for 18 h. The reaction mixture was filtered and the solvents removed in vacuo. The residue was purified by column chromatography to give the title compound (411 mg, 77.3%) as a white solid. LCMS (ES⁺): 236.0 [MH]⁺. HPLC: Rt 4.48 min, 99.6% purity.

INTERMEDIATE 147

1-Ethyl-4-iodo-1,2-dihydropyridin-2-one

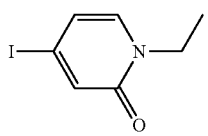

Intermediate 147 was prepared similarly to Intermediate 146, using ethyl iodide instead of methyl iodide, to give the title compound (347 mg, 61.6%) as a yellow gum. LCMS (ES⁺): 250.0 [MH]⁺. HPLC: Rt 5.04 min, 96.0% purity.

INTERMEDIATE 148

6-Bromo-1-methyl-1,2-dihydropyridin-2-one

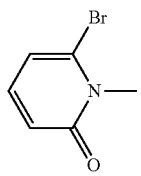

Intermediate 148 was prepared similarly to Intermediate 146, using 2-bromo-6-hydroxypyridine instead of 4-iodo-1,2-dihydropyridin-2-one, to give the title compound (468 mg, 86.6%) as an off white solid. LCMS (ES⁺): 188.1 and 190.1 [MH]⁺. HPLC: Rt 4.17 min, 98.4% purity.

Example 1

3-[3-(4-Chlorophenyl)-3H-imidazo[4,5-c]pyridin-2-yl]pyridine

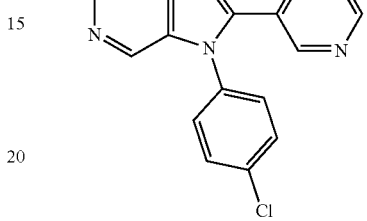

Intermediate 66 (297 mg, 0.914 mmol) was dissolved in AcOH (5 mL) and heated using a microwave reactor at 100° C. for 15 min, diluted with water (50 mL), basified with Na₂CO₃ and extracted into DCM (3×50 mL). The combined organic fractions were dried (MgSO₄) and concentrated in vacuo. The residue was purified by column chromatography to give the title compound as a white solid (139 mg, 49.5%). HRMS (ESI⁺) calcd for [MH]⁺ of C₁₇H₁₁ClN₄ 307.0750 found 307.0748. HPLC: Rt 4.22 min, 99.8% purity.

Examples 2-43

Examples 2-43 were prepared similarly to Example 1, by cyclisation of Intermediates 67-79, 81-86, 88-93, 95, 100-103, 105-106, 114-121, 124 and 125; see Table 11 below.

TABLE 11

Cyclisation of Intermediates 67-79, 81-86, 88-93, 95, 100-103, 105-106, 114-121, 124 and 125

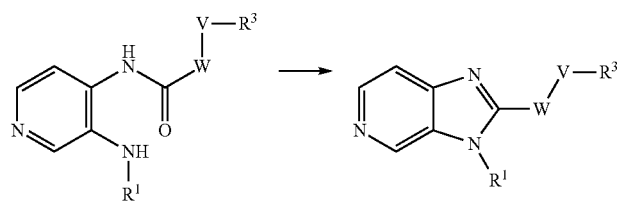

| Ex | Structure | Name | Intermediate(s), Form, Yield, LCMS, HPLC |
|---|---|---|---|
| 2 | 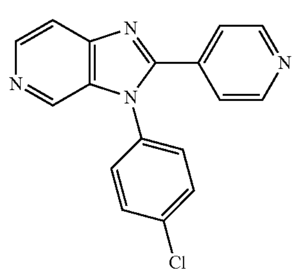 [SMILES: Clc1ccc(-n2c(-c3ccncc3)nc3ccncc32)cc1] | 4-[3-(4-Chlorophenyl)-3H-imidazo[4,5-c]pyriidn-2-yl]pyridine | From Intermediate 67<br>Light pink solid<br>Yield 109 mg, 52.7%<br>HRMS (ESI⁺) calcd for [MH]⁺ of C₁₇H₁₁ClN₄ 307.0750 found 307.0752.<br>HPLC: Rt 3.90 min, 99.8% purity |

TABLE 11-continued

Cyclisation of Intermediates 67-79, 81-86, 88-93, 95, 100-103, 105-106, 114-121, 124 and 125

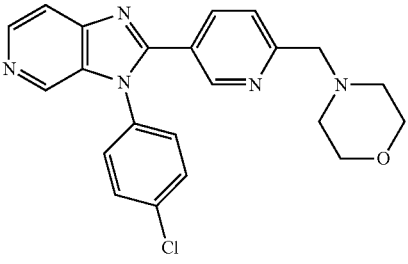 [SMILES: Clc1ccc(-n2c(-c3ccc(CN4CCOCC4)nc3)nc3ccncc32)cc1]

| Ex | Structure | Name | Intermediate(s), Form, Yield, LCMS, HPLC |
|---|---|---|---|
| 3 | 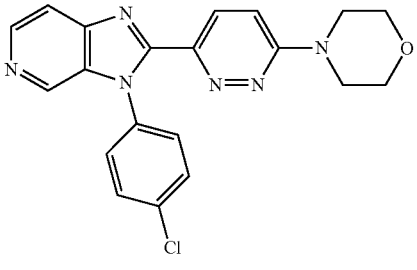 [SMILES: Clc1ccc(-n2c(-c3ccc(N4CCOCC4)nn3)nc3ccncc32)cc1] | 4-({5-[3-(4-Chlorophenyl)-3H-imidazo[4,5-c]pyridin-2-yl]pyridin-2-yl}methyl)morpholine | From Intermediate 68<br>White solid<br>Yield 105 mg, 38.6%<br>HRMS (ESI$^+$) calcd for [MH]$^+$ of $C_{22}H_{20}ClN_5O$ 406.1435 found 406.1428.<br>HPLC: Rt 3.65 min, 100% purity |
| 4 | 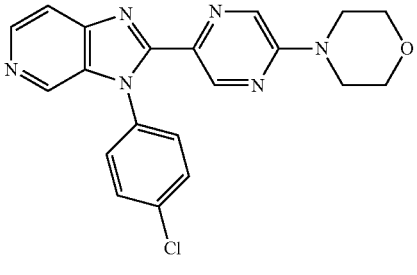 [SMILES: Clc1ccc(-n2c(-c3cnc(N4CCOCC4)cn3)nc3ccncc32)cc1] | 4-{6-[3-(4-Chlorophenyl)-3H-imidazo[4,5-c]pyridin-2-yl]pyridazin-3-yl}morpholine | From Intermediate 69<br>White solid<br>Yield 89.9 mg, 18.8%<br>HRMS (ESI$^+$) calcd for [MH]$^+$ of $C_{20}H_{17}ClN_6O$ 393.1230 found 393.1234.<br>HPCL: Rt 4.71 min, 98.4% purity |
| 5 | 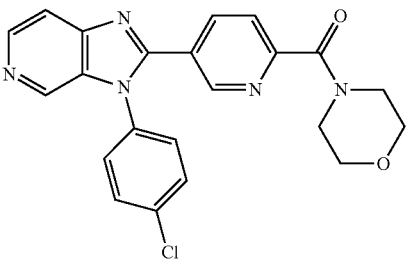 | 4-{5-[3-(4-Chlorophenyl)-3H-imidazo[4,5-c]pyridin-2-yl]pyrazin-2-yl}morpholine | From Intermediate 70<br>White solid<br>Yield 114 mg, 18.9%<br>HRMS (ESI$^+$) calcd for [MH]$^+$ of $C_{20}H_{17}ClN_6O$ 393.1230 found 393.1234.<br>HPLC: Rt 4.79 min, 100% purity |
| 6 | 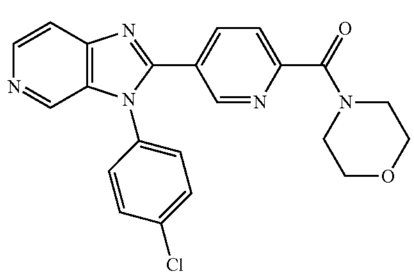 [SMILES: O=C(c1ccc(-c2nc3ccncc3n2-c2ccc(Cl)cc2)cn1)N1CCOCC1] | 4-({5-[3-(4-Chlorophenyl)-3H-imidazo[4,5-c]pyridin-2-yl]pyridin-2-yl}carbonyl)morpholine | From Intermediate 71<br>White solid<br>Yield 170 mg, 40.5%<br>HRMS (ESI$^+$) calcd for [MH]$^+$ of $C_{22}H_{18}ClN_5O_2$ 420.1227 found 420.1228.<br>HPLC: Rt 4.03 min, 100% purity |

TABLE 11-continued

Cyclisation of Intermediates 67-79, 81-86, 88-93, 95, 100-103, 105-106, 114-121, 124 and 125

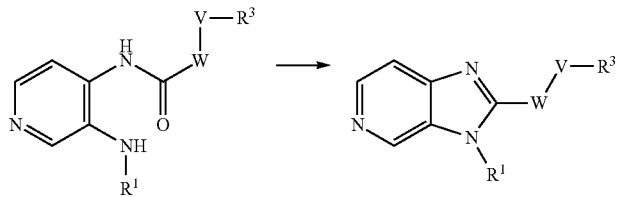

| Ex | Structure | Name | Intermediate(s), Form, Yield, LCMS, HPLC |
|---|---|---|---|
| 7 | 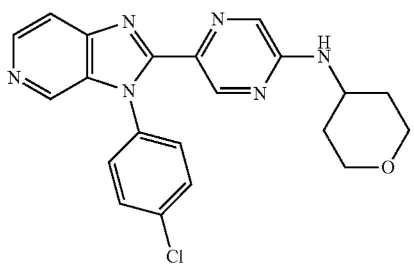 [SMILES: Clc1ccc(-n2c(-c3cnc(NC4CCOCC4)cn3)nc3ccncc32)cc1] | 5-[3-(4-Chlorophenyl)-3H-imidazo[4,5-c]pyridin-2-yl]-N-(oxan-4-yl)pyrazin-2-amine | From Intermediate 72<br>Yellow solid<br>Yield 50.0 mg, 30.0%<br>HRMS (ES$^+$) calcd for [MH]$^+$ of $C_{21}H_{19}ClN_6O$ 407.1387 found 407.1380.<br>HPLC: Rt 4.86 min, 100% purity |
| 8 | 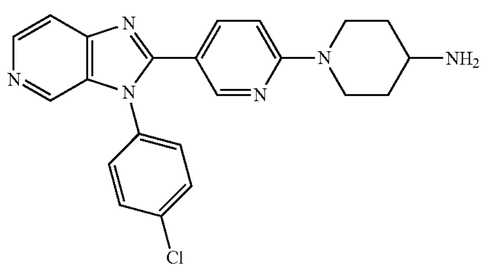 [SMILES: NC1CCN(c2ccc(-c3nc4ccncc4n3-c3ccc(Cl)cc3)cn2)CC1] | 1-{5-[3-(4-Chlorophenyl)-3H-imidazo[4,5-c]pyridin-2-yl]pyridin-2-yl}piperidin-4-amine | From Intermediate 73<br>White solid<br>Yield 24.2 mg, 38.7%<br>HRMS (ESI$^+$) calcd for [MH]$^+$ of $C_{22}H_{21}ClN_6$ 405.1594 found 405.1591.<br>HPLC: Rt 3.52 min, 100% purity |
| 9 | 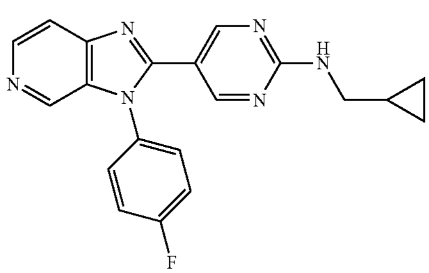 [SMILES: Fc1ccc(-n2c(-c3cnc(NCC4CC4)nc3)nc3ccncc32)cc1] | N-(Cyclopropylmethyl)-5-[3-(4-fluorophenyl)-3H-imidazo[4,5-c]pyridin-2-yl]pyrimidin-2-amine | From Intermediate 74<br>White solid<br>Yield 24.6 mg, 8.28%<br>HRMS (ESI$^+$) calcd for [MH]$^+$ of $C_{20}H_{17}FN_6$ 361.1577 found 361.1594.<br>HPLC: Rt 5.01 min, 97.0% purity |
| 10 | 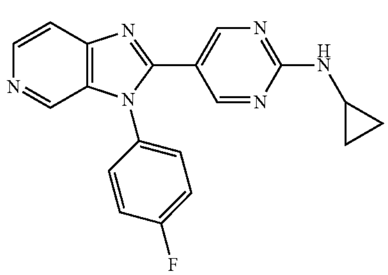 [SMILES: Fc1ccc(-n2c(-c3cnc(NC4CC4)nc3)nc3ccncc32)cc1] | N-Cyclopropyl-5-[3-(4-fluorophenyl)-3H-imidazo[4,5-c]pyridin-2-yl]pyrimidin-2-amine | From Intermediate 75<br>White solid<br>Yield 30.9 mg, 4.93%<br>HRMS (ESI$^+$) calcd for [MH]$^+$ of $C_{19}H_{15}FN_6$ 347.1420 found 347.1422.<br>HPLC: Rt 4.46 min, 99.6% purity |

TABLE 11-continued

Cyclisation of Intermediates 67-79, 81-86, 88-93, 95, 100-103, 105-106, 114-121, 124 and 125

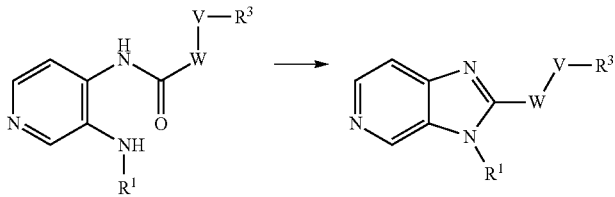

| Ex | Structure | Name | Intermediate(s), Form, Yield, LCMS, HPLC |
|---|---|---|---|
| 11 | 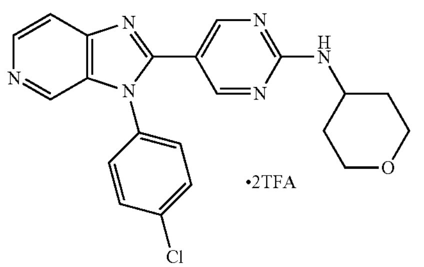 [SMILES: Clc1ccc(-n2c(-c3cnc(NC4CCOCC4)nc3)nc3ccncc32)cc1] | 5-[3-(4-Chlorophenyl)-3H-imidazo[4,5-c]pyridin-2-yl]-N-(oxan-4-yl)pyrimidin-2-amine; bis(trifluoroacetic acid) | From Intermediate 76<br>White solid<br>Yield 73.8 mg, 5.39%<br>HRMS (ESI$^+$) calcd for [MH]$^+$ of $C_{21}H_{19}ClN_6O$ 407.1387 found 407.1403.<br>HPLC: Rt 4.76 min, 100% purity |
| 12 | 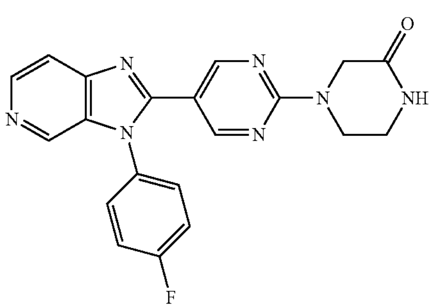 [SMILES: O=C1CN(c2ncc(-c3nc4ccncc4n3-c3ccc(F)cc3)cn2)CCN1] | 4-{5-[3-(4-Fluorophenyl)-3H-imidazo[4,5-c]pyridin-2-yl]pyrimidin-2-yl}piperazin-2-one | From Intermediate 77<br>White solid<br>Yield 104 mg, 9.29%<br>HRMS (ES$^+$) calcd for [MH]$^+$ of $C_{20}H_{16}FN_7O$ 390.1479 found 390.1481.<br>HPLC: Rt 4.01 min, 100% purity |
| 13 | 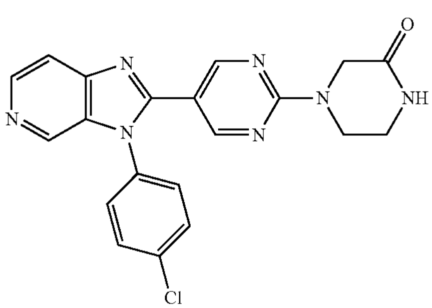 [SMILES: O=C1CN(c2ncc(-c3nc4ccncc4n3-c3ccc(Cl)cc3)cn2)CCN1] | 4-{5-[3-(4-Chlorophenyl)-3H-imidazo[4,5-c]pyridin-2-yl]pyrimidin-2-yl}piperazin-2-one | From Intermediate 78<br>White solid<br>Yield 97.1 mg, 14.2%<br>HRMS (ESI$^+$) calcd for [MH]$^+$ of $C_{20}H_{16}ClN_7O$ 406.1183 found 406.1185.<br>HPLC: Rt 4.25 min, 99.5% purity |
| 14 | 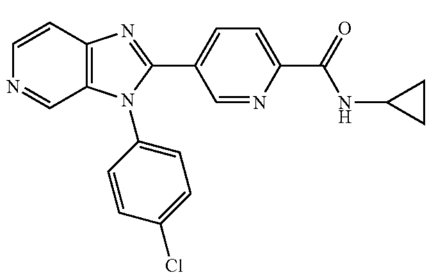 [SMILES: O=C(NC1CC1)c1ccc(-c2nc3ccncc3n2-c2ccc(Cl)cc2)cn1] | 5-[3-(4-Chlorophenyl)-3H-imidazo[4,5-c]pyridin-2-yl]-N-cyclopropylpyridine-2-carboxamide | From Intermediate 79<br>White solid<br>Yield 100 mg, 13.3%<br>HRMS (ESI$^+$) calcd for [MH]$^+$ of $C_{21}H_{16}ClN_5O$ 390.1122 found 390.1139.<br>HPLC: Rt 4.81 min, 100% purity |

TABLE 11-continued

Cyclisation of Intermediates 67-79, 81-86, 88-93, 95, 100-103, 105-106, 114-121, 124 and 125

| Ex | Structure | Name | Intermediate(s), Form, Yield, LCMS, HPLC |
|---|---|---|---|
| 15 | 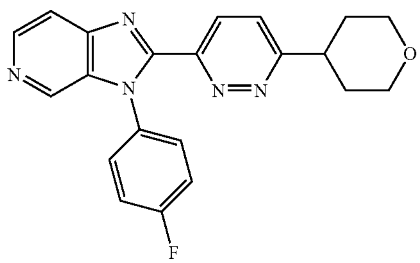 [SMILES: Fc1ccc(-n2c(-c3ccc(C4CCOCC4)nn3)nc3ccncc32)cc1] | 3-[3-(4-Fluorophenyl)-3H-imidazo[4,5-c]pyridin-2-yl]-6-(oxan-4-yl)pyridazine | From Intermediate 125 Off white solid Yield 14.0 mg, 6.63% HRMS (ESI$^+$) calcd for [MH]$^+$ of $C_{21}H_{18}FN_5O$ 376.1573 found 376.1575. HPLC: Rt 4.37 min, 98.4% purity |
| 16 | 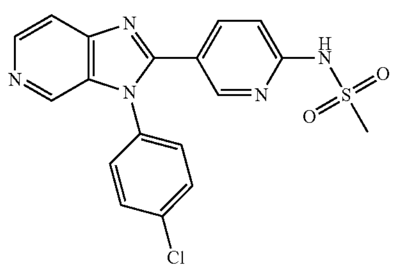 [SMILES: CS(=O)(=O)Nc1ccc(-c2nc3ccncc3n2-c2ccc(Cl)cc2)cn1] | N-{5-[3-(4-Chlorophenyl)-3H-imidazo[4,5-c]pyridin-2-yl]pyridin-2-yl}methanesulfonamide | From Intermediate 81 White solid Yield 163 mg, 48.8% HRMS (ESI$^+$) calcd for [MH]$^+$ of $C_{18}H_{14}ClN_5O_2S$ 400.0635 found 400.0631. HPLC: Rt 4.19 min, 100% purity |
| 17 | 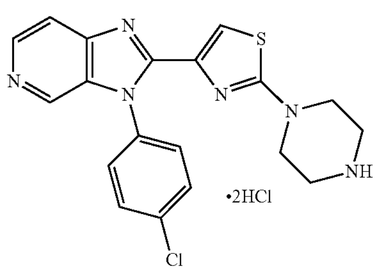 [SMILES: Clc1ccc(-n2c(-c3csc(N4CCNCC4)n3)nc3ccncc32)cc1] | 1-{4-[3-(4-Chlorophenyl)-3H-imidazo[4,5-c]pyridin-2-yl]-1,3-thiazol-2-yl}piperazine dihydrochloride | From Intermediate 82 Yellow solid Yield 47.3 mg, 17.3%* HRMS (ES$^+$) calcd for [MH]$^+$ of $C_{19}H_{17}ClN_6S$ 397.1002 found 397.1011. HPLC: Rt 3.44-3.55 min, 100% purity |
| 18 | 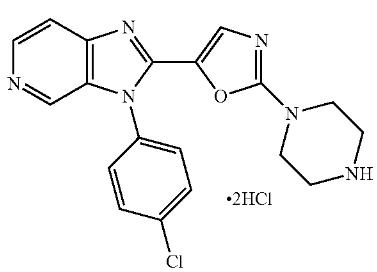 [SMILES: Clc1ccc(-n2c(-c3cnc(N4CCNCC4)o3)nc3ccncc32)cc1] | 1-{5-[3-(4-Chlorophenyl)-3H-imidazo[4,5-c]pyridin-2-yl]-1,3-oxazol-2-yl}piperazine dihydrochloride | From Intermediate 83 Orange solid Yield 58.0 mg, 11.8%* HRMS (ESI$^+$) calcd for [MH]$^+$ of $C_{19}H_{17}ClN_6O$ 381.1230 found 381.1241. HPLC: Rt 3.25 min, 100% purity |

TABLE 11-continued

Cyclisation of Intermediates 67-79, 81-86, 88-93, 95, 100-103, 105-106, 114-121, 124 and 125

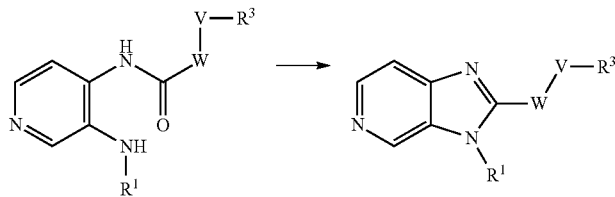

| Ex | Structure | Name | Intermediate(s), Form, Yield, LCMS, HPLC |
|---|---|---|---|
| 19 | 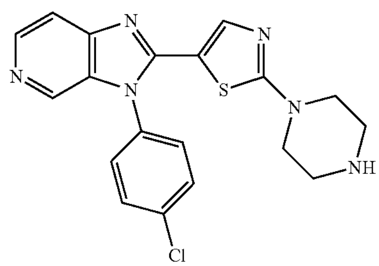 [SMILES: Clc1ccc(-n2c(-c3cnc(N4CCNCC4)s3)nc3ccncc32)cc1] | 1-{5-[3-(4-Chlorophenyl)-3H-imidazo[4,5-c]pyridin-2-yl]-1,3-thiazol-2-yl}piperazine | From Intermediate 84<br>Off white solid<br>Yield 9.50 mg, 2.96%*<br>HRMS (ESI$^+$) calcd for [MH]$^+$ of $C_{19}H_{17}ClN_6S$ 397.1002 found 397.1008.<br>HPLC: Rt 3.41-3.53 min, 99.3% purity |
| 20 | 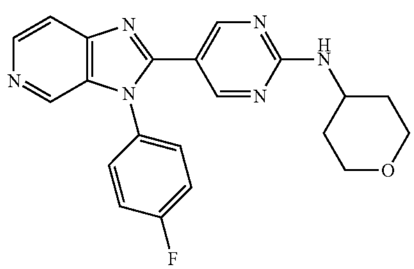 [SMILES: Fc1ccc(-n2c(-c3cnc(NC4CCOCC4)nc3)nc3ccncc32)cc1] | 5-[3-(4-Fluorophenyl)-3H-imidazo[4,5-c]pyridin-2-yl]-N-(oxan-4-yl)pyrimidin-2-amine | From Intermediate 85<br>White solid<br>Yield 79.0 mg, 13.9%<br>HRMS (ESI$^+$) calcd for [MH]$^+$ of $C_{21}H_{19}FN_6O$ 391.1682 found 391.1693.<br>HPLC: Rt 4.47 min, 100% purity |
| 21 | 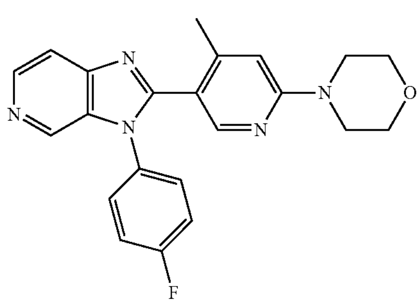 [SMILES: Cc1cc(N2CCOCC2)ncc1-c1nc2ccncc2n1-c1ccc(F)cc1] | 4-{5-[3-(4-Fluorophenyl)-3H-imidazo[4,5-c]pyridin-2-yl]-4-methylpyridin-2-yl}morpholine | From Intermediate 86<br>White solid<br>Yield 15.2 mg, 2.17%<br>HRMS (ESI$^+$) calcd for [MH]$^+$ of $C_{22}H_{20}FN_5O$ 390.1730 found 390.1721.<br>HPLC: Rt 4.09 min, 98.2% purity |
| 22 | 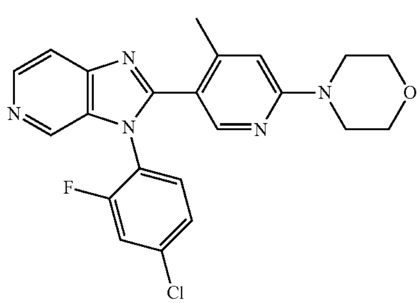 [SMILES: Cc1cc(N2CCOCC2)ncc1-c1nc2ccncc2n1-c1ccc(Cl)cc1F] | 4-{5-[3-(4-Chloro-2-fluorophenyl)-3H-imidazo[4,5-c]pyridin-2-yl]-4-methylpyridin-2-yl}morpholine | From Intermediate 88<br>Yellow solid<br>Yield 16.0 mg, 3.59%<br>HRMS (ESI$^+$) calcd for [MH]$^+$ of $C_{22}H_{19}ClFN_5O$ 424.1340 found 424.134.<br>HPLC: Rt 4.31 min, 98.4% purity |

TABLE 11-continued

Cyclisation of Intermediates 67-79, 81-86, 88-93, 95, 100-103, 105-106, 114-121, 124 and 125

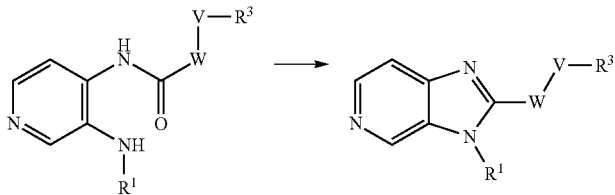

| Ex | Structure | Name | Intermediate(s), Form, Yield, LCMS, HPLC |
|---|---|---|---|
| 23 | 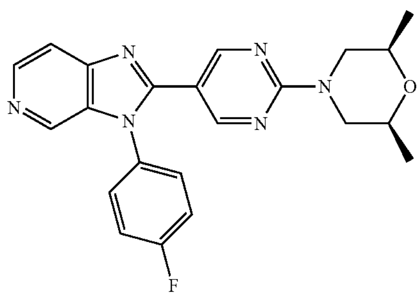 [SMILES: C[C@@H]1CN(c2ncc(-c3nc4ccncc4n3-c3ccc(F)cc3)cn2)C[C@H](C)O1] | (2R,6S)-4-{5-[3-(4-Fluorophenyl)-3H-imidazo[4,5-c]pyridin-2-yl]pyrimidin-2-yl}-2,6-dimethylmorpholine | From Intermediate 89 Beige solid Yield 25.8 mg, 6.39% HRMS (ESI+) calcd for [MH]+ of $C_{22}H_{21}FN_6O$ 405.1839 found 405.1843. HPLC: Rt 5.14 min, 99.1% purity |
| 24 | 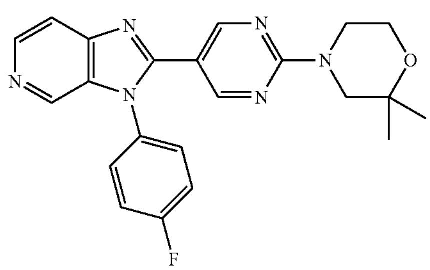 [SMILES: CC1(C)CN(c2ncc(-c3nc4ccncc4n3-c3ccc(F)cc3)cn2)CCO1] | 4-{5-[3-(4-Fluorophenyl)-3H-imidazo[4,5-c]pyridin-2-yl]pyrimidin-2-yl}-2,2-dimethylmorpholine | From Intermediate 90 White solid Yield 17.1 mg, 5.28% HRMS (ESI+) calcd for [MH]+ of $C_{22}H_{21}FN_6O$ 405.1839 found 405.1852. HPLC: Rt 5.14 min, 97.4% purity |
| 25 | 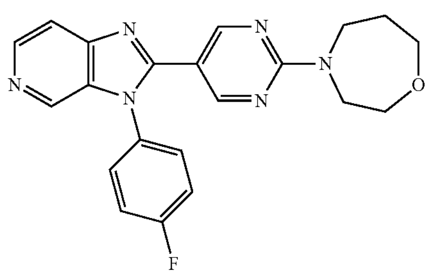 [SMILES: Fc1ccc(-n2c(-c3cnc(N4CCCOCC4)nc3)nc3ccncc32)cc1] | 4-{5-[3-(4-Fluorophenyl)-3H-imidazo[4,5-c]pyridin-2-yl]pyrimidin-2-yl}-1,4-oxazepane | From Intermediate 91 White solid Yield 415 mg, 43.5% HRMS (ESI+) calcd for [MH]+ of $C_{21}H_{19}FN_6O$ 391.1682 found 391.1682. HPLC: Rt 4.80 min, 98.7% purity |
| 26 | 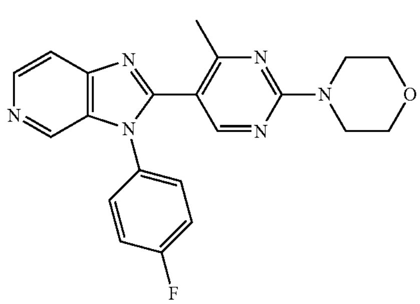 [SMILES: Cc1nc(N2CCOCC2)ncc1-c1nc2ccncc2n1-c1ccc(F)cc1] | 4-{5-[3-(4-Fluorophenyl)-3H-imidazo[4,5-c]pyridin-2-yl]-4-methylpyrimidin-2-yl}morpholine | From Intermediate 92 White solid Yield 8.50 mg, 1.76% HRMS (ESI+) calcd for [MH]+ of $C_{21}H_{19}FN_6O$ 391.1682 found 391.1676. HPLC: Rt 4.54 min, 97.8% purity |

TABLE 11-continued

Cyclisation of Intermediates 67-79, 81-86, 88-93, 95, 100-103, 105-106, 114-121, 124 and 125

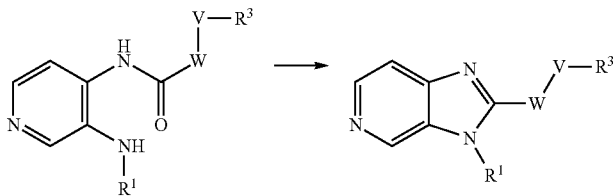

| Ex | Structure | Name | Intermediate(s), Form, Yield, LCMS, HPLC |
|---|---|---|---|
| 27 | 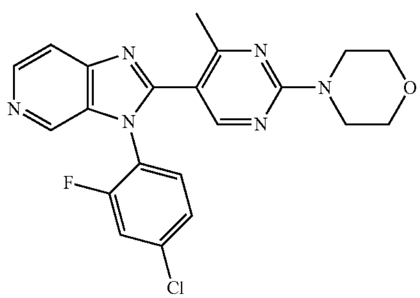 [SMILES: Cc1nc(N2CCOCC2)ncc1-c1nc2ccncc2n1-c1ccc(Cl)cc1F] | 4-{5-[3-(4-Chloro-2-fluorophenyl)-3H-imidazo[4,5-c]pyridin-2-yl]-4-methylpyrimidin-2-yl}morpholine | From Intermediate 93<br>White solid<br>Yield 37.0 mg, 8.28%<br>HRMS (ESI+) calcd for [MH]+ of $C_{21}H_{18}ClFN_6O$ 425.1293 found 425.1296.<br>HPLC: Rt 4.92 min, 99.8% purity |
| 28 | 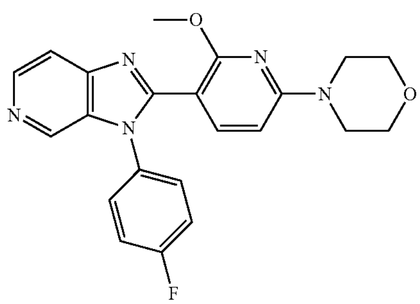 [SMILES: COc1nc(N2CCOCC2)ccc1-c1nc2ccncc2n1-c1ccc(F)cc1] | 4-{5-[3-(4-Fluorophenyl)-3H-imidazo[4,5-c]pyridin-2-yl]-6-methoxypyridin-2-yl}morpholine | From Intermediate 95<br>Pale yellow solid<br>Yield 47.4 mg, 41.6%<br>HRMS (ESI+) calcd for [MH]+ of $C_{22}H_{20}FN_5O_2$ 406.1679 found 406.1683.<br>HPLC: Rt 5.02 min, 99.5% purity |
| 29 | 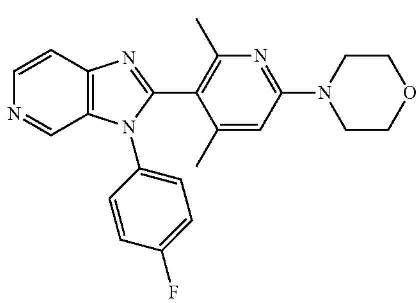 [SMILES: Cc1cc(N2CCOCC2)nc(C)c1-c1nc2ccncc2n1-c1ccc(F)cc1] | 4-{5-[3-(4-Fluorophenyl)-3H-imidazo[4,5-c]pyridin-2-yl]-4,6-dimethylpyridin-2-yl}morpholine | From Intermediate 124<br>Off white solid<br>Yield 15.0 mg, 2.00%<br>HRMS (ESI+) calcd for [MH]+ of $C_{23}H_{22}FN_5O$ 404.1887 found 404.1889.<br>HPLC: Rt 3.74 min, 99.5% purity |
| 30 | 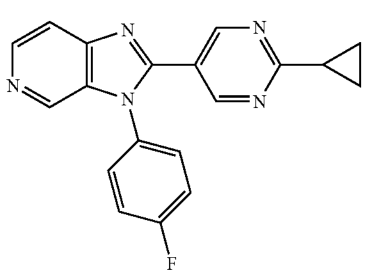 [SMILES: Fc1ccc(-n2c(-c3cnc(C4CC4)nc3)nc3ccncc32)cc1] | 2-Cyclopropyl-5-[3-(4-fluorophenyl)-3H-imidazo[4,5-c]pyridin-2-yl]pyrimidine | From Intermediate 100<br>Off white solid<br>Yield 50.2 mg, 17.3%<br>HRMS (ESI+) calcd for [MH]+ of $C_{19}H_{14}FN_5$ 332.1311 found 332.1313.<br>HPLC: Rt 4.59 min, 99.7% purity |

TABLE 11-continued

Cyclisation of Intermediates 67-79, 81-86, 88-93, 95, 100-103, 105-106, 114-121, 124 and 125

| Ex | Structure | Name | Intermediate(s), Form, Yield, LCMS, HPLC |
|---|---|---|---|
| 31 | 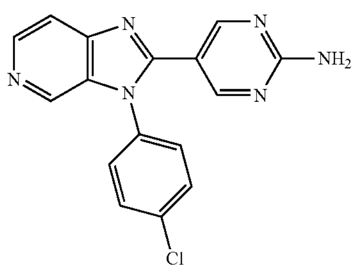 [SMILES: Nc1ncc(-c2nc3ccncc3n2-c2ccc(Cl)cc2)cn1] | 5-[3-(4-Chlorophenyl)-3H-imidazo[4,5-c]pyridin-2-yl]pyrimidin-2-amine | From Intermediate 101<br>Off white solid<br>Yield 14.0 mg, 3.16%<br>HRMS (ESI+) calcd for [MH]+ of $C_{16}H_{11}ClN_6$ 323.0812 found 323.0815.<br>HPLC: Rt 3.79 min, 100% purity |
| 32 | 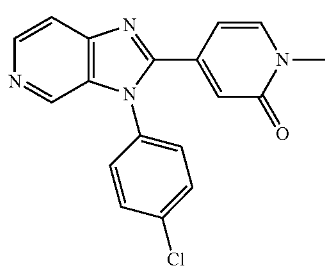 [SMILES: Cn1ccc(-c2nc3ccncc3n2-c2ccc(Cl)cc2)cc1=O] | 4-[3-(4-Chlorophenyl)-3H-imidazo[4,5-c]pyridin-2-yl]-1-methyl-1,2-dihydropyridin-2-one | From Intermediate 102<br>White solid<br>Yield 109 mg, 17.7%<br>HRMS (ESI+) calcd for [MH]+ of $C_{18}H_{13}ClN_4O$ 337.0856 found 337.0859.<br>HPLC: Rt 4.07 min, 98.8% purity |
| 33 | 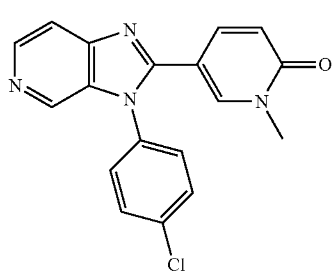 [SMILES: Cn1cc(-c2nc3ccncc3n2-c2ccc(Cl)cc2)ccc1=O] | 5-[3-(4-Chlorophenyl)-3H-imidazo[4,5-c]pyridin-2-yl]-1-methyl-1,2-dihydropyridin-2-one | From Intermediate 103<br>Off white solid<br>Yield 24.0 mg, 7.83%<br>HRMS (ESI+) calcd for [MH]+ of $C_{18}H_{13}ClN_4O$ 337.0856 found 337.0857.<br>HPLC: Rt 4.14 min, 99.6% purity |
| 34 | 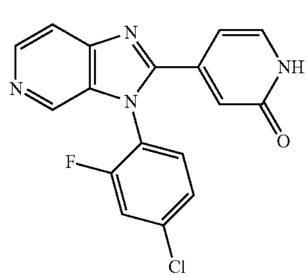 [SMILES: O=c1cc(-c2nc3ccncc3n2-c2ccc(Cl)cc2F)cc[nH]1] | 4-[3-(4-Chloro-2-fluorophenyl)-3H-imidazo[4,5-c]pyridin-2-yl]-1,2-dihydropyridin-2-one | From Intermediate 105<br>White solid<br>Yield 15.0 mg, 1.05%<br>HRMS (ESI+) calcd for [MH]+ of $C_{17}H_{10}ClFN_4O$ 341.0605 found 341.0607.<br>HPLC: Rt 3.55 min, 100% purity |

TABLE 11-continued

Cyclisation of Intermediates 67-79, 81-86, 88-93, 95, 100-103, 105-106, 114-121, 124 and 125

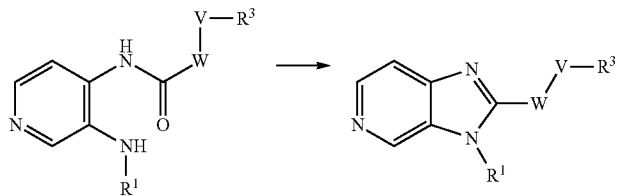

| Ex | Structure | Name | Intermediate(s), Form, Yield, LCMS, HPLC |
|---|---|---|---|
| 35 | 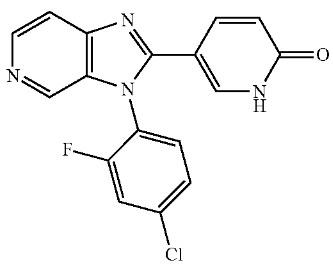 [SMILES: O=c1ccc(-c2nc3ccncc3n2-c2ccc(Cl)cc2F)c[nH]1] | 5-[3-(4-Chloro-2-fluorophenyl)-3H-imidazo[4,5-c]pyridin-2-yl]-1,2-dihydropyridin-2-one | From Intermediate 106<br>White solid<br>Yield 41.0 mg, 5.72%<br>HRMS (ESI$^+$) calcd for [MH]$^+$ of $C_{17}H_{10}ClFN_4O$ 341.0605 found 341.0613.<br>HPLC: Rt 3.65 min, 100% purity |
| 36 | 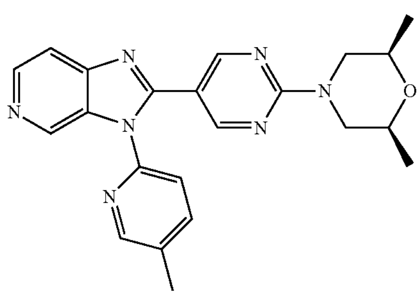 [SMILES: Cc1ccc(-n2c(-c3cnc(N4C[C@@H](C)O[C@@H](C)C4)nc3)nc3ccncc32)nc1] | (2R,6S)-2,6-Dimethyl-4-{5-[3-(5-methylpyridin-2-yl)-3H-imidazo[4,5-c]pyridin-2-yl]pyrimidin-2-yl}morpholine | From Intermediate 114<br>White solid<br>Yield 26.0 mg, 3.71%<br>HRMS (ESI$^+$) calcd for [MH]$^+$ of $C_{22}H_{23}N_7O$ 402.2042 found 402.2047.<br>HPLC: Rt 4.96 min, 98.8% purity |
| 37 | 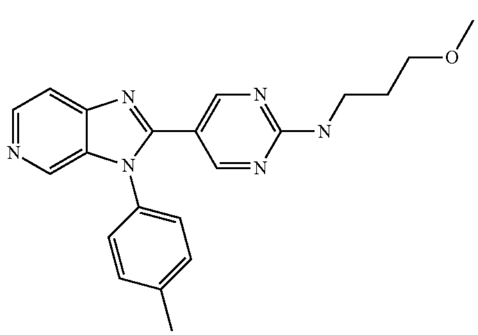 [SMILES: COCCCNc1ncc(-c2nc3ccncc3n2-c2ccc(C)cc2)cn1] | N-(3-Methoxypropyl)-5-[3-(4-methylphenyl)-3H-imidazo[4,5-c]pyridin-2-yl]pyrimidin-2-amine | From Intermediate 115<br>White solid<br>Yield 65.0 mg, 8.65%<br>HRMS (ESI$^+$) calcd for [MH]$^+$ of $C_{21}H_{22}N_6O$ 375.1933 found 375.1935.<br>HPLC: Rt 4.66 min, 99.3% purity |
| 38 | 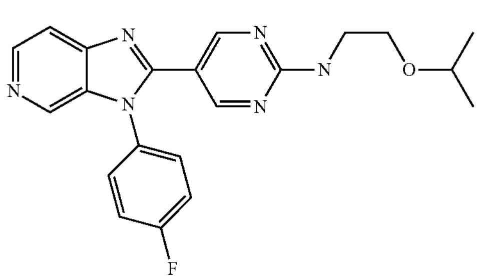 [SMILES: CC(C)OCCNc1ncc(-c2nc3ccncc3n2-c2ccc(F)cc2)cn1] | 5-[3-(4-Fluorophenyl)-3H-imidazo[4,5-c]pyridin-2-yl]-N-[2-(propan-2-yloxy)ethyl]pyrimidin-2-amine | From Intermediate 116<br>White solid<br>Yield 181 mg, 23.4%<br>HRMS (ESI$^+$) calcd for [MH]$^+$ of $C_{21}H_{21}FN_6O$ 393.1839 found 393.1823.<br>HPLC: Rt 4.80 min, 99.4% purity |

TABLE 11-continued

Cyclisation of Intermediates 67-79, 81-86, 88-93, 95, 100-103, 105-106, 114-121, 124 and 125

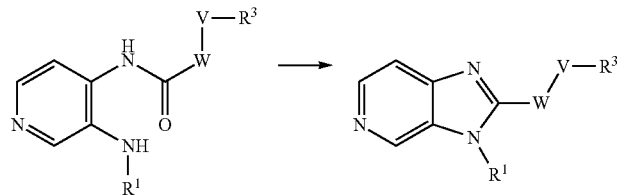

| Ex | Structure | Name | Intermediate(s), Form, Yield, LCMS, HPLC |
|---|---|---|---|
| 39 | 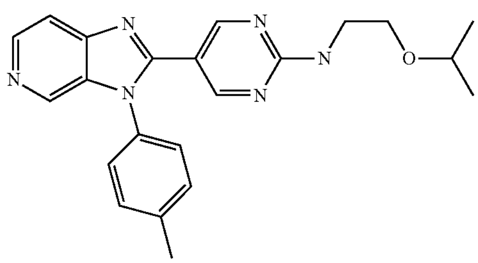 [SMILES: Cc1ccc(-n2c(-c3cnc(NCCOC(C)C)nc3)nc3ccncc32)cc1] | 5-[3-(4-Methylphenyl)-3H-imidazo[4,5-c]pyridin-2-yl]-N-[2-(propan-2-yloxy)ethyl]pyrimidin-2-amine | From Intermediate 117<br>White solid<br>Yield 55.7 mg, 7.14%<br>HRMS (ESI$^+$) calcd for [MH]$^+$ of $C_{22}H_{24}N_6O$ 389.2090 found 389.2083.<br>HPLC: Rt 5.01 min, 100% purity |
| 40 | 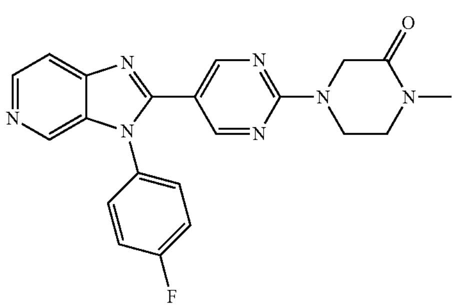 [SMILES: CN1CCN(c2ncc(-c3nc4ccncc4n3-c3ccc(F)cc3)cn2)CC1=O] | 4-{5-[3-(4-Fluorophenyl)-3H-imidazo[4,5-c]pyridin-2-yl]pyrimidin-2-yl}-1-methylpiperazin-2-one | From Intermediate 118<br>White solid<br>Yield 128 mg, 21.5%<br>HRMS (ESI$^+$) calcd for [MH]$^+$ of $C_{21}H_{18}FN_7O$ 404.1635 found 404.1620.<br>HPLC: Rt 4.22 min, 100% purity |
| 41 | 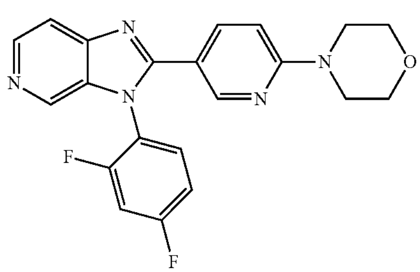 [SMILES: Fc1ccc(-n2c(-c3ccc(N4CCOCC4)nc3)nc3ccncc32)c(F)c1] | 4-{5-[3-(2,4-Difluorophenyl)-3H-imidazo[4,5-c]pyridin-2-yl]pyridin-2-yl}morpholine | From Intermediate 119<br>White solid<br>Yield 41.1 mg, 6.60%<br>HRMS (ESI$^+$) calcd for [MH]$^+$ of $C_{21}H_{17}F_2N_5O$ 394.1479 found 394.1469.<br>HPLC: Rt 4.47 min, 99.2% purity |

TABLE 11-continued

Cyclisation of Intermediates 67-79, 81-86, 88-93, 95, 100-103, 105-106, 114-121, 124 and 125

| Ex | Structure | Name | Intermediate(s), Form, Yield, LCMS, HPLC |
|---|---|---|---|
| 42 | 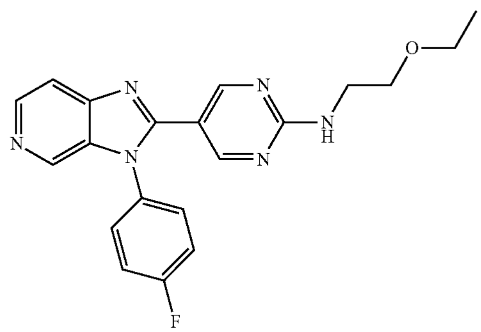 [SMILES: CCOCCNc1ncc(-c2nc3ccncc3n2-c2ccc(F)cc2)cn1] | N-(2-Ethoxyethyl)-5-[3-(4-fluorophenyl)-3H-imidazo[4,5-c]pyridin-2-yl]pyrimidin-2-amine | From Intermediate 120<br>Off white solid<br>Yield 154 mg, 27.6%<br>LCMS (ES$^+$): 379.0 [MH]$^+$<br>HPLC: Rt 4.70 min, 99.1% purity |
| 43 | 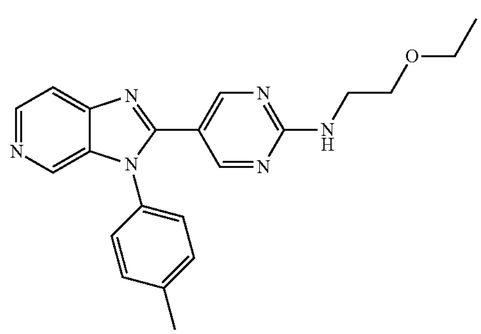 [SMILES: CCOCCNc1ncc(-c2nc3ccncc3n2-c2ccc(C)cc2)cn1] | N-(2-Ethoxyethyl)-5-[3-(4-methylphenyl)-3H-imidazo[4,5-c]pyridin-2-yl]pyrimidin-2-amine | From Intermediate 121<br>White solid<br>Yield 119 mg, 21.1%<br>LCMS (ES$^+$): 375.1 [MH]$^+$<br>HPLC: Rt 4.94 min, 99.1% purity |

*Boc deprotection under reaction conditions

Example 44

5-[3-(4-Chlorophenyl)-3H-imidazo[4,5-c]pyridin-2-yl]-1H-imidazole

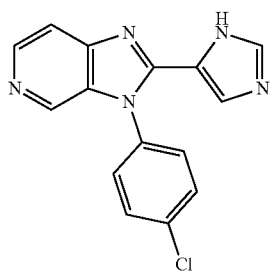 [SMILES: Clc1ccc(-n2c(-c3cnc[nH]3)nc3ccncc32)cc1]

Intermediate 1 (200 mg, 0.753 mmol) and imidazole-4-carboxaldehyde (86.8 mg, 0.903 mmol) were dissolved in EtOH (5 mL) and Na$_2$S$_2$O$_4$ (524 mg, 3.01 mmol) was added. The reaction mixture was heated using a microwave reactor at 160° C. for 1 h, diluted with sat. aq. NaHCO$_3$ (25 mL) and water (25 mL), and extracted into DCM (3×50 mL). The combined organic fractions were dried (MgSO$_4$) and concentrated in vacuo. The residue was purified by column chromatography to give the title compound as a yellow solid (51.2 mg, 23.0%). HRMS (ESI$^+$) calcd for [MH]$^+$ of C$_{15}$H$_{10}$ClN$_5$ 296.0703 found 296.0709. HPLC: Rt 3.24 min, 100% purity.

Examples 45-72

Examples 45-72 were prepared similarly to Example 44, by reductive condensation of Intermediates 1-11 with the appropriate aldehyde; see Table 12 below.

TABLE 12

Reductive condensations of Intermediates 1-11

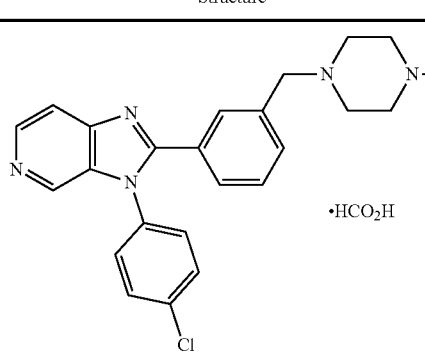

| Ex | Structure | Name | Intermediate(s) used, Form, Yield, LCMS, HPLC |
|---|---|---|---|
| 45 | 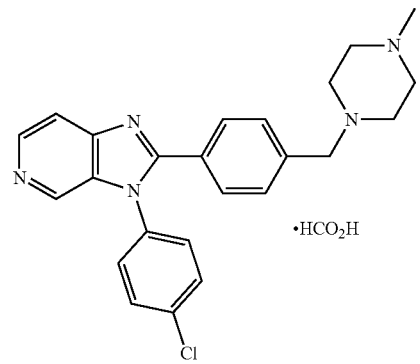 [SMILES: CN1CCN(Cc2ccc(-c3nc4ccncc4n3-c3ccc(Cl)cc3)cc2)CC1 ; "·HCO2H"] | 1-({3-[3-(4-Chlorophenyl)-3H-imidazo[4,5-c]pyridin-2-yl]phenyl}methyl)-4-methylpiperazine; formic acid | From Intermediate 1<br>White solid<br>Yield 34.6 mg, 9.91%<br>HRMS (ESI$^+$) calcd for [MH]$^+$ of $C_{24}H_{24}ClN_5$ 418.1798 found 418.1794.<br>HPLC: Rt 3.51 min, 99.0% purity |
| 46 | 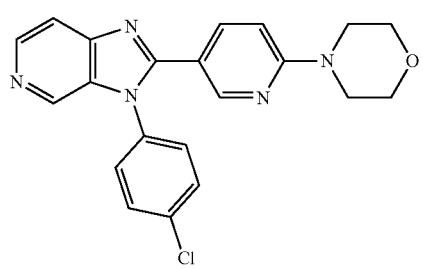 | 1-({4-[3-(4-Chlorophenyl)-3H-imidazo[4,5-c]pyridin-2-yl]phenyl}methyl)-4-methylpiperazine; formic acid | From Intermediate 1<br>Light yellow solid<br>Yield 42.0 mg, 12.0%<br>HRMS (ESI$^+$) calcd for [MH]$^+$ of $C_{24}H_{24}ClN_5$ 418.1798 found 418.1813.<br>HPLC: Rt 3.43 min, 99.1% purity |
| 47 | 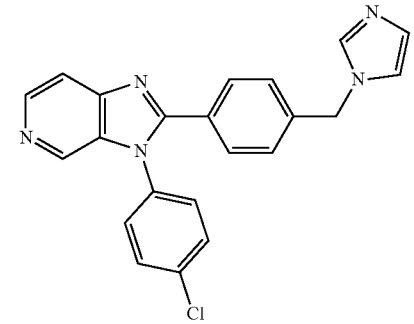 | 4-{5-[3-(4-Chlorophenyl)-3H-imidazo[4,5-c]pyridin-2-yl]pyridin-2-yl}morpholine | From Intermediate 1<br>White solid<br>Yield 70.9 mg, 20.9%<br>HRMS (ESI$^+$) calcd for [MH]$^+$ of $C_{21}H_{18}ClN_5O$ 392.1278 found 392.1282.<br>HPLC: Rt 4.49 min, 100% purity |
| 48 | 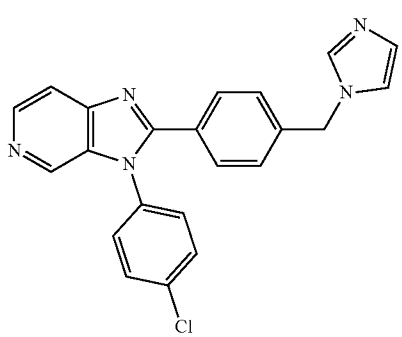 [SMILES: Clc1ccc(-n2c(-c3ccc(Cn4ccnc4)cc3)nc3ccncc32)cc1] | 1-({4-[3-(4-Chlorophenyl)-3H-imidazo[4,5-c]pyridin-2-yl]phenyl}methyl)-1H-imidazole | From Intermediate 1<br>Orange gum<br>Yield 39.4 mg, 11.4%<br>HRMS (ESI$^+$) calcd for [MH]$^+$ of $C_{22}H_{16}ClN_5$ 386.1172 found 386.1174.<br>HPLC: Rt 3.90 min, 100% purity |

TABLE 12-continued

Reductive condensations of Intermediates 1-11

| Ex | Structure | Name | Intermediate(s) used, Form, Yield, LCMS, HPLC |
|---|---|---|---|
| 49 | 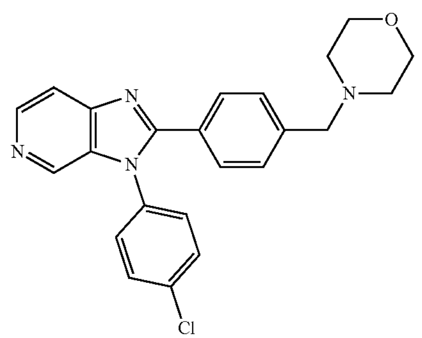 [SMILES: Clc1ccc(-n2c(-c3ccc(CN4CCOCC4)cc3)nc3ccncc32)cc1] | 4-({4-[3-(4-Chlorophenyl)-3H-imidazo[4,5-c]pyridin-2-yl]phenyl}methyl)morpholine | From Intermediate 1<br>Yellow solid<br>Yield 9.81 mg, 2.84%<br>HRMS (ESI$^+$) calcd for [MH]$^+$ of $C_{23}H_{21}ClN_4O$ 405.1482 found 405.1478.<br>HPLC: Rt 3.85 min, 100% purity |
| 50 | 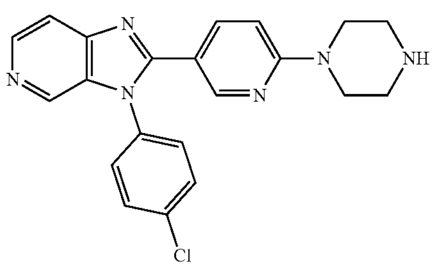 [SMILES: Clc1ccc(-n2c(-c3ccc(N4CCNCC4)nc3)nc3ccncc32)cc1] | 1-{5-[3-(4-Chlorophenyl)-3H-imidazo[4,5-c]pyridin-2-yl]pyridin-2-yl}piperazine | From Intermediate 1<br>Yellow solid<br>Yield 3.10 mg, 1.39% *<br>HRMS (ESI$^+$) calcd for [MH]$^+$ of $C_{21}H_{19}ClN_6$ 391.1438 found 391.1427.<br>HPLC: Rt 3.51 min, 100% purity |
| 51 | 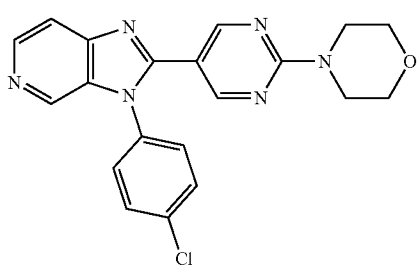 [SMILES: Clc1ccc(-n2c(-c3cnc(N4CCOCC4)nc3)nc3ccncc32)cc1] | 4-{5-[3-(4-Chlorophenyl)-3H-imidazo[4,5-c]pyridin-2-yl]pyrimidin-2-yl}morpholine | From Intermediate 1<br>White solid<br>2.75 mg, 0.73%<br>HRMS (ESI$^+$) calcd for [MH]$^+$ of $C_{20}H_{17}ClN_6O$ 393.1230 found 393.1234.<br>HPLC: Rt 5.06 min, 97.9% purity |
| 52 | 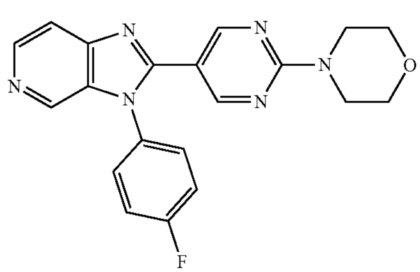 | 4-{5-[3-(4-Fluorophenyl)-3H-imidazo[4,5-c]pyridin-2-yl]pyrimidin-2-yl}morpholine | From Intermediate 2<br>White solid<br>Yield 166 mg, 36.6%<br>HRMS (ESI$^+$) calcd for [MH]$^+$ of $C_{20}H_{17}FN_6O$ 377.1526 found 377.1514.<br>HPLC: Rt 4.68 min, 98.1% purity |

TABLE 12-continued

Reductive condensations of Intermediates 1-11

| Ex | Structure | Name | Intermediate(s) used, Form, Yield, LCMS, HPLC |
|---|---|---|---|
| 53 | 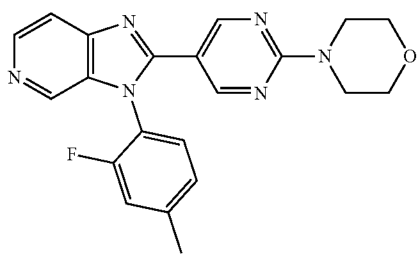 [SMILES: Cc1ccc(-n2c(-c3cnc(N4CCOCC4)nc3)nc3ccncc32)c(F)c1] | 4-{5-[3-(2-Fluoro-4-methylphenyl)-3H-imidazo[4,5-c]pyridin-2-yl]pyrimidin-2-yl}morpholine | From Intermediate 3 White solid Yield 40.1 mg, 13.5% HRMS (ESI$^+$) calcd for [MH]$^+$ of $C_{21}H_{19}FN_6O$ 391.1682 found 391.1674. HPLC: Rt 4.77 min, 99.3% purity |
| 54 | 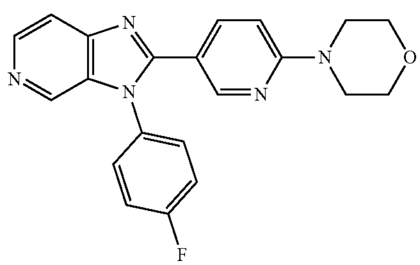 | 4-{5-[3-(4-Fluorophenyl)-3H-imidazo[4,5-c]pyridin-2-yl]pyridin-2-yl}morpholine | From Intermediate 2 White solid Yield 42.1 mg, 14.0% HRMS (ESI$^+$) calcd for [MH]$^+$ of $C_{21}H_{18}FN_5O$ 376.1573 found 376.1560. HPLC: Rt 4.20 min, 98.2% purity |
| 55 | 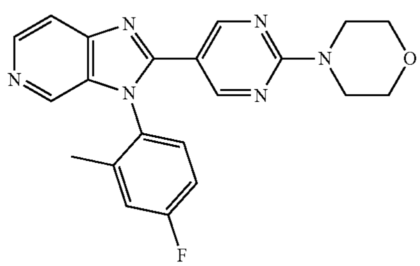 | 4-{5-[3-(4-Fluoro-2-methylphenyl)-3H-imidazo[4,5-c]pyridin-2-yl]pyrimidin-2-yl}morpholine | From Intermediate 4 Pale yellow solid Yield 22.2 mg, 3.74% HRMS (ESI$^+$) calcd for [MH]$^+$ of $C_{21}H_{19}FN_6O$ 391.1682 found 391.1679. HPLC: Rt 4.67 min, 98.2% purity |
| 56 | 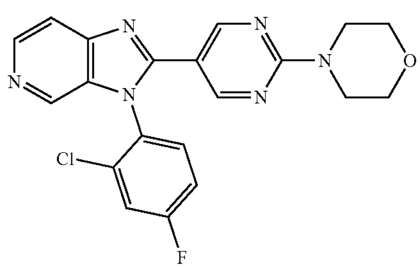 | 4-{5-[3-(2-Chloro-4-fluorophenyl)-3H-imidazo[4,5-c]pyridin-2-yl]pyrimidin-2-yl}morpholine | From Intermediate 5 Off white solid Yield 32.4 mg, 4.97% HRMS (ESI$^+$) calcd for [MH]$^+$ of $C_{20}H_{16}ClFN_6O$ 411.1136 found 411.1127. HPLC: Rt 4.72 min, 100% purity |
| 57 | 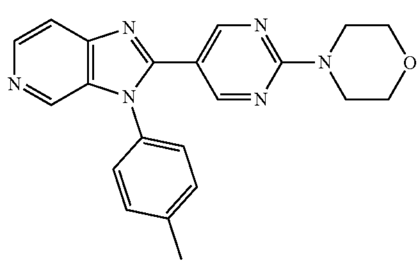 [SMILES: Cc1ccc(-n2c(-c3cnc(N4CCOCC4)nc3)nc3ccncc32)cc1] | 4-{5-[3-(4-Methylphenyl)-3H-imidazo[4,5-c]pyridin-2-yl]pyrimidin-2-yl}morpholine | From Intermediate 6 White solid Yield 35.7 mg, 5.22% HRMS (ESI$^+$) calcd for [MH]$^+$ of $C_{21}H_{20}N_6O$ 373.1777 found 373.1763. HPLC: Rt 4.80 min, 99.4% purity |

TABLE 12-continued

Reductive condensations of Intermediates 1-11

| Ex | Structure | Name | Intermediate(s) used, Form, Yield, LCMS, HPLC |
|---|---|---|---|
| 58 | 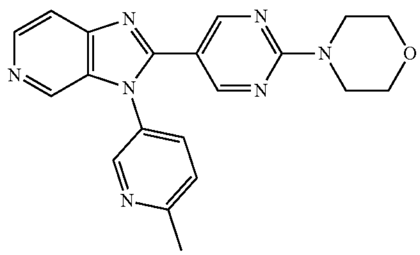 [SMILES: Cc1ccc(-n2c(-c3cnc(N4CCOCC4)nc3)nc3ccncc32)cn1] | 4-{5-[3-(6-Methylpyridin-3-yl)-3H-imidazo[4,5-c]pyridin-2-yl]pyrimidin-2-yl}morpholine | From Intermediate 7<br>Off white solid<br>Yield 39.0 mg, 5.14%<br>HRMS (ESI+) calcd for [MH]+ of $C_{20}H_{19}N_7O$ 374.1729 found 374.1736.<br>HPLC: Rt 3.90 min, 99.1% purity |
| 59 | 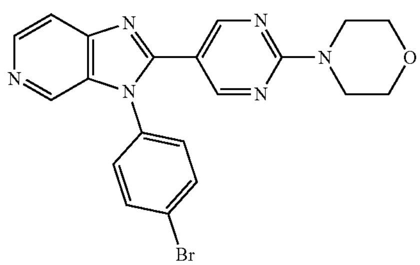 | 4-{5-[3-(4-Bromophenyl)-3H-imidazo[4,5-c]pyridin-2-yl]pyrimidin-2-yl}morpholine | From Intermediate 8<br>White solid<br>Yield 55.0 mg, 7.80%<br>HRMS (ESI+) calcd for [MH]+ of $C_{20}H_{17}BrN_6O$ 437.0725 found 437.0717.<br>HPLC: Rt 5.15 min, 99.0% purity |
| 60 | 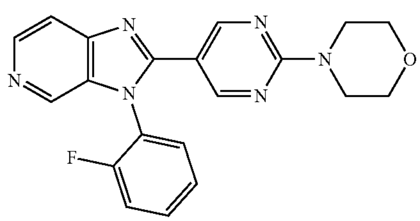 | 4-{5-[3-(2-Fluorophenyl)-3H-imidazo[4,5-c]pyridin-2-yl]pyrimidin-2-yl}morpholine | From Intermediate 9<br>White solid<br>Yield 18.0 mg, 2.38%<br>HRMS (ESI+) calcd for [MH]+ of $C_{20}H_{17}FN_6O$ 377.1526 found 377.1515.<br>HPLC: Rt 4.54 min, 99.4% purity |
| 61 | 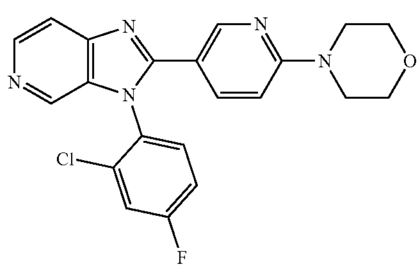 [SMILES: Fc1ccc(-n2c(-c3ccc(N4CCOCC4)nc3)nc3ccncc32)c(Cl)c1] | 4-{5-[3-(2-Chloro-4-fluorophenyl)-3H-imidazo[4,5-c]pyridin-2-yl]pyridin-2-yl}morpholine | From Intermediate 5<br>Pale yellow solid<br>Yield 23.0 mg, 3.54%<br>HRMS (ESI+) calcd for [MH]+ of $C_{21}H_{17}ClFN_5O$ 410.1184 found 410.1189.<br>HPLC: Rt 4.54 min, 99.2% purity |
| 62 | 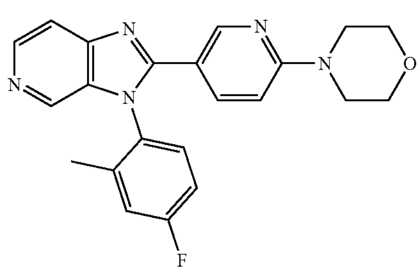 | 4-{5-[3-(4-Fluoro-2-methylphenyl)-3H-imidazo[4,5-c]pyridin-2-yl]pyridin-2-yl}morpholine | From Intermediate 4<br>Pale yellow solid<br>Yield 21.1 mg, 3.57%<br>HRMS (ESI+) calcd for [MH]+ of $C_{22}H_{20}FN_5O$ 390.1730 found 390.1723.<br>HPLC: Rt 4.50 min, 99.3% purity |

TABLE 12-continued

Reductive condensations of Intermediates 1-11

| Ex | Structure | Name | Intermediate(s) used, Form, Yield, LCMS, HPLC |
|---|---|---|---|
| 63 | 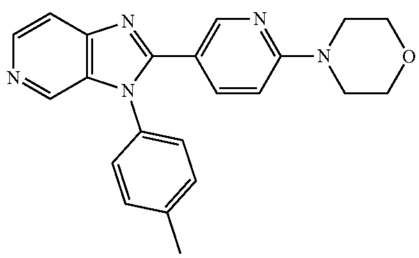 [SMILES: Cc1ccc(-n2c(-c3ccc(N4CCOCC4)nc3)nc3ccncc32)cc1] | 4-{5-[3-(4-Methylphenyl)-3H-imidazo[4,5-c]pyridin-2-yl]pyridin-2-yl}morpholine | From Intermediate 6<br>White solid<br>Yield 72.0 mg, 9.51%<br>HRMS (ESI$^+$) calcd for [MH]$^+$ of $C_{22}H_{21}N_5O$ 372.1824 found 372.1820.<br>HPLC: Rt 4.75 min, 100% purity |
| 64 | 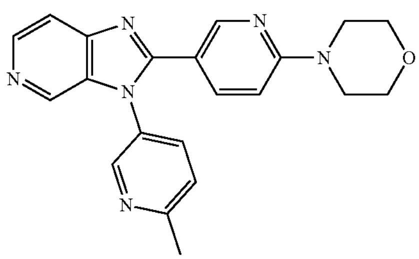 [SMILES: Cc1ccc(-n2c(-c3ccc(N4CCOCC4)nc3)nc3ccncc32)cn1] | 4-{5-[3-(6-Methylpyridin-3-yl)-3H-imidazo[4,5-c]pyridin-2-yl]pyridin-2-yl}morpholine | From Intermediate 7<br>White solid<br>Yield 52.0 mg, 7.24%<br>HRMS (ESI$^+$) calcd for [MH]$^+$ of $C_{21}H_{20}N_6O$ 373.1777 found 373.1768.<br>HPLC: Rt 3.69 min, 100% purity |
| 65 | 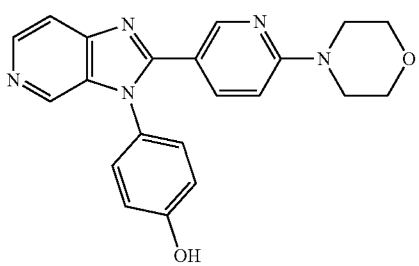 | 4-{2-[6-(Morpholin-4-yl)pyridin-3-yl]-3H-imidazo[4,5-c]pyridin-3-yl}phenol | From Intermediate 10<br>Off white solid<br>Yield 106 mg, 14.0%<br>HRMS (ESI$^+$) calcd for [MH]$^+$ of $C_{21}H_{19}N_5O_2$ 374.1617 found 374.1618.<br>HPLC: Rt 3.88 min, 99.5% purity |
| 66 | 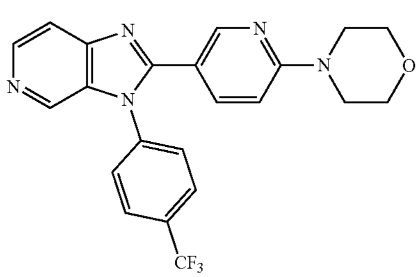 [SMILES: FC(F)(F)c1ccc(-n2c(-c3ccc(N4CCOCC4)nc3)nc3ccncc32)cc1] | 4-(5-{3-[4-(Trifluoromethyl)phenyl]-3H-imidazo[4,5-c]pyridin-2-yl}pyridin-2-yl)morpholine | From Intermediate 11<br>Off white solid<br>Yield 22.0 mg, 3.09%<br>HRMS (ESI$^+$) calcd for [MH]$^+$ of $C_{22}H_{18}F_3N_5O$ 426.1541 found 426.1549.<br>HPLC: Rt 4.88 min, 99.5% purity |
| 67 | 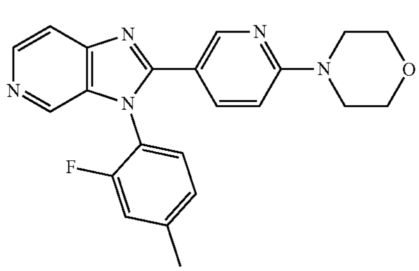 [SMILES: Cc1ccc(-n2c(-c3ccc(N4CCOCC4)nc3)nc3ccncc32)c(F)c1] | 4-{5-[3-(2-Fluoro-4-methylphenyl)-3H-imidazo[4,5-c]pyridin-2-yl]pyridin-2-yl}morpholine | From Intermediate 3<br>Pale yellow solid<br>Yield 78.3 mg, 10.6%<br>HRMS (ESI$^+$) calcd for [MH]$^+$ of $C_{22}H_{20}FN_5O$ 390.1730 found 390.1729.<br>HPLC: Rt 4.66 min, 99.7% purity |

TABLE 12-continued

Reductive condensations of Intermediates 1-11

| Ex | Structure | Name | Intermediate(s) used, Form, Yield, LCMS, HPLC |
|---|---|---|---|
| 68 | | 4-{5-[3-(2-Fluorophenyl)-3H-imidazo[4,5-c]pyridin-2-yl]pyridin-2-yl}morpholine | From Intermediate 9<br>White solid<br>Yield 73.0 mg, 9.69%<br>HRMS (ESI+) calcd for [MH]+ of $C_{21}H_{18}FN_5O$ 376.1573 found 376.1584.<br>HPLC: Rt 4.33 min, 99.5% purity |
| 69 | | 5-[3-(4-Fluorophenyl)-3H-imidazo[4,5-c]pyridin-2-yl]-2-(pyrrolidin-1-yl)pyrimidine | From Intermediate 2<br>White solid<br>Yield 42.2 mg, 7.29%<br>HRMS (ESI+) calcd for [MH]+ of $C_{20}H_{17}FN_6$ 361.1577 found 361.1584.<br>HPLC: Rt 4.83 min, 98.5% purity |
| 70 | | 4-{5-[3-(4-Fluorophenyl)-3H-imidazo[4,5-c]pyridin-2-yl]pyridin-2-yl}-2-methylmorpholine | From Intermediates 2 and 65<br>Orange solid<br>Yield 42.7 mg, 9.11%<br>HRMS (ESI+) calcd for [MH]+ of $C_{22}H_{20}FN_5O$ 390.1730 found 390.1726.<br>HPLC: Rt 4.54 min, 99.4% purity |
| 71 | | 5-[3-(4-Fluorophenyl)-3H-imidazo[4,5-c]pyridin-2-yl]-N,N-dimethylpyridin-2-amine | From Intermediate 2<br>White solid<br>Yield 84.0 mg, 12.6%<br>HRMS (ESI+) calcd for [MH]+ of $C_{19}H_{16}FN_5$ 334.1468 found 334.1475.<br>HPLC: Rt 3.72 min, 100% purity |
| 72 | | 5-[3-(4-Chlorophenyl)-3H-imidazo[4,5-c]pyridin-2-yl]-N,N-dimethylpyrimidin-2-amine | From Intermediates 1 and 64<br>White solid<br>Yield 12.6 mg, 1.91%<br>HRMS (ESI+) calcd for [MH]+ of $C_{18}H_{15}ClN_6$ 351.1125 found 351.1125.<br>HPLC: Rt 4.90 min, 100% purity |

* Additional Boc deprotection step incorporated

Example 73

4-{4-[3-(4-Fluorophenyl)-3H-imidazo[4,5-c]pyridin-2-yl]pyridin-2-yl}morpholine

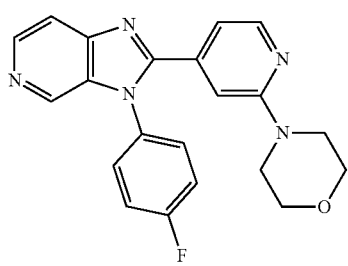 [SMILES: Fc1ccc(-n2c(-c3ccnc(N4CCOCC4)c3)nc3ccncc32)cc1]

Intermediate 20 (250 mg, 1.24 mmol), 2-(morpholin-4-yl)pyridine-4-carbaldehyde (238 mg, 1.24 mmol) and Na₂S₂O₄ (646 mg, 3.71 mmol) were suspended in EtOH (2 mL) and the reaction mixture was heated at 150° C. in a microwave reactor for 45 min. The reaction mixture was poured into 1M aq. Na₂CO₃ (25 mL) and extracted with DCM (2×25 mL). The combined organic fractions were dried (MgSO₄) and concentrated in vacuo. The residue was triturated from MeOH (2 mL) to give the title compound (101 mg, 21.7%) as an off white solid. HRMS (ESI⁺) calcd for [MH]⁺ of C₂₁H₁₈FN₅O 376.1573 found 376.1573. HPLC: Rt 3.89 min, 97.8% purity.

Example 74

4-{5-[3-(4-Chloro-3-fluorophenyl)-3H-imidazo[4,5-c]pyridin-2-yl]pyrimidin-2-yl}morpholine

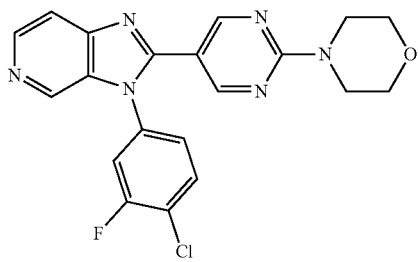

Intermediate 13 (200 mg, 0.747 mmol), 2-(morpholin-4-yl)pyrimidine-5-carbaldehyde (188 mg, 0.971 mmol) and Na₂S₂O₄ (520 mg, 2.99 mmol) were suspended in EtOH (5 mL) and the reaction mixture was heated using a microwave reactor at 160° C. for 1 h. The reaction mixture was diluted with 1M aq. Na₂CO₃ (40 mL) and extracted into DCM (2×50 mL). The combined organic fractions were dried (MgSO₄) and concentrated in vacuo. The residue was purified by column chromatography and by reverse phase HPLC to give the title compound (36.6 mg, 11.9%) as an off white solid. HRMS (ESI⁺) calcd for [MH]⁺ of C₂₀H₁₆ClFN₆O 411.1136 found 411.1133. HPLC: Rt 5.09 min, 99.7% purity.

Examples 75-84

Examples 75-84 were prepared similarly to Example 74, by reductive condensation of Intermediates 14-18 with the appropriate aldehyde; see Table 13 below.

TABLE 13

Reductive condensations of Intermediates 14-18

| Ex | Structure | Name | Intermediate(s) used, Form, Yield, LCMS, HPLC |
|---|---|---|---|
| 75 | 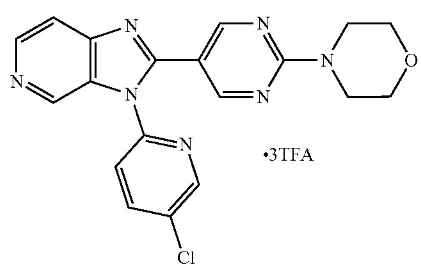 [SMILES: Clc1ccc(-n2c(-c3cnc(N4CCOCC4)nc3)nc3ccncc32)nc1] | 4-{5-[3-(5-Chloropyridin-2-yl)-3H-imidazo[4,5-c]pyridin-2-yl]pyrimidin-2-yl}morpholine; tris(trifluoroacetic acid) | From Intermediate 14<br>White solid<br>Yield 29.0 mg, 4.47%<br>HRMS (ESI⁺) calcd for [MH]⁺ of C₁₉H₁₆ClN₇O 394.1183 found 394.1168.<br>HPLC: Rt 4.68 min, 97.8% purity |

TABLE 13-continued

Reductive condensations of Intermediates 14-18

| Ex | Structure | Name | Intermediate(s) used, Form, Yield, LCMS, HPLC |
|---|---|---|---|
| 76 | 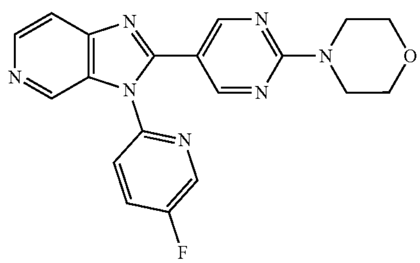 | 4-{5-[3-(5-Fluoropyridin-2-yl)-3H-imidazo[4,5-c]pyridin-2-yl]pyrimidin-2-yl}morpholine | From Intermediate 15<br>White solid<br>Yield 53.2 mg, 7.49%<br>HRMS (ESI$^+$) calcd for [MH]$^+$ of $C_{19}H_{16}FN_7O$ 378.1479 found 378.1473.<br>HPLC: Rt 4.36 min, 98.4% purity |
| 77 | 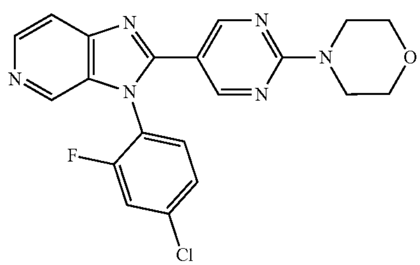 | 4-{5-[3-(4-Chloro-2-fluorophenyl)-3H-imidazo[4,5-c]pyridin-2-yl]pyrimidin-2-yl}morpholine | From Intermediate 16<br>Yellow solid<br>Yield 186 mg, 15.4%<br>HRMS (ESI$^+$) calcd for [MH]$^+$ of $C_{20}H_{16}ClFN_6O$ 411.1136 found 411.1142.<br>HPLC: Rt 5.09 min, 97.6% purity |
| 78 | 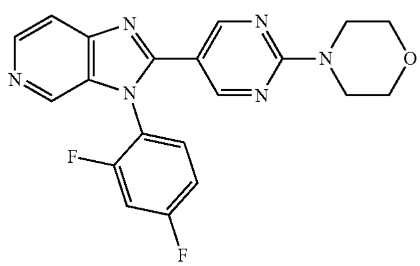 | 4-{5-[3-(2,4-Difluorophenyl)-3H-imidazo[4,5-c]pyridin-2-yl]pyrimidin-2-yl}morpholine | From Intermediate 17<br>Pale yellow solid<br>Yield 39.2 mg, 4.54%<br>HRMS (ESI$^+$) calcd for [MH]$^+$ of $C_{20}H_{16}F_2N_6O$ 395.1432 found 395.1436.<br>HPLC: Rt 4.76 min, 99.6% purity |
| 79 | 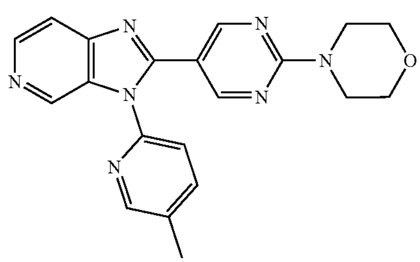 | 4-{5-[3-(5-Methylpyridin-2-yl)-3H-imidazo[4,5-c]pyridin-2-yl]pyrimidin-2-yl}morpholine | From Intermediate 18<br>Off white solid<br>Yield 46.1 mg, 9.47%<br>HRMS (ESI$^+$) calcd for [MH]$^+$ of $C_{20}H_{19}N_7O$ 374.1729 found 374.1736.<br>HPLC: Rt 4.30 min, 99.6% purity |
| 80 | 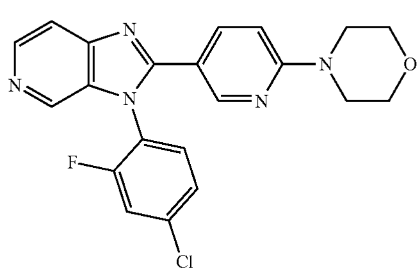 [SMILES: Fc1cc(Cl)ccc1-n1c(-c2ccc(N3CCOCC3)nc2)nc2ccncc21] | 4-{5-[3-(4-Chloro-2-fluorophenyl)-3H-imidazo[4,5-c]pyridin-2-yl]pyridin-2-yl}morpholine | From Intermediate 16<br>White solid<br>Yield 41.0 mg, 12.8%<br>HRMS (ESI$^+$) calcd for [MH]$^+$ of $C_{21}H_{17}ClFN_5O$ 410.1184 found 410.1187.<br>HPLC: Rt 4.58 min, 99.6% purity |

TABLE 13-continued

Reductive condensations of Intermediates 14-18

| Ex | Structure | Name | Intermediate(s) used, Form, Yield, LCMS, HPLC |
|---|---|---|---|
| 81 | 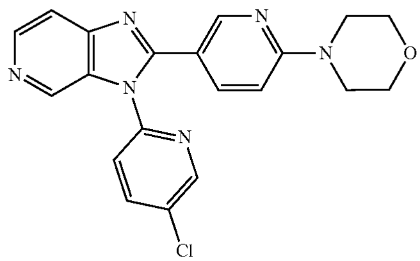 | 4-{5-[3-(5-Chloropyridin-2-yl)-3H-imidazo[4,5-c]pyridin-2-yl]pyridin-2-yl}morpholine | From Intermediate 14<br>White solid<br>Yield 7.05 mg, 2.57%<br>HRMS (ESI$^+$) calcd for [MH]$^+$ of $C_{20}H_{17}ClN_6O$ 393.1230 found 393.1226.<br>HPLC: Rt 4.45 min, 97.9% purity |
| 82 | 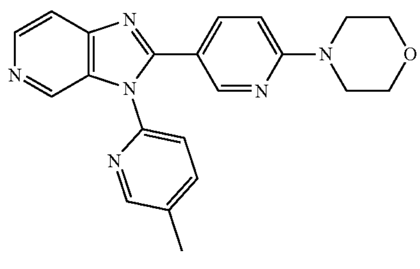 [SMILES: Cc1ccc(-n2c(-c3ccc(N4CCOCC4)nc3)nc3ccncc32)nc1] | 4-{5-[3-(5-Methylpyridin-2-yl)-3H-imidazo[4,5-c]pyridin-2-yl]pyridin-2-yl}morpholine | From Intermediate 18<br>White solid<br>Yield 38.0 mg, 7.83%<br>HRMS (ESI$^+$) calcd for [MH]$^+$ of $C_{21}H_{20}N_6O$ 373.1777 found 373.1787.<br>HPLC: Rt 4.03 min, 99.4% purity |
| 83 | 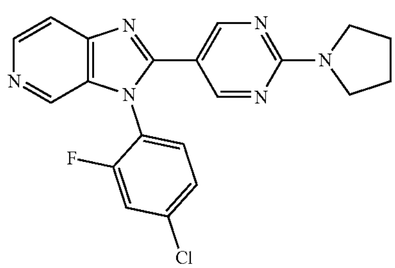 [SMILES: Fc1cc(Cl)ccc1-n1c(-c2cnc(N3CCCC3)nc2)nc2ccncc21] | 5-[3-(4-Chloro-2-fluorophenyl)-3H-imidazo[4,5-c]pyridin-2-yl]-2-(pyrrolidin-1-yl)pyrimidine | From Intermediate 16<br>White solid<br>Yield 8.20 mg, 2.22%<br>HRMS (ESI$^+$) calcd for [MH]$^+$ of $C_{20}H_{16}ClFN_6$ 395.1187 found 395.1190.<br>HPLC: Rt 5.09 min, 100% purity |
| 84 | 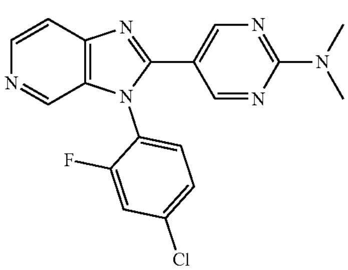 [SMILES: CN(C)c1ncc(-c2nc3ccncc3n2-c2ccc(Cl)cc2F)cn1] | 5-[3-(4-Chloro-2-fluorophenyl)-3H-imidazo[4,5-c]pyridin-2-yl]-N,N-dimethylpyrimidin-2-amine | From Intermediates 16 and 64<br>Light yellow solid<br>Yield 63.7 mg, 13.6%<br>HRMS (ESI$^+$) calcd for [MH]$^+$ of $C_{18}H_{14}ClFN_6$ 369.1031 found 369.1031.<br>HPLC: Rt 4.93 min, 100% purity |

Example 85

N-(1-{5-[3-(4-Chlorophenyl)-3H-imidazo[4,5-c]pyridin-2-yl]pyridin-2-yl}piperidin-4-yl)acetamide

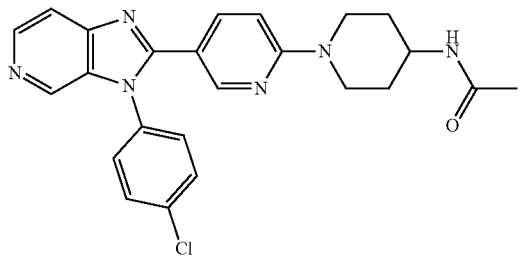 [SMILES: CC(=O)NC1CCN(c2ccc(-c3nc4ccncc4n3-c3ccc(Cl)cc3)cn2)CC1]

Example 8 (100 mg, 0.247 mmol), Et$_3$N (41.2 uL, 0.296 mmol) and acetyl chloride (19.3 uL, 0.272 mmol) were dissolved in DCM (10 mL) and the reaction mixture was stirred for 2 h and concentrated in vacuo. The residue was purified by column chromatography and partitioned between DCM (20 mL) and sat. aq. NaHCO$_3$ (20 mL). The organic fraction was washed with sat. aq. NaHCO$_3$ (20 mL), dried (MgSO$_4$) and concentrated in vacuo to give the title compound (61.6 mg, 55.8%) as a light yellow solid. HRMS (ESI$^+$) calcd for [MH]$^+$ of C$_{24}$H$_{23}$ClN$_6$O 447.1700 found 447.1701. HPLC: Rt 3.98 min, 99.7% purity.

Example 86

1-(4-{5-[3-(4-Fluorophenyl)-3H-imidazo[4,5-c]pyridin-2-yl]pyridin-2-yl}piperazin-1-yl)ethan-1-one

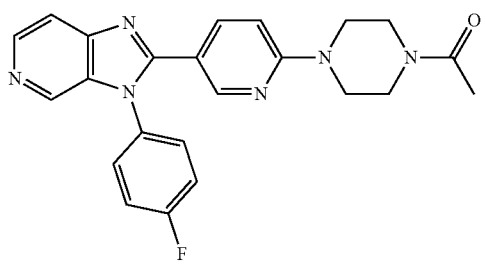 [SMILES: CC(=O)N1CCN(c2ccc(-c3nc4ccncc4n3-c3ccc(F)cc3)cn2)CC1]

Example 86 was prepared similarly to Example 85, using Intermediate 126 instead of Example 8, to give the title compound (227 mg, 38.7%) as a white solid. HRMS (ESI$^+$) calcd for [MH]$^+$ of C$_{23}$H$_{21}$FN$_6$O 417.1839 found 417.1851. HPLC: Rt 4.26 min, 100% purity.

Example 87

1-(4-{5-[3-(4-Fluorophenyl)-3H-imidazo[4,5-c]pyridin-2-yl]pyridin-2-yl}-1,4-diazepan-1-yl)ethan-1-one; Bis(trifluoroacetic Acid)

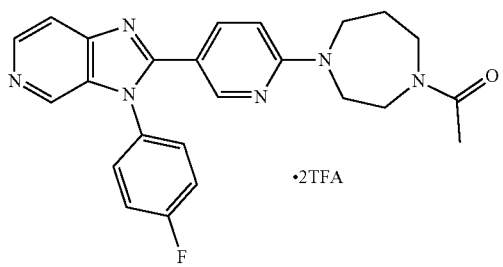 [SMILES: CC(=O)N1CCCN(c2ccc(-c3nc4ccncc4n3-c3ccc(F)cc3)cn2)CC1]

Example 87 was prepared similarly to Example 85, using Intermediate 129 instead of Example 8, to give the title compound (143 mg, 41.2%) as a pink gum. HRMS (ESI$^+$) calcd for [MH]$^+$ of C$_{24}$H$_{23}$FN$_6$O 431.1996 found 431.1997. HPLC: Rt 4.41 min, 99.7% purity.

Example 88

N-(1-{5-[3-(4-Chlorophenyl)-3H-imidazo[4,5-c]pyridin-2-yl]pyridin-2-yl}piperidin-4-yl)methanesulfonamide

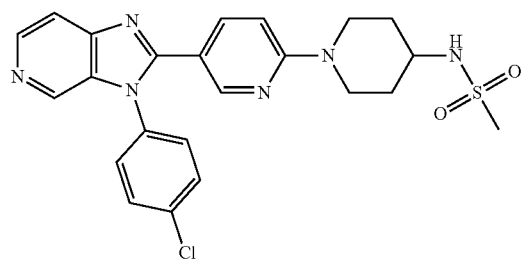 [SMILES: CS(=O)(=O)NC1CCN(c2ccc(-c3nc4ccncc4n3-c3ccc(Cl)cc3)cn2)CC1]

Example 8 (100 mg, 0.247 mmol), Et$_3$N (41.2 uL, 0.296 mmol) and methanesulfonyl chloride (26.8 uL, 0.346 mmol) were dissolved in DCM (10 mL) and the reaction mixture was stirred for 2 h, diluted with DCM (20 mL), washed with sat. aq. NaHCO$_3$ (30 mL), dried (MgSO$_4$) and concentrated in vacuo. The residue was triturated from MeOH (3 mL) and collected by filtration to give the title compound (30.6 mg, 25.7%) as a yellow solid. HRMS (ESI$^+$) calcd for [MH]$^+$ of C$_{23}$H$_{23}$ClN$_6$O$_2$S 483.1370 found 483.1375. HPLC: Rt 4.18 min, 99.4% purity.

Example 89

1-{5-[3-(4-Fluorophenyl)-3H-imidazo[4,5-c]pyridin-2-yl]pyridin-2-yl}-4-methanesulfonylpiperazine

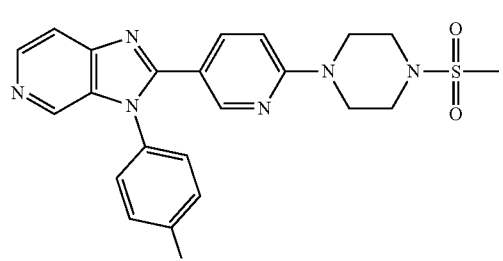

Example 89 was prepared similarly to Example 88, using Intermediate 126 instead of Example 8, to give the title compound (44.5 mg, 10.3%) as a yellow solid. HRMS (ESI$^+$) calcd for [MH]$^+$ of C$_{22}$H$_{21}$FN$_6$O$_2$S 453.1509 found 453.1522. HPLC: Rt 4.59 min, 98.2% purity.

Example 90

4-{5-[3-(4-Chlorophenyl)-3H-imidazo[4,5-c]pyridin-2-yl]pyridin-2-yl}piperazine-1-carboxamide Dihydrochloride

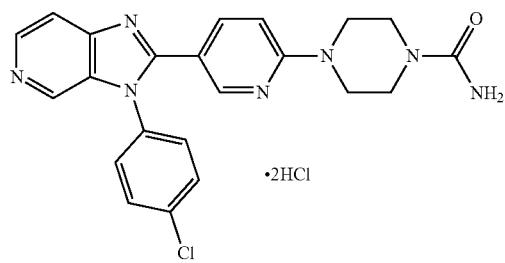 [SMILES: NC(=O)N1CCN(c2ccc(-c3nc4ccncc4n3-c3ccc(Cl)cc3)cn2)CC1]

·2HCl

Example 50 trihydrochloride (94.5 mg, 0.189 mmol) was dissolved in DCM (5 mL), and DIPEA (145 uL, 0.831 mmol) and trimethylsilyl isocyanate (30.7 uL, 0.227 mmol) were added. The reaction mixture was stirred for 16 h, diluted with 1M aq. $Na_2CO_3$ (25 mL) and extracted into DCM (3×25 mL). The combined organic fractions were dried ($MgSO_4$) and concentrated in vacuo. The residue was dissolved in 1.25M HCl in EtOH (5 mL), stirred for 1 h and concentrated in vacuo. The residue was purified by reverse phase HPLC to give the title compound (21.4 mg, 22.3%) as a yellow solid. HRMS (ESI$^+$) calcd for [MH]$^+$ of $C_{22}H_{20}ClN_7O$ 434.1496 found 434.1497. HPLC: Rt 4.19 min, 98.5% purity.

Examples 91-94

Examples 91-94 were prepared similarly to Example 90, by reaction of Examples 8, 18 and Intermediates 126, 129 with trimethylsilyl isocyanate; see Table 14 below.

TABLE 14

Reaction of Examples 8, 18 and Intermediates 126, 129 with trimethylsilyl isocyanate

| Ex | Structure | Name | Intermediate(s) used, Form, Yield, LCMS, HPLC |
|---|---|---|---|
| 91 | (structure with 2·TFA) | (1-{5-[3-(4-Chlorophenyl)-3H-imidazo[4,5-c]pyridin-2-yl]pyridin-2-yl}piperidin-4-yl)urea; bis(trifluoroacetic acid) | From Example 8. Yellow solid. Yield 36.3 mg, 21.7%. HRMS (ESI$^+$) calcd for [MH]$^+$ of $C_{23}H_{22}ClN_7O$ 448.1653 found 448.1656. HPLC: Rt 3.75 min, 98.7% purity |
| 92 | (structure) | 4-{5-[3-(4-Fluorophenyl)-3H-imidazo[4,5-c]pyridin-2-yl]pyridin-2-yl}piperazine-1-carboxamide | From Intermediate 126. White solid. Yield 44.0 mg, 11.1%. HRMS (ESI$^+$) calcd for [MH]$^+$ of $C_{22}H_{20}FN_7O$ 418.1791 found 418.1795. HPLC: Rt 3.88 min, 100% purity |
| 93 | (structure) | 4-{5-[3-(4-Chlorophenyl)-3H-imidazo[4,5-c]pyridin-2-yl]-1,3-oxazol-2-yl}piperazine-1-carboxamide | From Example 18. Pale yellow solid. Yield 7.20 mg, 7.71%. HRMS (ESI$^+$) calcd for [MH]$^+$ of $C_{20}H_{18}ClN_7O_2$ 424.1289 found 424.1288. HPLC: Rt 4.20 min, 99.7% purity |

TABLE 14-continued

Reaction of Examples 8, 18 and Intermediates 126, 129 with trimethylsilyl isocyanate

| Ex | Structure | Name | Intermediate(s) used, Form, Yield, LCMS, HPLC |
|---|---|---|---|
| 94 | 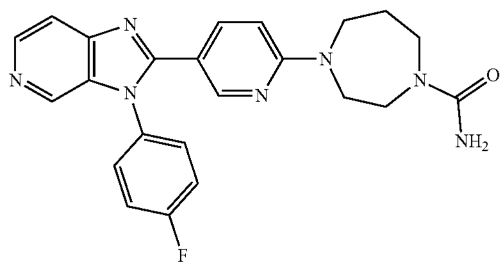 [SMILES: NC(=O)N1CCCN(c2ccc(-c3nc4ccncc4n3-c3ccc(F)cc3)cn2)CC1] | 4-{5-[3-(4-Fluorophenyl)-3H-imidazo[4,5-c]pyridin-2-yl]pyridin-2-yl}-1,4-diazepane-1-carboxamide | From Intermediate 129 Pink solid Yield 56.7 mg, 24.9% HRMS (ESI+) calcd for [MH]+ of $C_{23}H_{22}FN_7O$ 432.1948 found 432.1955. HPLC: Rt 3.83 min, 99.0% purity |

Example 95

4-(5-{3-Phenyl-3H-imidazo[4,5-c]pyridin-2-yl}pyrimidin-2-yl)morpholine

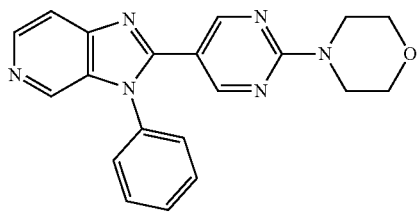 [SMILES: c1ccc(-n2c(-c3cnc(N4CCOCC4)nc3)nc3ccncc32)cc1]

Example 51 (115 mg, 0.293 mmol) was suspended in EtOH (5 mL) and ammonium formate (148 mg, 2.34 mmol) and 10% Pd/C (50.0 mg) were added. The reaction mixture was heated under reflux for 5 h, filtered through Celite and concentrated in vacuo. The residue was dissolved in DCM (50 mL), washed with 1M aq. $Na_2CO_3$ (50 mL) dried ($MgSO_4$) and concentrated in vacuo. The residue was purified by column chromatography to give the title compound (40.2 mg, 38.3%) as a white solid. HRMS (ESI+) calcd for [MH]+ of $C_{20}H_{18}N_6O$ 359.1620 found 359.1613. HPLC: Rt 4.65 min, 99.8% purity.

Example 96

4-{5-[3-(4-Cyclopropyl phenyl)-3H-imidazo[4,5-c]pyridin-2-yl]pyrimidin-2-yl}morpholine

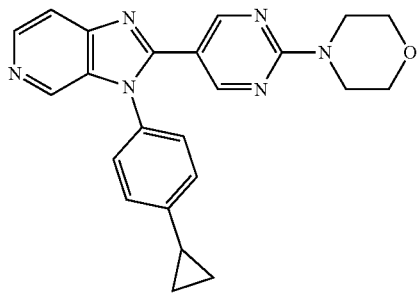 [SMILES: c1cc2nc(-c3cnc(N4CCOCC4)nc3)n(-c3ccc(C4CC4)cc3)c2cn1]

Example 51 (250 mg, 0.636 mmol), cyclopropylboronic acid (54.7 mg, 0.636 mmol), Pd(OAc)$_2$ (14.3 mg, 63.6 umol), XPhos (30.3 mg, 63.6 umol) and $Cs_2CO_3$ (518 mg, 1.59 mmol) were dissolved in dioxane (1.5 mL) and water (1.5 mL) and heated in a sealed tube at 100° C. for 16 h. The reaction mixture was partitioned between DCM (20 mL) and water (20 mL) and the organic fraction was washed with brine (20 mL), dried ($MgSO_4$) and concentrated in vacuo. The residue was purified by reverse phase HPLC to give the title compound (17.1 mg, 6.74%) as a white solid. HRMS (ESI+) calcd for [MH]+ of $C_{23}H_{22}N_6O$ 399.1933 found 399.1938. HPLC: Rt 5.16 min, 99.4% purity.

Example 97

4-{4-Methyl-5-[3-(4-methyl phenyl)-3H-imidazo[4,5-c]pyridin-2-yl]pyridin-2-yl}morpholine

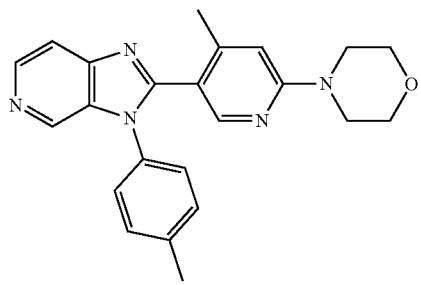 [SMILES: Cc1ccc(-n2c(-c3cnc(N4CCOCC4)cc3C)nc3ccncc32)cc1]

Intermediate 87 (300 mg, 1.51 mmol) was dissolved in NMP (2 mL) and morpholine (783 uL, 9.08 mmol) and the reaction mixture was heated at 180° C. in a microwave reactor for 30 min. The reaction mixture was diluted with EtOAc (10 mL) and water (10 mL). The organic fraction was washed with brine (10 mL), dried ($MgSO_4$) and concentrated in vacuo. The residue was purified by reverse phase HPLC to give the title compound (16.4 mg, 2.81%) as a colourless gum. HRMS (ESI+) calcd for [MH]+ of $C_{23}H_{23}N_5O$ 386.1981 found 386.1982. HPLC: Rt 4.17 min, 99.3% purity.

Examples 98-107

Examples 98-107 were prepared similarly to Example 97, by SnAr and cyclisation of Intermediates 97-98, 106, 109-110, 112, 122 and 123 with the appropriate amine; see Table 15 below.

TABLE 15

SnAr and cyclisation of Intermediates 97-98, 106, 109-110, 112, 122 and 123

X = F or Cl

| Ex | Structure | Name | Intermediate(s) used, Form, Yield, LCMS, HPLC |
|---|---|---|---|
| 98 | 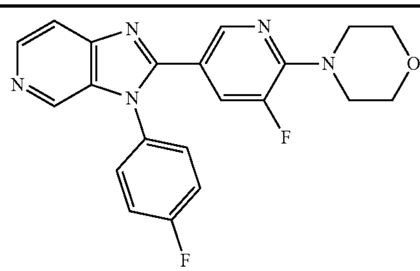 | 4-{3-Fluoro-5-[3-(4-fluorophenyl)-3H-imidazo[4,5-c]pyridin-2-yl]pyridin-2-yl}morpholine | From Intermediate 97<br>White solid<br>Yield 134 mg, 27.7%<br>HRMS (ESI$^+$) calcd for [MH]$^+$ of $C_{21}H_{17}F_2N_5O$ 394.1479 found 394.1478.<br>HPLC: Rt 4.80 min, 99.6% purity |
| 99 | 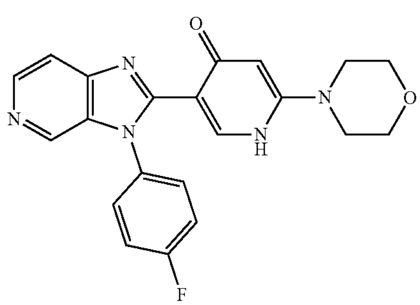 [SMILES: O=c1cc(N2CCOCC2)[nH]cc1-c1nc2ccncc2n1-c1ccc(F)cc1] | 5-[3-(4-Fluorophenyl)-3H-imidazo[4,5-c]pyridin-2-yl]-2-(morpholin-4-yl)-1,4-dihydropyridin-4-one | From Intermediate 98<br>White solid<br>Yield 15.0 mg, 1.11%<br>HRMS (ESI$^+$) calcd for [MH]$^+$ of $C_{21}H_{18}FN_5O_2$ 392.1523 found 392.1520.<br>HPLC: Rt 3.73 min, 100% purity |
| 100 | 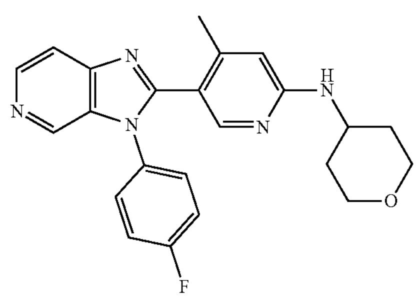 [SMILES: Cc1cc(NC2CCOCC2)ncc1-c1nc2ccncc2n1-c1ccc(F)cc1] | 5-[3-(4-Fluorophenyl)-3H-imidazo[4,5-c]pyridin-2-yl]-4-methyl-N-(oxan-4-yl)pyridin-2-amine | From Intermediate 109<br>White solid<br>Yield 26.0 mg, 8.77%<br>HRMS (ESI$^+$) calcd for [MH]$^+$ of $C_{23}H_{22}FN_5O$ 404.1887 found 404.1892.<br>HPLC: Rt 3.56 min, 100% purity |
| 101 | 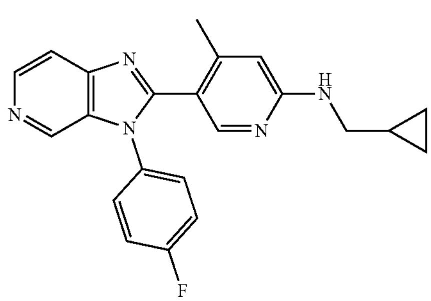 [SMILES: Cc1cc(NCC2CC2)ncc1-c1nc2ccncc2n1-c1ccc(F)cc1] | N-(Cyclopropylmethyl)-5-[3-(4-fluorophenyl)-3H-imidazo[4,5-c]pyridin-2-yl]-4-methylpyridin-2-amine | From Intermediate 109<br>White solid<br>Yield 43.0 mg, 15.7%<br>HRMS (ESI$^+$) calcd for [MH]$^+$ of $C_{22}H_{20}FN_5$ 374.1781 found 374.1787.<br>HPLC: Rt 3.90 min, 100% purity |

TABLE 15-continued

SnAr and cyclisation of Intermediates 97-98, 106, 109-110, 112, 122 and 123

X = F or Cl

| Ex | Structure | Name | Intermediate(s) used, Form, Yield, LCMS, HPLC |
|---|---|---|---|
| 102 | 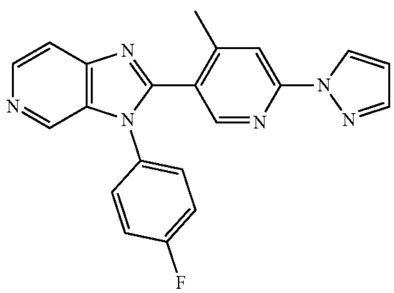 [SMILES: Cc1cc(-n2cccn2)ncc1-c1nc2ccncc2n1-c1ccc(F)cc1] | 5-[3-(4-Fluorophenyl)-3H-imidazo[4,5-c]pyridin-2-yl]-4-methyl-2-(1H-pyrazol-1-yl)pyridine | From Intermediate 109 Off white solid Yield 28.1 mg, 12.9% HRMS (ESI$^+$) calcd for [MH]$^+$ of $C_{21}H_{15}FN_6$ 371.1420 found 371.1419. HPLC: Rt 4.98 min, 99.8% purity |
| 103 | 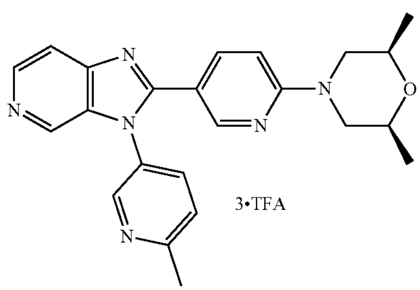 [SMILES: Cc1ccc(-n2c(-c3ccc(N4C[C@@H](C)O[C@@H](C)C4)nc3)nc3ccncc32)cn1] | (2R,6S)-2,6-Dimethyl-4-{5-[3-(6-methylpyridin-3-yl)-3H-imidazo[4,5-c]pyridin-2-yl]pyridin-2-yl}morpholine; tris(trifluoroacetic acid) | From Intermediate 110 Yellow gum Yield 26.0 mg, 1.75% HRMS (ESI$^+$) calcd for [MH]$^+$ of $C_{23}H_{24}N_6O$ 401.2090 found 401.2084. HPLC: Rt 4.27 min, 99.1% purity |
| 104 | 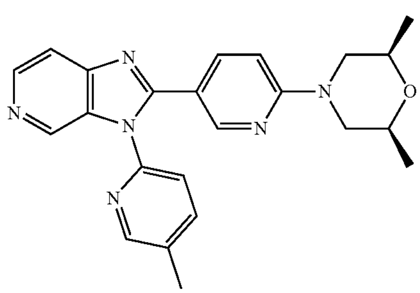 [SMILES: Cc1ccc(-n2c(-c3ccc(N4C[C@@H](C)O[C@@H](C)C4)nc3)nc3ccncc32)nc1] | (2R,6S)-2,6-Dimethyl-4-{5-[3-(5-methylpyridin-2-yl)-3H-imidazo[4,5-c]pyridin-2-yl]pyridin-2-yl}morpholine | From Intermediate 112 White solid Yield 26.0 mg, 3.71% HRMS (ESI$^+$) calcd for [MH]$^+$ of $C_{23}H_{24}N_6O$ 401.2090 found 401.2098. HPLC: Rt 4.66 min, 98.9% purity |
| 105 | 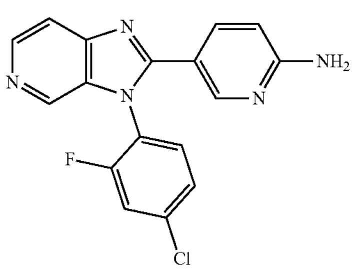 [SMILES: Nc1ccc(-c2nc3ccncc3n2-c2ccc(Cl)cc2F)cn1] | 5-[3-(4-Chloro-2-fluorophenyl)-3H-imidazo[4,5-c]pyridin-2-yl]pyridin-2-amine | From Intermediate 106 Pale pink solid Yield 24.0 mg, 8.49% HRMS (ESI$^+$) calcd for [MH]$^+$ of $C_{17}H_{11}ClFN_5$ 340.0765 found 340.0773. HPLC: Rt 3.30 min, 100% purity |

TABLE 15-continued

SnAr and cyclisation of Intermediates 97-98, 106, 109-110, 112, 122 and 123

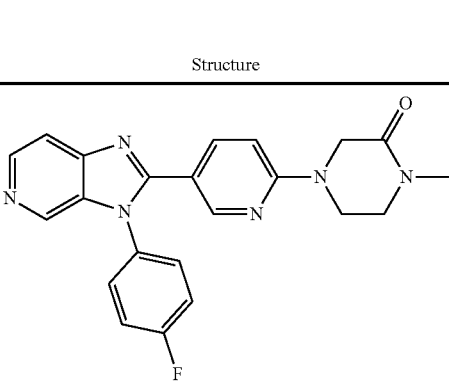

X = F or Cl

| Ex | Structure | Name | Intermediate(s) used, Form, Yield, LCMS, HPLC |
|---|---|---|---|
| 106 | 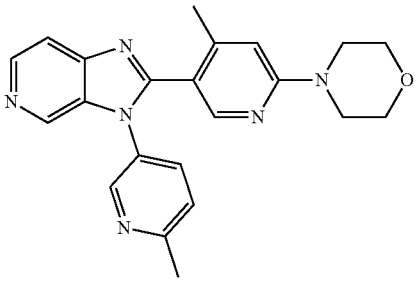 | 4-{5-[3-(4-Fluorophenyl)-3H-imidazo[4,5-c]pyridin-2-yl]pyridin-2-yl}-1-methylpiperazin-2-one | From Intermediate 123 Pale yellow solid Yield 38.5 mg, 13.1% HRMS (ESI$^+$) calcd for [MH]$^+$ of $C_{22}H_{19}FN_6O$ 403.1682 found 403.1684. HPLC: Rt 4.07 min, 99.4% purity |
| 107 | 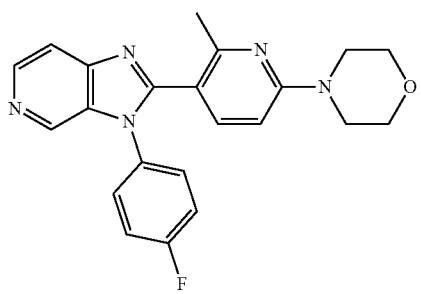 | 4-{4-Methyl-5-[3-(6-methylpyridin-3-yl)-3H-imidazo[4,5-c]pyridin-2-yl]pyridin-2-yl}morpholine | From Intermediate 122 Pale yellow gum Yield 24.0 mg, 3.11% LCMS (ESI$^+$): 387.0 [MH]$^+$ HPLC: Rt 3.74 min, 98.7% purity |

Example 108

4-{5-[3-(4-Fluorophenyl)-3H-imidazo[4,5-c]pyridin-2-yl]-6-methylpyridin-2-yl}morpholine Intermediate 130 (94.0 mg, 0.277 mmol) was dissolved in DMA (1 mL) and morpholine (192 uL, 2.22 mmol) was added. The reaction mixture was heated at 200° C. in a microwave reactor for 30 min and partitioned between DCM (20 mL) and water (20 mL). The organic fraction was washed with water (20 mL), dried (MgSO$_4$) and concentrated in vacuo. The residue was purified by reverse phase HPLC to give the title compound (47.0 mg, 43.5%) as a white solid. HRMS (ESI$^+$) calcd for [MH]$^+$ of $C_{22}H_{20}FN_5O$ 390.1730 found 390.1737. HPLC: Rt 3.96 min, 99.7% purity.

Examples 109-111

Examples 109-111 were prepared similarly to Example 108, by reaction of Intermediates 128, 131 and 133 with the appropriate amine; see Table 16 below.

TABLE 16

SNAr of Intermediates 128, 131 and 133 with the appropriate amine

| Ex | Structure | Name | Intermediate(s) used, Form, Yield, LCMS, HPLC |
|---|---|---|---|
| 109 | 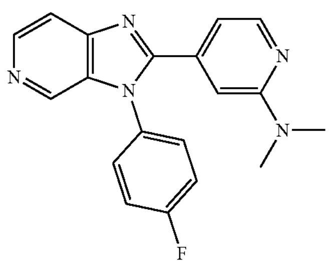 [SMILES: CN(C)c1cc(-c2nc3ccncc3n2-c2ccc(F)cc2)ccn1] | 4-[3-(4-Fluorophenyl)-3H-imidazo[4,5-c]pyridin-2-yl]-N,N-dimethylpyridin-2-amine | From Intermediate 131<br>Yellow solid<br>Yield 110 mg, 53.4%<br>HRMS (ESI$^+$) calcd for [MH]$^+$ of $C_{19}H_{16}FN_5$ 334.1468 found 334.1476.<br>HPLC: Rt 3.19 min, 99.7% purity |
| 110 | 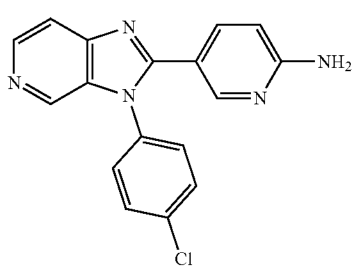 [SMILES: Nc1ccc(-c2nc3ccncc3n2-c2ccc(Cl)cc2)cn1] | 5-[3-(4-Chlorophenyl)-3H-imidazo[4,5-c]pyridin-2-yl]pyridin-2-amine | From Intermediate 128<br>White solid<br>Yield 20.0 mg, 26.2%<br>HRMS (ESI$^+$) calcd for [MH]$^+$ of $C_{17}H_{12}ClN_5$ 322.0859 found 322.0849.<br>HPLC: Rt 3.45 min, 99.7% purity |
| 111 | 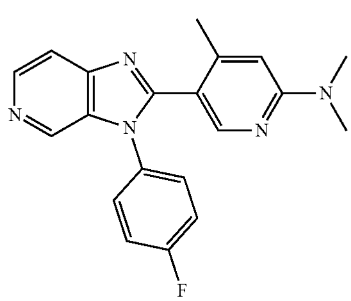 [SMILES: Cc1cc(N(C)C)ncc1-c1nc2ccncc2n1-c1ccc(F)cc1] | 5-[3-(4-Fluorophenyl)-3H-imidazo[4,5-c]pyridin-2-yl]-N,N,4-trimethylpyridin-2-amine | From Intermediate 133<br>Light yellow solid<br>Yield 24.8 mg, 29.2%<br>HRMS (ESI$^+$) calcd for [MH]$^+$ of $C_{20}H_{18}FN_5$ 348.1624 found 348.1631.<br>HPLC: Rt 3.44 min, 99.1% purity |

Example 112

5-[3-(4-Fluorophenyl)-3H-imidazo[4,5-c]pyridin-2-yl]-2-(oxolan-3-yloxy)pyridine

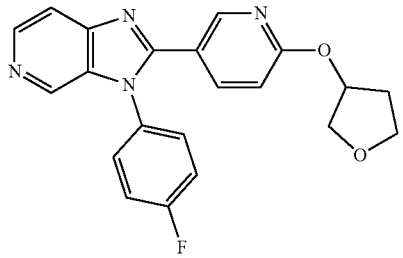 [SMILES: Fc1ccc(-n2c(-c3ccc(OC4CCOC4)nc3)nc3ccncc32)cc1]

NaH (14.8 mg, 60% in mineral oil, 0.370 mmol) was suspended in THF (1 mL), 3-hydroxytetrahydrofuran (29.7 uL, 0.370 mmol) was added and the reaction mixture was stirred for 5 min. Intermediate 127 (80.0 mg, 0.246 mmol) was added and the reaction mixture was stirred for 16 h, quenched with water (20 mL) and diluted with EtOAc (20 mL). The organic fraction was washed with brine (20 mL), dried (MgSO$_4$) and concentrated in vacuo. The residue was purified by reverse phase HPLC to give the title compound (19.2 mg, 20.7%) as a white solid. HRMS (ESI$^+$) calcd for [MH]$^+$ of C$_{21}$H$_{17}$FN$_4$O$_2$ 377.1414 found 377.1419. HPLC: Rt: 4.78 min, 98.9% purity.

Example 113

5-[3-(4-Fluorophenyl)-3H-imidazo[4,5-c]pyridin-2-yl]-2-(oxan-4-yloxy)pyridine

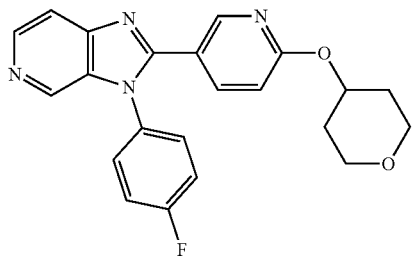 [SMILES: Fc1ccc(-n2c(-c3ccc(OC4CCOCC4)nc3)nc3ccncc32)cc1]

Example 113 was prepared similarly to Example 112, using 4-hydroxytetrahydropyran instead of 3-hydroxytetrahydrofuran, to give the title compound (20.0 mg, 20.8%) as a white solid. HRMS (ESI$^+$) calcd for [MH]$^+$ of C$_{22}$H$_{19}$FN$_4$O$_2$ 391.1570 found 391.1566. HPLC: Rt 5.04 min, 99.7% purity.

Example 114

4-[3-(4-Fluorophenyl)-3H-imidazo[4,5-c]pyridin-2-yl]-1-methyl-1,2-dihydropyridin-2-one

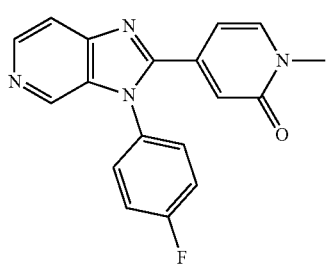 [SMILES: Cn1ccc(-c2nc3ccncc3n2-c2ccc(F)cc2)cc1=O]

Intermediate 132 (26.0 mg, 84.9 umol) and Cs$_2$CO$_3$ (55.3 mg, 0.170 mmol) were dissolved in dioxane (0.5 mL), MeI (10.6 uL, 0.170 mmol) was added and the reaction mixture was stirred for 16 h, filtered and concentrated in vacuo. The residue was purified by reverse phase HPLC to give the title compound (1.41 mg, 5.19%) as a white solid. HRMS (ESI$^+$) calcd for [MH]$^+$ of C$_{18}$H$_{13}$FN$_4$O 321.1151 found 321.1156. HPLC: Rt 3.45 min, 98.9% purity.

Example 115

1-Cyclopropyl-4-[3-(4-fluorophenyl)-3H-imidazo[4,5-c]pyridin-2-yl]-1,2-dihydropyridin-2-one

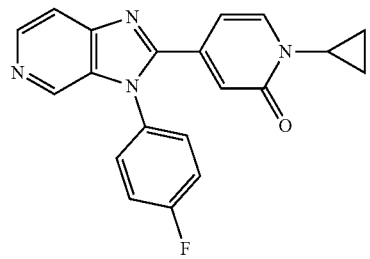 [SMILES: O=c1cc(-c2nc3ccncc3n2-c2ccc(F)cc2)ccn1C1CC1]

Intermediate 132 (120 mg, 0.392 mmol), cyclopropylboronic acid (101 mg, 1.18 mmol), Cu(OAc)$_2$ (110 mg, 0.607 mmol), 4,4'-dimethyl-2,2'-bipyridine (72.2 mg, 0.392 mmol) and Cs$_2$CO$_3$ (268 mg, 0.823 mmol) were suspended in dioxane (2.5 mL) and the reaction mixture was stirred at 70° C. for 6 h. The reaction mixture was partitioned between EtOAc (25 mL) and water (25 mL) and the organic fraction was washed with brine (25 mL), dried (MgSO$_4$) and concentrated in vacuo. The residue was purified by reverse phase HPLC to give the title compound (22.4 mg, 16.5%) as an off white solid. HRMS (ESI$^+$) calcd for [MH]$^+$ of C$_{20}$H$_{15}$FN$_4$O 347.1308 found 347.1309. HPLC: Rt 3.88 min, 100% purity.

Example 116

4-[3-(4-Chloro-2-fluorophenyl)-3H-imidazo[4,5-c]pyridin-2-yl]-1-cyclopropyl-1,2-dihydropyridin-2-one

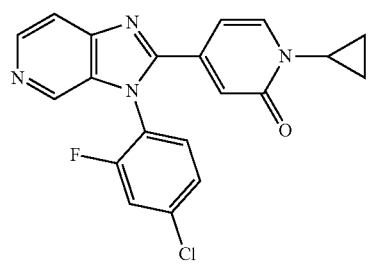 [SMILES: O=c1cc(-c2nc3ccncc3n2-c2ccc(Cl)cc2F)ccn1C1CC1]

Example 116 was prepared similarly to Example 115, using Example 34 instead of Intermediate 132, to give the title compound (31.0 mg, 34.7%) as an off white solid. HRMS (ESI$^+$) calcd for [MH]$^+$ of C$_{20}$H$_{14}$ClFN$_4$O 381.0918 found 381.0922. HPLC: Rt 4.13 min, 100% purity.

Example 117

N-(2-Methoxyethyl)-N-methyl-5-[3-(4-methyl phenyl)-3H-imidazo[4,5-c]pyridin-2-yl]pyrimidin-2-amine

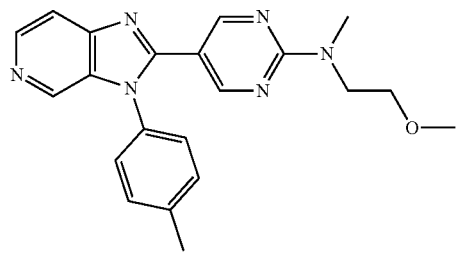 [SMILES: COCCN(C)c1ncc(-c2nc3ccncc3n2-c2ccc(C)cc2)cn1]

Intermediate 107 (crude) was dissolved in NMP (2 mL), Et₃N (633 uL, 4.54 mmol) was added and the reaction mixture was heated at 180° C. in a microwave reactor for 30 min. The reaction mixture was partitioned between DCM (15 mL) and water (15 mL) and the organic fraction was washed with brine (15 mL), dried (MgSO₄) and concentrated in vacuo. The residue was triturated from MeOH to give the title compound as an off white solid (60.3 mg, 10.6%). HRMS (ESI⁺) calcd for [MH]⁺ of $C_{21}H_{22}N_6O$ 375.1933 found 375.1942. HPLC: Rt: 4.99 min, 99.3% purity.

Examples 118-119

Examples 118-119 were prepared similarly to Example 117, by cyclisation of Intermediates 111 and 113; see Table 17 below.

TABLE 17

Cyclisation of Intermediates 111 and 113

| Ex | Structure | Name | Intermediate(s) used, Form, Yield, LCMS, HPLC |
|---|---|---|---|
| 118 | 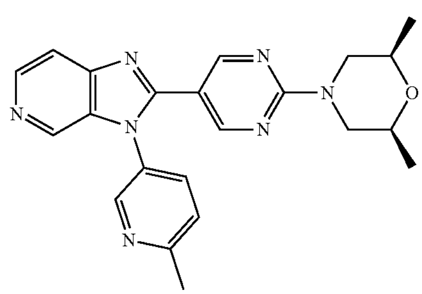 [SMILES: Cc1ccc(-n2c(-c3cnc(N4C[C@@H](C)O[C@@H](C)C4)nc3)nc3ccncc32)cn1] | (2R,6S)-2,6-Dimethyl-4-{5-[3-(6-methylpyridin-3-yl)-3H-imidazo[4,5-c]pyridin-2-yl]pyrimidin-2-yl}morpholine | From Intermediate 111 White solid Yield 58.0 mg, 7.23% HRMS (ESI⁺) calcd for [MH]⁺ of $C_{22}H_{23}N_7O$ 402.2042 found 402.2046. HPLC: Rt 4.52 min, 97.6% purity |
| 119 | 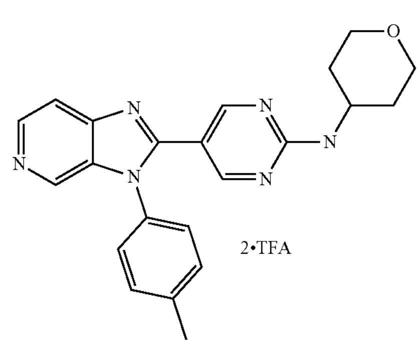 [SMILES: Cc1ccc(-n2c(-c3cnc(NC4CCOCC4)nc3)nc3ccncc32)cc1] | 5-[3-(4-Methylphenyl)-3H-imidazo[4,5-c]pyridin-2-yl]-N-(oxan-4-yl)pyrimidin-2-amine; bis(trifluoroacetic acid) | From Intermediate 113 White solid Yield 12.0 mg, 1.55% HRMS (ESI⁺) calcd for [MH]⁺ of $C_{22}H_{22}N_6O$ 387.1933 found 387.1936. HPLC: Rt 4.42 min, 99.4% purity |

Example 120

4-[1-(4-Chlorophenyl)-1H-pyrrolo[2,3-c]pyridin-2-yl]pyridine

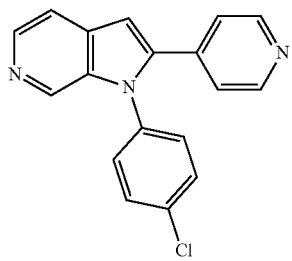 [SMILES: Clc1ccc(-n2c(-c3ccncc3)cc3ccncc32)cc1]

Intermediate 134 (100 mg, 0.437 mmol) and triisopropyl borate (212 uL, 0.918 mmol) were dissolved in THF (5 mL) and the reaction mixture was cooled to 0° C. LDA (435 uL, 2.0M in THF/heptane, 0.875 mmol) was added and the reaction mixture was stirred at 0 for 30 min. The reaction was quenched with water (2 mL) and diluted with dioxane (3 mL). 4-Iodopyridine (108 mg, 0.525 mmol), Pd(PPh$_3$)$_4$ (40.4 mg, 35.0 umol) and a solution of Na$_2$CO$_3$ (139 mg, 1.31 mmol) in water (4 mL) were added. The reaction mixture was heated using a microwave reactor at 160° C. for 20 min. The reaction mixture was partitioned between water (40 mL) and EtOAc (40 mL), and the organic fraction was dried (MgSO$_4$) and concentrated in vacuo. The residue was purified by reverse phase HPLC to give the title compound as a light yellow solid (21.8 mg, 16.3%). HRMS (ESI$^+$) calcd for [MH]$^+$ of C$_{18}$H$_{12}$ClN$_3$ 306.0798 found 306.0809. HPLC: Rt 3.52 min, 99.9% purity.

Examples 121-154

Examples 121-154 were prepared similarly to Example 120, by borate formation and Suzuki reaction of Intermediates 134-138 with the appropriate aryl or heteroaryl iodide or bromide; see Table 18 below.

TABLE 18

Borate formation and Suzuki reactions of Intermediates 134-138

| Ex | Structure | Name | Intermediate(s), Form, Yield, LCMS, HPLC |
|---|---|---|---|
| 121 | 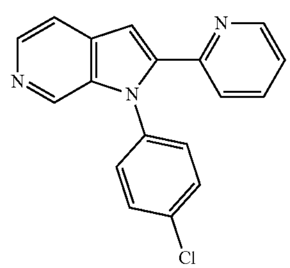 [SMILES: Clc1ccc(-n2c(-c3ccccn3)cc3ccncc32)cc1] | 2-[1-(4-Chlorophenyl)-1H-pyrrolo[2,3-c]pyridin-2-yl]pyridine | From Intermediate 134<br>Yellow gum<br>Yield 14.0 mg, 6.98%<br>HRMS (ESI$^+$) calcd for [MH]$^+$ of C$_{18}$H$_{12}$ClN$_3$ 306.0798 found 306.0811.<br>HPLC: Rt 4.82 min, 99.1% purity |
| 122 | 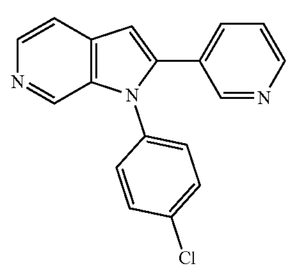 | 3-[1-(4-Chlorophenyl)-1H-pyrrolo[2,3-c]pyridin-2-yl]pyridine | From Intermediate 134<br>Yellow gum<br>Yield 13.1 mg, 9.80%<br>HRMS (ESI$^+$) calcd for [MH]$^+$ of C$_{18}$H$_{12}$ClN$_3$ 306.0798 found 306.0810.<br>HPLC: Rt 3.95 min, 99.1% purity |

TABLE 18-continued

Borate formation and Suzuki reactions of Intermediates 134-138

| Ex | Structure | Name | Intermediate(s), Form, Yield, LCMS, HPLC |
|---|---|---|---|
| 123 | 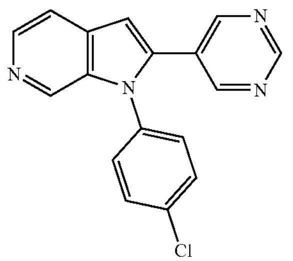 [SMILES: Clc1ccc(-n2c(-c3cncnc3)cc3ccncc32)cc1] | 5-[1-(4-Chlorophenyl)-1H-pyrrolo[2,3-c]pyridin-2-yl]pyrimidine | From Intermediate 134<br>White solid<br>Yield 64.9 mg, 32.2%<br>HRMS (ESI+) calcd for [MH]+ of $C_{17}H_{11}ClN_4$ 307.0750 found 307.0753.<br>HPLC: Rt 4.24 min, 99.1% purity |
| 124 | 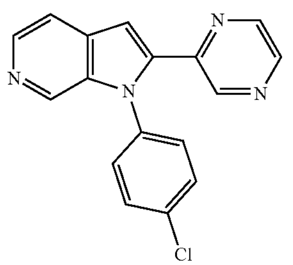 [SMILES: Clc1ccc(-n2c(-c3cnccn3)cc3ccncc32)cc1] | 2-[1-(4-Chlorophenyl)-1H-pyrrolo[2,3-c]pyridin-2-yl]pyrazine | From Intermediate 134<br>Yellow gum<br>Yield 28.0 mg, 13.9%<br>HRMS (ESI+) calcd for [MH]+ of $C_{17}H_{11}ClN_4$ 307.0750 found 307.0764.<br>HPLC: Rt 4.53 min, 99.7% purity |
| 125 | 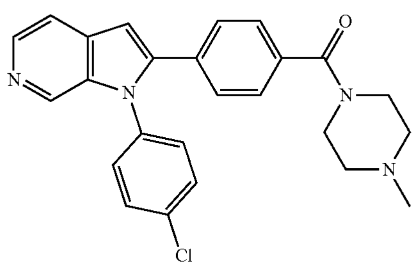 [SMILES: CN1CCN(C(=O)c2ccc(-c3cc4ccncc4n3-c3ccc(Cl)cc3)cc2)CC1] | 1-({4-[1-(4-Chlorophenyl)-1H-pyrrolo[2,3-c]pyridin-2-yl]phenyl}carbonyl)-4-methylpiperazine | From Intermediate 134 and 139<br>Yellow solid<br>Yield 23.0 mg, 8.14%<br>HRMS (ESI+) calcd for [MH]+ of $C_{25}H_{23}ClN_4O$ 431.1638 found 431.1638.<br>HPLC: Rt 3.77 min, 97.9% purity |
| 126 | 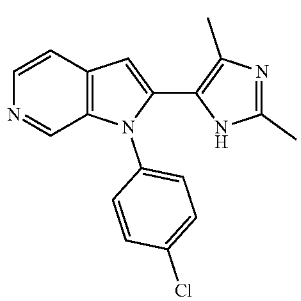 [SMILES: Cc1nc(C)c(-c2cc3ccncc3n2-c2ccc(Cl)cc2)[nH]1] | 5-[1-(4-Chlorophenyl)-1H-pyrrolo[2,3-c]pyridin-2-yl]-2,4-dimethyl-1H-imidazole | From Intermediate 134<br>Off white solid<br>Yield 14.6 mg, 6.90%<br>HRMS (ESI+) calcd for [MH]+ of $C_{18}H_{15}ClN_4$ 323.1063 found 323.1067.<br>HPLC: Rt 3.45 min, 100% purity |

TABLE 18-continued

Borate formation and Suzuki reactions of Intermediates 134-138

| Ex | Structure | Name | Intermediate(s), Form, Yield, LCMS, HPLC |
|---|---|---|---|
| 127 | 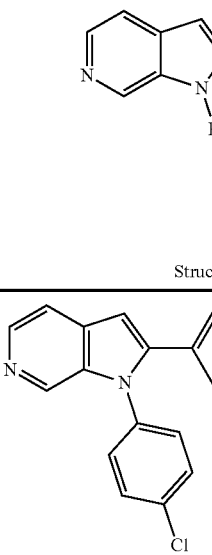 | 4-{5-[1-(4-Chlorophenyl)-1H-pyrrolo[2,3-c]pyridin-2-yl]pyrimidin-2-yl}morpholine | From Intermediate 134<br>Yellow solid<br>Yield 67.2 mg, 19.6%<br>HRMS (ESI$^+$) calcd for [MH]$^+$ of $C_{21}H_{18}ClN_5O$ 392.1278 found 392.1286.<br>HPLC: Rt 5.12 min, 100% purity |
| 128 | 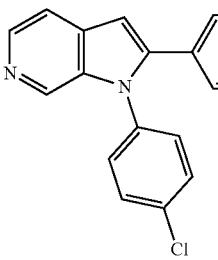 | 4-{5-[1-(4-Chlorophenyl)-1H-pyrrolo[2,3-c]pyridin-2-yl]pyrimidin-2-yl}piperazin-2-one | From Intermediate 134 and 140<br>White solid<br>Yield 71.5 mg, 16.1%<br>HRMS (ESI$^+$) calcd for [MH]$^+$ of $C_{21}H_{17}ClN_6O$ 405.1230 found 405.1226.<br>HPLC: Rt 4.23 min, 98.6% purity. |
| 129 | 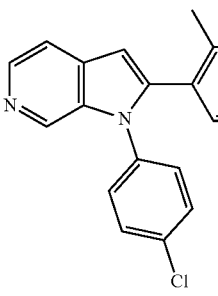 | 4-{5-[1-(4-Chlorophenyl)-1H-pyrrolo[2,3-c]pyridin-2-yl]-4-methylpyridin-2-yl}morpholine; bis(trifluoroacetic acid) | From Intermediate 134 and 143<br>Colourless gum<br>Yield 6.55 mg, 0.95%<br>HRMS (ESI$^+$) calcd for [MH]$^+$ of $C_{23}H_{21}ClN_4O$ 405.1482 found 405.1494.<br>HPLC: Rt 4.06 min, 98.6% purity. |
| 130 | 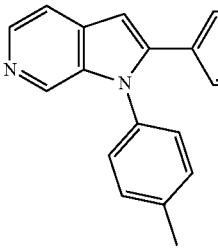 | 4-{5-[1-(4-Methylphenyl)-1H-pyrrolo[2,3-c]pyridin-2-yl]pyrimidin-2-yl}morpholine | From Intermediate 135<br>White solid<br>Yield 80.0 mg, 17.9%<br>HRMS (ESI$^+$) calcd for [MH]$^+$ of $C_{22}H_{21}N_5O$ 372.1824 found 372.1828.<br>HPLC: Rt 5.21 min, 100% purity. |
| 131 | 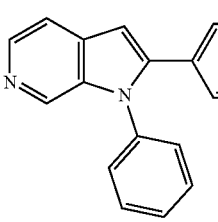 | 4-(5-{1-Phenyl-1H-pyrrolo[2,3-c]pyridin-2-yl}pyrimidin-2-yl)morpholine | From Intermediate 136<br>White solid<br>Yield 58.5 mg, 12.7%<br>HRMS (ESI$^+$) calcd for [MH]$^+$ of $C_{21}H_{19}N_5O$ 358.1668 found 358.1685.<br>HPLC: Rt 4.90 min, 97.4% purity. |

TABLE 18-continued

Borate formation and Suzuki reactions of Intermediates 134-138

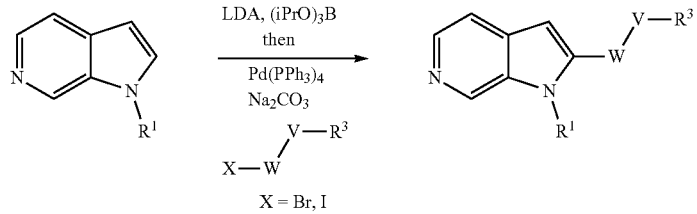

| Ex | Structure | Name | Intermediate(s), Form, Yield, LCMS, HPLC |
|---|---|---|---|
| 132 | 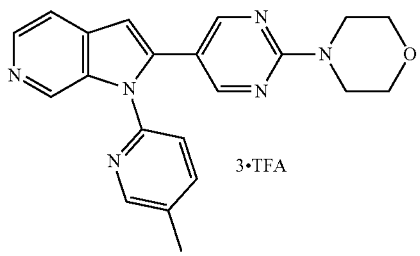 [SMILES: Cc1ccc(-n2c(-c3cnc(N4CCOCC4)nc3)cc3ccncc32)nc1] | 4-{5-[1-(5-Methylpyridin-2-yl)-1H-pyrrolo[2,3-c]pyridin-2-yl]pyrimidin-2-yl}morpholine; tris(trifluoroacetic acid) | From Intermediate 137<br>Yellow solid<br>Yield 3.35 mg, 0.87%<br>HRMS (ESI+) calcd for [MH]+ of $C_{21}H_{20}N_6O$ 373.1777 found 373.1794.<br>HPLC: Rt 4.68 min, 99.6% purity. |
| 133 | 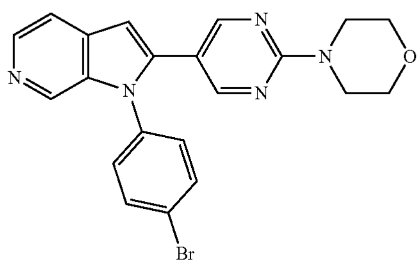 [SMILES: Brc1ccc(-n2c(-c3cnc(N4CCOCC4)nc3)cc3ccncc32)cc1] | 4-{5-[1-(4-Bromophenyl)-1H-pyrrolo[2,3-c]pyridin-2-yl]pyrimidin-2-yl}morpholine | From Intermediate 138<br>Light yellow solid<br>Yield 38.0 mg, 9.52%<br>HRMS (ESI+) calcd for [MH]+ of $C_{21}H_{18}BrN_5O$ 436.0773 found 436.0773.<br>HPLC: Rt 5.32 min, 96.2% purity. |
| 134 | 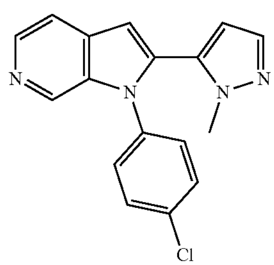 [SMILES: Cn1nccc1-c1cc2ccncc2n1-c1ccc(Cl)cc1] | 5-[1-(4-Chlorophenyl)-1H-pyrrolo[2,3-c]pyridin-2-yl]-1-methyl-1H-pyrazole | From Intermediate 134<br>Orange solid<br>Yield 133 mg, 32.8%<br>HRMS (ESI+) calcd for [MH]+ of $C_{17}H_{13}ClN_4$ 309.0907 found 309.0918.<br>HPLC: Rt 4.64 min, 98.4% purity. |
| 135 | 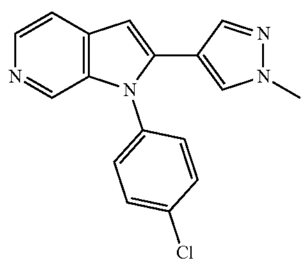 [SMILES: Cn1cc(-c2cc3ccncc3n2-c2ccc(Cl)cc2)cn1] | 4-[1-(4-Chlorophenyl)-1H-pyrrolo[2,3-c]pyridin-2-yl]-1-methyl-1H-pyrazole | From Intermediate 134<br>Orange solid<br>Yield 153 mg, 37.9%<br>HRMS (ESI+) calcd for [MH]+ of $C_{17}H_{13}ClN_4$ 309.0907 found 309.0910.<br>HPLC: Rt 4.87 min, 99.5% purity. |

TABLE 18-continued

Borate formation and Suzuki reactions of Intermediates 134-138

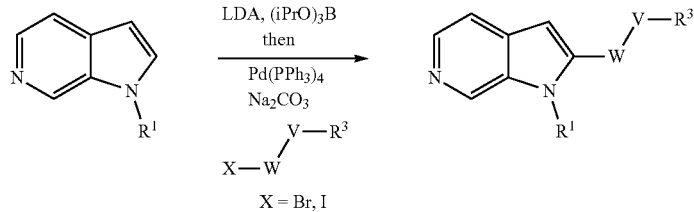

| Ex | Structure | Name | Intermediate(s), Form, Yield, LCMS, HPLC |
|---|---|---|---|
| 136 | 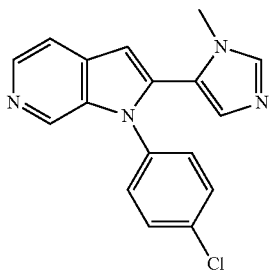 [SMILES: Cn1cncc1-c1cc2ccncc2n1-c1ccc(Cl)cc1] | 5-[1-(4-Chlorophenyl)-1H-pyrrolo[2,3-c]pyridin-2-yl]-1-methyl-1H-imidazole | From Intermediate 134<br>White solid<br>Yield 63.8 mg, 15.8%<br>HRMS (ESI$^+$) calcd for [MH]$^+$ of $C_{17}H_{13}ClN_4$ 309.0907 found 309.0914.<br>HPLC: Rt 3.43 min, 100% purity. |
| 137 | 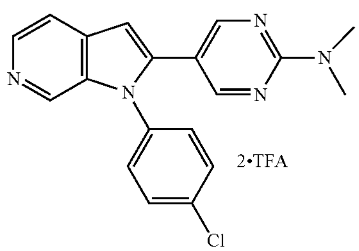 [SMILES: CN(C)c1ncc(-c2cc3ccncc3n2-c2ccc(Cl)cc2)cn1] | 5-[1-(4-Chlorophenyl)-1H-pyrrolo[2,3-c]pyridin-2-yl]-N,N-dimethylpyrimidin-2-amine; bis(trifluoroacetic acid) | From Intermediate 134<br>Yellow gum<br>Yield 142 mg, 18.7%<br>HRMS (ESI$^+$) calcd for [MH]$^+$ of $C_{19}H_{16}ClN_5$ 350.1172 found 350.1180.<br>HPLC: Rt 5.46 min, 100% purity. |
| 138 | 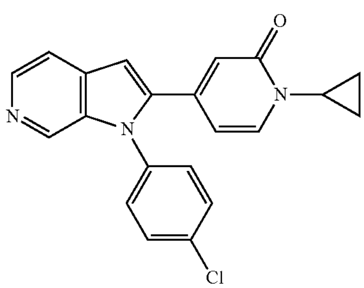 [SMILES: O=c1cc(-c2cc3ccncc3n2-c2ccc(Cl)cc2)ccn1C1CC1] | 4-[1-(4-Chlorophenyl)-1H-pyrrolo[2,3-c]pyridin-2-yl]-1-cyclopropyl-1,2-dihydropyridin-2-one | From Intermediate 134 and 144<br>Yellow solid<br>Yield 234 mg, 36.9%<br>HRMS (ESI$^+$) calcd for [MH]$^+$ of $C_{21}H_{16}ClN_3O$ 362.1060 found 362.1063.<br>HPLC: Rt 4.76 min, 99.0% purity. |
| 139 | 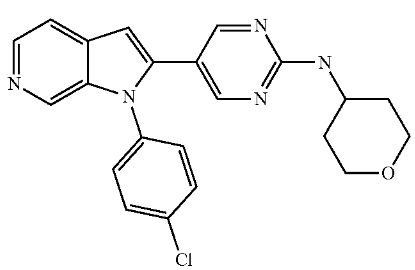 [SMILES: Clc1ccc(-n2c(-c3cnc(NC4CCOCC4)nc3)cc3ccncc32)cc1] | 5-[1-(4-Chlorophenyl)-1H-pyrrolo[2,3-c]pyridin-2-yl]-N-(oxan-4-yl)pyrimidin-2-amine | From Intermediate 134 and 141<br>White solid<br>Yield 122 mg, 22.8%<br>HRMS (ESI$^+$) calcd for [MH]$^+$ of $C_{22}H_{20}ClN_5O$ 406.1435 found 406.1435.<br>HPLC: Rt 4.78 min, 99.3% purity. |

TABLE 18-continued

Borate formation and Suzuki reactions of Intermediates 134-138

| Ex | Structure | Name | Intermediate(s), Form, Yield, LCMS, HPLC |
|---|---|---|---|
| 140 | 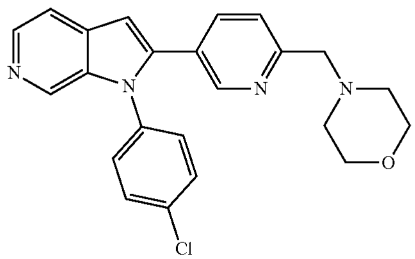 [SMILES: Clc1ccc(-n2c(-c3ccc(CN4CCOCC4)nc3)cc3ccncc32)cc1] | 4-({5-[1-(4-Chlorophenyl)-1H-pyrrolo[2,3-c]pyridin-2-yl]pyridin-2-yl}methyl)morpholine | From Intermediate 134 and 145<br>Beige solid<br>Yield 29.7 mg, 4.20%<br>HRMS (ESI+) calcd for [MH]+ of $C_{23}H_{21}ClN_4O$ 405.1482 found 405.1485.<br>HPLC: Rt 3.91 min, 98.0% purity. |
| 141 | 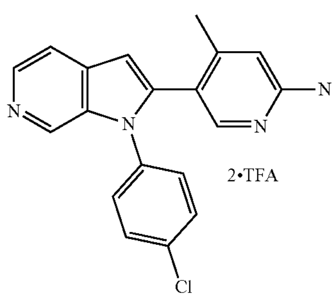 [SMILES: Cc1cc(N)ncc1-c1cc2ccncc2n1-c1ccc(Cl)cc1] | 5-[1-(4-Chlorophenyl)-1H-pyrrolo[2,3-c]pyridin-2-yl]-4-methylpyridin-2-amine; bis(trifluoroacetic acid) | From Intermediate 134<br>Colourless gum<br>Yield 1.68 mg, 0.34%<br>LCMS (ES+): 335.1 [MH]+<br>HPLC: Rt 3.63 min, 96.8% purity. |
| 142 | 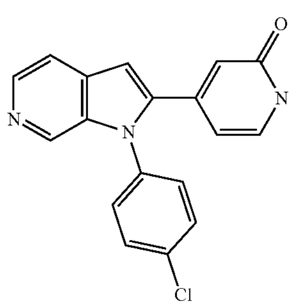 [SMILES: O=c1cc(-c2cc3ccncc3n2-c2ccc(Cl)cc2)cc[nH]1] | 4-[1-(4-Chlorophenyl)-1H-pyrrolo[2,3-c]pyridin-2-yl]-1,2-dihydropyridin-2-one | From Intermediate 134<br>Off white solid<br>Yield 52.0 mg, 14.8%<br>HRMS (ESI+) calcd for [MH]+ of $C_{18}H_{12}ClN_3O$ 322.0747 found 322.0753.<br>HPLC: Rt 3.75 min, 97.6% purity. |
| 143 | 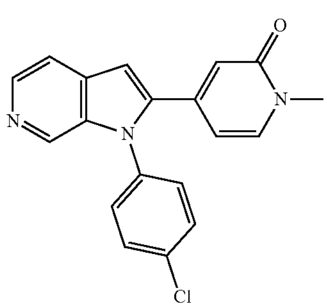 [SMILES: Cn1ccc(-c2cc3ccncc3n2-c2ccc(Cl)cc2)cc1=O] | 4-[1-(4-Chlorophenyl)-1H-pyrrolo[2,3-c]pyridin-2-yl]-1-methyl-1,2-dihydropyridin-2-one | From Intermediate 134 and 146<br>Off white solid<br>Yield 56.9 mg, 15.5%<br>HRMS (ESI+) calcd for [MH]+ of $C_{19}H_{14}ClN_3O$ 336.0904 found 336.0909.<br>HPLC: Rt 4.07 min, 98.6% purity. |

TABLE 18-continued

Borate formation and Suzuki reactions of Intermediates 134-138

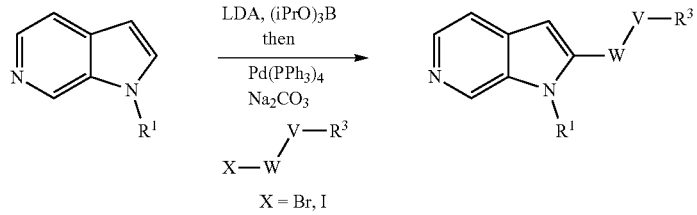

| Ex | Structure | Name | Intermediate(s), Form, Yield, LCMS, HPLC |
|----|-----------|------|------------------------------------------|
| 144 | 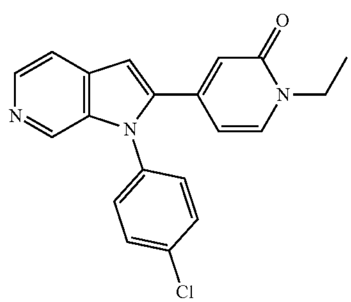 [SMILES: CCn1ccc(-c2cc3ccncc3n2-c2ccc(Cl)cc2)cc1=O] | 4-[1-(4-Chlorophenyl)-1H-pyrrolo[2,3-c]pyridin-2-yl]-1-ethyl-1,2-dihydropyridin-2-one | From Intermediate 134 and 147<br>Off white solid<br>Yield 59.5 mg, 15.6%<br>HRMS (ESI$^+$) calcd for [MH]$^+$ of $C_{20}H_{16}ClN_3O$ 350.1060 found 350.1065.<br>HPLC: Rt 4.39 min, 100% purity. |
| 145 | 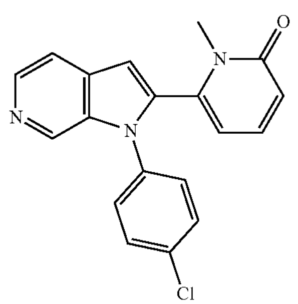 [SMILES: Cn1c(-c2cc3ccncc3n2-c2ccc(Cl)cc2)cccc1=O] | 6-[1-(4-Chlorophenyl)-1H-pyrrolo[2,3-c]pyridin-2-yl]-1-methyl-1,2-dihydropyridin-2-one | From Intermediate 134 and 148<br>White solid<br>Yield 82.2 mg, 16.0%<br>HRMS (ESI$^+$) calcd for [MH]$^{1+}$ of $C_{19}H_{14}ClN_3O$ 336.0904 found 336.0914.<br>HPLC: Rt 4.20 min, 99.5% purity. |
| 146 | 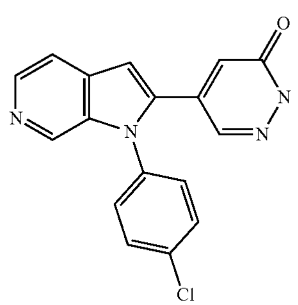 [SMILES: O=c1cc(-c2cc3ccncc3n2-c2ccc(Cl)cc2)cn[nH]1] | 5-[1-(4-Chlorophenyl)-1H-pyrrolo[2,3-c]pyridin-2-yl]-2,3-dihydropyridazin-3-one | From Intermediate 134<br>Yellow solid<br>Yield 35.5 mg, 10.1%<br>HRMS (ESI$^+$) calcd for [MH]$_+$ of $C_{17}H_{11}ClN_4O$ 323.0699 found 323.0700.<br>HPLC: Rt 3.86 min, 98.4% purity. |
| 147 | 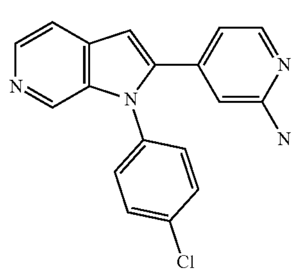 [SMILES: Nc1cc(-c2cc3ccncc3n2-c2ccc(Cl)cc2)ccn1] | 4-[1-(4-Chlorophenyl)-1H-pyrrolo[2,3-c]pyridin-2-yl]pyridin-2-amine | From Intermediate 134<br>Off white solid<br>Yield 103 mg, 29.4%<br>HRMS (ESI$^+$) calcd for [MH]$^+$ of $C_{18}H_{13}ClN_4$ 321.0907 found 321.0901.<br>HPLC: Rt 3.56 min, 100% purity. |

TABLE 18-continued

Borate formation and Suzuki reactions of Intermediates 134-138

| Ex | Structure | Name | Intermediate(s), Form, Yield, LCMS, HPLC |
|---|---|---|---|
| 148 | 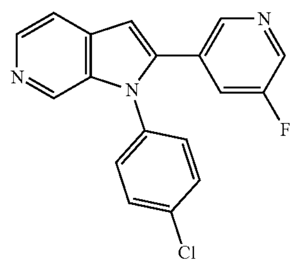 [SMILES: Fc1cncc(-c2cc3ccncc3n2-c2ccc(Cl)cc2)c1] | 3-[1-(4-Chlorophenyl)-1H-pyrrolo[2,3-c]pyridin-2-yl]-5-fluoropyridine | From Intermediate 134<br>Yellow solid<br>Yield 21.2 mg, 6.00%<br>HRMS (ESI$^+$) calcd for [MH]$^+$ of $C_{18}H_{11}ClFN_3$ 324.0704 found 324.0714.<br>HPLC: Rt 4.87 min, 100% purity. |
| 149 | 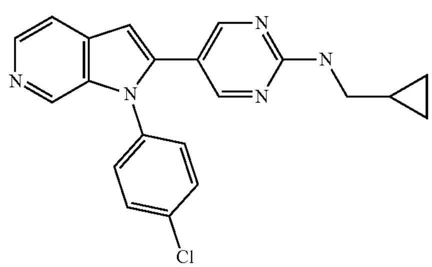 [SMILES: Clc1ccc(-n2c(-c3cnc(NCC4CC4)nc3)cc3ccncc32)cc1] | 5-[1-(4-Chlorophenyl)-1H-pyrrolo[2,3-c]pyridin-2-yl]-N-(cyclopropylmethyl)pyrimidin-2-amine | From Intermediate 134 and 142<br>Off white solid<br>Yield 32.0 mg, 7.79%<br>HRMS (ESI$^+$) calcd for [MH]$^+$ of $C_{21}H_{18}ClN_5$ 376.1329 found 376.1326.<br>HPLC: Rt 5.38 min, 99.1% purity. |
| 150 | 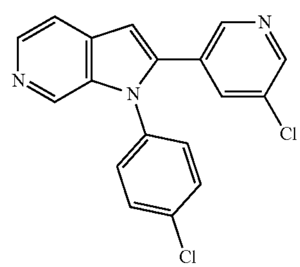 [SMILES: Clc1ccc(-n2c(-c3cncc(Cl)c3)cc3ccncc32)cc1] | 3-Chloro-5-[1-(4-chlorophenyl)-1H-pyrrolo[2,3-c]pyridin-2-yl]pyridine | From Intermediate 134<br>Off white solid<br>Yield 19.2 mg, 5.16%<br>HRMS (ESI$^+$) calcd for [MH]$^+$ of $C_{18}H_{11}Cl_2N_3$ 340.0408 found 340.0418.<br>HPLC: Rt 5.17 min, 100% purity. |
| 151 | 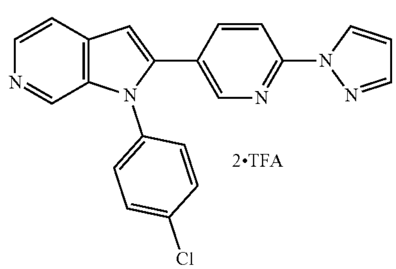 [SMILES: Clc1ccc(-n2c(-c3ccc(-n4cccn4)nc3)cc3ccncc32)cc1] | 5-[1-(4-Chlorophenyl)-1H-pyrrolo[2,3-c]pyridin-2-yl]-2-(1H-pyrazol-1-yl)pyridine; bis(trifluoroacetic acid) | From Intermediate 134<br>Yellow solid<br>Yield 4.51 mg, 0.69%<br>HRMS (ESI$^+$) calcd for [MH]$^+$ of $C_{21}H_{14}ClN_5$ 372.1016 found 372.1025.<br>HPLC: Rt 5.57 min, 100% purity. |

TABLE 18-continued

Borate formation and Suzuki reactions of Intermediates 134-138

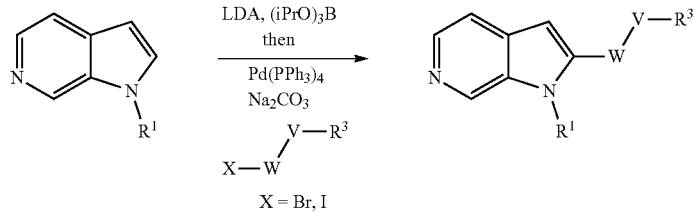

| Ex | Structure | Name | Intermediate(s), Form, Yield, LCMS, HPLC |
|---|---|---|---|
| 152 | 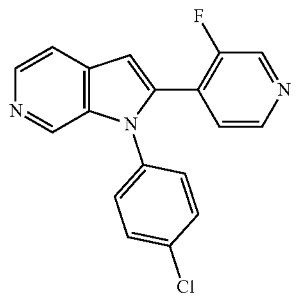 | 4-[1-(4-Chlorophenyl)-1H-pyrrolo[2,3-c]pyridin-2-yl]-3-fluoropyridine | From Intermediate 134<br>White solid<br>Yield 9.24 mg, 2.61%<br>HRMS (ESI+) calcd for [MH]+ of $C_{18}H_{11}ClFN_3$ 324.0704 found 324.0710.<br>HPLC: Rt 4.74 min, 100% purity. |
| 153 | 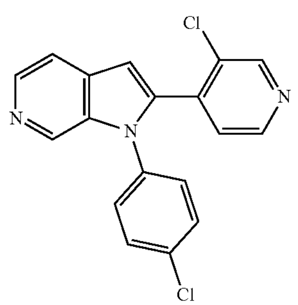 [SMILES: Fc1cnccc1-c1cc2ccncc2n1-c1ccc(Cl)cc1] | 3-Chloro-4-[1-(4-chlorophenyl)-1H-pyrrolo[2,3-c]pyridin-2-yl]pyridine | From Intermediate 134<br>White solid<br>Yield 40.1 mg, 9.29%<br>HRMS (ESI+) calcd for [MH]+ of $C_{18}H_{11}Cl_2N_3$ 340.0408 found 340.0421.<br>HPLC: Rt 4.98 min, 100% purity. |
| 154 | 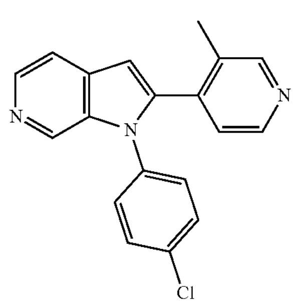 [SMILES: Cc1cnccc1-c1cc2ccncc2n1-c1ccc(Cl)cc1] | 4-[1-(4-Chlorophenyl)-1H-pyrrolo[2,3-c]pyridin-2-yl]-3-methylpyridine | From Intermediate 134<br>White solid<br>Yield 29.5 mg, 8.45%<br>HRMS (ESI+) calcd for [MH]+ of $C_{19}H_{14}ClN_3$ 320.0954 found 320.0958.<br>HPLC: Rt 3.71 min, 100% purity. |

Example 155

1-Cyclopropyl-4-{1-phenyl-1H-pyrrolo[2,3-c]pyridin-2-yl}-1,2-dihydropyridin-2-one

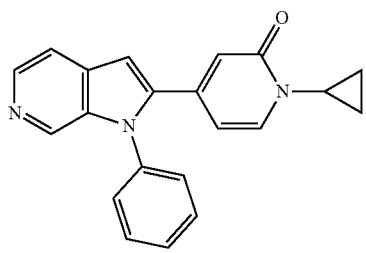 [SMILES: O=c1cc(-c2cc3ccncc3n2-c2ccccc2)ccn1C1CC1]

Example 138 (50.0 mg, 0.138 mmol) was dissolved in MeOH (15 mL) and passed through an H-cube (70×4 mm 10% Pd/C CatCart, 1.0 mL/min, 30° C., 2 0 bar). The solvents were removed in vacuo and the residue purified by reverse phase HPLC to give the title compound (0.610 mg, 1.35%) as a colourless gum. LCMS (ES$^+$): 328.0 [MH]$^+$. HPLC: Rt 4.50 min, 96.7% purity.

Biological Tests

Biological Assays of the SSAO Enzyme Inhibitors

All primary assays were performed at RT. with purified recombinantly expressed human SSAO. Enzyme was prepared essentially as described in Öhman et al. (Protein Expression and Purification 46 (2006) 321-331). In addition, secondary- and selectivity assays were performed using SSAO prepared from various tissues or purified rat recombinant SSAO. The enzyme activity was assayed with benzylamine as substrate by measuring either benzaldehyde production, using $^{14}$C-labeled substrate, or by utilizing the production of hydrogen peroxide in a horseradish peroxidase (HRP) coupled reaction. Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer yielded a final DMSO concentration ≤2%.

Hydrogen Peroxide Detection:

In a horseradish peroxidase (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidase Assay kit, Invitrogen A22188). Enzyme and compounds in 50 mM sodium phosphate, pH 7.4 were set to pre-incubate in flat-bottomed microtiter plates for approximately 15 min before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 h, exciting at 544 nm and reading the emission at 590 nm. For the human SSAO assay final concentrations of the reagents in the assay wells were: SSAO enzyme 1 ug/ml, benzylamine 100 uM, Amplex reagent 20 uM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and IC$_{50}$ values were calculated using the GraphPad Prism 4 or XLfit 4 programs.

Aldehyde Detection:

SSAO activity was assayed using 14C-labeled benzylamine and analysed by measuring radioactive benzaldehyde. In a white 96-well optiplate (Packard), 20 uL of diluted test compound was pre-incubated at room temperature with 20 uL SSAO enzyme for approximately 15 min with continuous agitation. All dilutions were made with PBS. The reaction was initiated by adding 20 uL of the benzylamine substrate solution containing [7-14C] Benzylamine hydrochloride (CFA589, GE Healthcare). The plate was incubated for 1 h as above after which the reaction was stopped by acidification (10 uL 1M aq HCl). Then 90 uL Micro Scint-E solution (Perkin-Elmer) was added to each well and the plate was continuously mixed for 15 min. Phase separation occurred instantly and activity was read in a Topcount scintillation counter (Perkin-Elmer). In the final reaction well, the human recombinant SSAO concentration was 10 ug/ml. In order to optimize sensitivity, the substrate concentration was decreased as compared to the HRP coupled assay in order to get a higher fraction of radioactive product. In the human SSAO assay, benzylamine concentration was 40 uM (0.2 uCi/mL). Data was analysed as above.

All of the exemplified compounds of the invention had an IC$_{50}$ value of between 1 nM and 1200 nM at SSAO (see Table 19 below).

TABLE 19

| SSAO inhibitory activity (A: <50 nM, B: 50-200 nM, C: 200-1200 nM) | |
|---|---|
| Compound | SSAO IC$_{50}$ (nM) |
| 1 | C |
| 2 | C |
| 3 | B |
| 4 | A |
| 5 | B |
| 6 | C |
| 7 | B |
| 8 | A |
| 9 | A |
| 10 | B |
| 11 | A |
| 12 | B |
| 13 | A |
| 14 | C |
| 15 | B |
| 16 | C |
| 17 | C |
| 18 | B |
| 19 | B |
| 20 | B |
| 21 | A |
| 22 | A |
| 23 | A |
| 24 | A |
| 25 | A |
| 26 | B |
| 27 | A |
| 28 | B |
| 29 | C |
| 30 | C |
| 31 | C |
| 32 | A |
| 33 | C |
| 34 | B |
| 35 | C |

TABLE 19-continued

SSAO inhibitory activity (A: <50 nM, B: 50-200 nM, C: 200-1200 nM)

| Compound | SSAO IC$_{50}$ (nM) |
|---|---|
| 36 | B |
| 37 | A |
| 38 | B |
| 39 | A |
| 40 | B |
| 41 | A |
| 42 | B |
| 43 | A |
| 44 | C |
| 45 | C |
| 46 | A |
| 47 | A |
| 48 | A |
| 49 | A |
| 50 | A |
| 51 | A |
| 52 | A |
| 53 | C |
| 54 | C |
| 55 | A |
| 56 | C |
| 57 | B |
| 58 | C |
| 59 | B |
| 60 | B |
| 61 | A |
| 62 | B |
| 63 | C |
| 64 | C |
| 65 | A |
| 66 | B |
| 67 | A |
| 68 | A |
| 69 | A |
| 70 | A |
| 71 | C |
| 72 | C |
| 73 | B |
| 74 | C |
| 75 | A |
| 76 | B |
| 77 | C |
| 78 | A |
| 79 | A |
| 80 | B |
| 81 | A |
| 82 | A |
| 83 | A |
| 84 | A |
| 85 | A |
| 86 | A |
| 87 | A |
| 88 | A |
| 89 | A |
| 90 | A |
| 91 | C |
| 92 | A |
| 93 | B |
| 94 | C |
| 95 | B |
| 96 | B |
| 97 | C |
| 98 | B |
| 99 | A |
| 100 | C |
| 101 | B |
| 102 | B |
| 103 | B |
| 104 | A |
| 105 | C |
| 106 | B |
| 107 | A |
| 108 | C |
| 109 | C |
| 110 | C |
| 111 | C |
| 112 | A |
| 113 | A |
| 114 | C |
| 115 | A |
| 116 | B |
| 117 | C |
| 118 | A |
| 119 | B |
| 120 | C |
| 121 | A |
| 122 | B |
| 123 | A |
| 124 | A |
| 125 | C |
| 126 | A |
| 127 | A |
| 128 | A |
| 129 | A |
| 130 | B |
| 131 | C |
| 132 | B |
| 133 | A |
| 134 | A |
| 135 | A |
| 136 | A |
| 137 | A |
| 138 | A |
| 139 | A |
| 140 | A |
| 141 | B |
| 142 | B |
| 143 | A |
| 144 | B |
| 145 | A |
| 146 | B |
| 147 | A |
| 148 | A |
| 149 | A |
| 150 | B |
| 151 | B |
| 152 | C |
| 153 | B |
| 154 | A |
| 155 | C | hERG Assay

Compounds of the invention were tested for inhibition of the human ether a go-go related gene (hERG) K$^+$ channel using IonWorks patch clamp electrophysiology. 8 Point concentration-response curves were generated on two occasions using 3-fold serial dilutions from the maximum assay concentration (11 uM). Electrophysiological recordings were made from a Chinese Hamster Lung cell line stably expressing the full length hERG channel. Single cell ion currents were measured in the perforated patch clamp configuration (100 ug/mL amphoterocin) at room temperature using an IonWorks Quattro instrument. The internal solution contained 140 mM KCl, 1 mM MgCl$_2$, 1 mM EGTA and 20 mM HEPES and was buffered to pH 7.3. The external solution contained 138 mM NaCl, 2.7 mM KCl, 0.9 mM CaCl$_2$, 0.5 mM MgCl$_2$, 8 mM Na$_2$HPO$_4$ and 1.5 mM KH$_2$PO$_4$, and was buffered to pH 7.3. Cells were clamped at a holding potential of 70 mV for 30 s and then stepped to +40 mV for 1 s. This was followed by a hyperpolarising step of 1 s to 30 mV to evoke the hERG tail current. This sequence was repeated 5 times at a frequency of 0.25 Hz. Currents were measured from the tail step at the 5$^{th}$ pulse, and referenced to the holding current. Compounds were incubated for 6-7 min prior to a second measurement of the hERG signal using an identical pulse train. A minimum of 17 cells were required for each pIC50 curve fit. A control compound (quinidine) was used (see Table 20 below).

TABLE 20 hERG IC50 (A: >10 uM, B: 1-10 uM, C: 0.1 uM-1 uM)

| Compound | hERG IC50 |
|---|---|
| 2 | A |
| 3 | A |
| 4 | B |
| 9 | B |
| 11 | A |
| 12 | A |
| 13 | A |
| 18 | A |
| 20 | A |
| 21 | A |
| 23 | A |
| 24 | A |
| 46 | A |
| 47 | B |
| 48 | B |
| 50 | A |
| 51 | B |
| 52 | A |
| 53 | A |
| 54 | A |
| 57 | A |
| 63 | A |
| 64 | A |
| 67 | B |
| 69 | A |
| 70 | A |
| 71 | A |
| 75 | A |
| 77 | A |
| 78 | A |
| 80 | A |
| 81 | A |
| 82 | A |
| 85 | A |
| 86 | A |
| 88 | B |
| 89 | A |
| 91 | A |
| 92 | A |
| 95 | A |
| 98 | A |
| 110 | A |
| 117 | A |
| 120 | B |
| 122 | B |
| 127 | C |
| 128 | A |
| 130 | C |
| 131 | B |
| 132 | C |
| 136 | B |
| 138 | B |
| 139 | C |
| 140 | B |
| 142 | B |
| 147 | B |
| 152 | B |
| 153 | B |

The invention claimed is:

1. A process for the preparation of a compound of formula (I) or a pharmaceutically acceptable salt, or N-oxide thereof

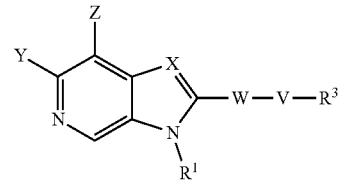

comprising reacting a compound of formula (IIIb) with a compound of formula (IX) to form the compound of formula (I)

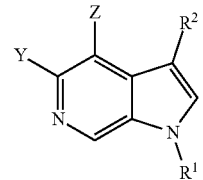

wherein:
Y is selected from hydrogen, hydroxyl, —NH$_2$, —NH—C$_{1-4}$-alkyl, —NH-halo-C$_{1-4}$-alkyl, and —C$_{1-4}$-alkoxy;
Z is selected from hydrogen, halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, and —NHhalo-C$_{1-4}$-alkyl;
R$^1$ is a phenyl ring, or a 5 or 6-membered heteroaryl ring, the ring being optionally substituted with one or more substituents selected from halogen, cyano, C$_{1-4}$-alkyl, halo-C$_{1-4}$-alkyl, cyano-C$_{1-4}$-alkyl, a 3-7 membered cycloalkyl ring, —OR$^5$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$;
R$^{4A}$, R$^{4B}$, R$^5$, and R$^6$ are each independently selected from hydrogen, C$_{1-4}$-alkyl, and halo-C$_{1-4}$-alkyl, or
R$^{4A}$ and R$^{4B}$ together with the nitrogen to which they are attached form a 3-7 membered cyclic amino group, optionally substituted by one or more substituents selected from halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, and —NHhalo-C$_{1-4}$-alkyl;
X is —C(R$^2$)=;
R$^2$ is selected from hydrogen, halogen, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —SO$_2$R$^5$, —SO$_2$NR$^{4A}$R$^{4B}$ and —NR$^6$S(O)$_2$R$^5$;
W is a phenyl ring or a 5 or 6-membered heteroaryl ring, the ring being optionally substituted with one or more substituents selected from halogen, cyano, oxo C$_{1-4}$-alkyl, halo-C$_{1-4}$-alkyl, cyano-C$_{1-4}$-alkyl, —OR$^5$, —NR$^{7A}$R$^{7B}$, —NR$^6$C(O)OR$^5$, —NR$^6$C(O)R$^5$, —NR⁶C(O)NR⁷ᴬR⁷ᴮ, —C(O)NR⁷ᴬR⁷ᴮ, —C(O)R⁵, —C(O)OR⁵, —SO₂R⁵, —SO₂NR⁷ᴬR⁷ᴮ, and —NR⁶S(O)₂R⁵;

R⁷ᴬ and R⁷ᴮ are independently hydrogen, $C_{1-4}$-alkyl, or halo-$C_{1-4}$-alkyl;

V is selected from a bond, —O—, —N(R⁶)—, —(C=O)—, —CONR⁶—, —NR⁶C(O)—, and —$C_{1-4}$-alkylene-, wherein the $C_{1-4}$-alkylene group is optionally substituted by halogen, and wherein any one of the carbon atoms of the $C_{1-4}$-alkylene group may be replaced by —O— or —N(R⁶)—;

R³ is selected from hydrogen, —$C_{1-4}$-alkyl, —$C_{1-4}$-alkyl-$C_{1-4}$-alkoxy, a 3-7 membered heterocyclic ring, a 3-7 membered cycloalkyl ring, and a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —OR⁵, —NR⁴ᴬR⁴ᴮ, —NR⁶C(O)OR⁵, —NR⁶C(O)R⁵, —NR⁶C(O)NR⁴ᴬR⁴ᴮ, —C(O)NR⁴ᴬR⁴ᴮ, —C(O)R⁵, —C(O)OR⁵, —SO₂R⁵, —SO₂NR⁴ᴬR⁴ᴮ, and —NR⁶S(O)₂R⁵;

provided that groups —WVR³ and/or R¹ are not:

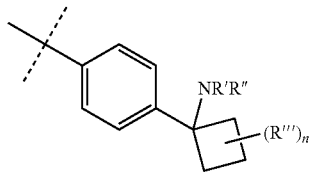

wherein:
n is 0, 1, or 2;
R' and R" are independently selected from the group consisting of H, —$C_1$-$C_6$ alkyl, —(C=O)—$C_1$-$C_6$ alkyl, and —(C=O)OC(CH₃)₃; and
R''' is H, OH, or $C_1$-$C_6$ alkyl; and
further provided that when —R³ is H, R¹ is not a phenyl ring substituted with one —OCH₃.

2. A process for the preparation of a compound of formula (I) or a pharmaceutically acceptable salt, or N-oxide thereof

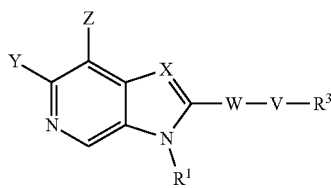 (I)

comprising reacting a compound of formula (IIIb) with a compound of formula (IX) to form the compound of formula (I)

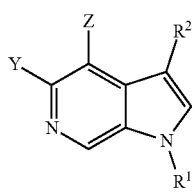 (IIIb)

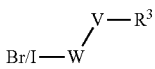 (IX)

wherein:
Y is selected from hydrogen, hydroxyl, —NH₂, —NH—$C_{1-4}$-alkyl, —NH-halo-$C_{1-4}$-alkyl, and —$C_{1-4}$-alkoxy;

Z is selected from hydrogen, halogen, hydroxyl, cyano, $C_{1-4}$-alkyl, halo-$C_{1-4}$-alkyl, $C_{1-4}$-alkoxy, halo-$C_{1-4}$-alkoxy, —CONH₂, —SO₂NH₂, —NH₂, —NHC$_{1-4}$-alkyl, and —NHhalo-$C_{1-4}$-alkyl;

R¹ is a phenyl ring, or a 5 or 6-membered heteroaryl ring, the ring being optionally substituted with one or more substituents selected from halogen, cyano, $C_{1-4}$-alkyl, halo-$C_{1-4}$-alkyl, cyano-$C_{1-4}$-alkyl, —OR⁵, —NR⁶C(O)OR⁵, —NR⁶C(O)R⁵, —NR⁶C(O)NR⁴ᴬR⁴ᴮ, —C(O)NR⁴ᴬR⁴ᴮ, —C(O)R⁵, —C(O)OR⁵, and —NR⁶S(O)₂R⁵;

R⁴ᴬ, R⁴ᴮ, R⁵, and R⁶ are each independently selected from hydrogen, $C_{1-4}$-alkyl, and halo-$C_{1-4}$-alkyl, or R⁴ᴬ and R⁴ᴮ together with the nitrogen to which they are attached form a 3-7 membered cyclic amino group, optionally substituted by one or more substituents selected from halogen, hydroxyl, cyano, $C_{1-4}$-alkyl, halo-$C_{1-4}$-alkyl, $C_{1-4}$-alkoxy, halo-$C_{1-4}$-alkoxy, —CONH₂, —SO₂NH₂, —NH₂, —NHC$_{1-4}$-alkyl, and —NHhalo-$C_{1-4}$-alkyl;

X is —C(R²)=;

R² is selected from hydrogen, halogen, cyano, $C_{1-4}$-alkyl, halo-$C_{1-4}$-alkyl, cyano-$C_{1-4}$-alkyl, —OR⁵, —NR⁴ᴬR⁴ᴮ, —NR⁶C(O)OR⁵, —NR⁶C(O)R⁵, —NR⁶C(O)NR⁴ᴬR⁴ᴮ, —C(O)NR⁴ᴬR⁴ᴮ, —C(O)R⁵, —C(O)OR⁵, —SO₂R⁵, —SO₂NR⁴ᴬR⁴ᴮ, and —NR⁶S(O)₂R⁵, W is a phenyl ring or a 5 or 6-membered heteroaryl ring, the ring being optionally substituted with one or more substituents selected from halogen, cyano, $C_{1-4}$-alkyl, halo-$C_{1-4}$-alkyl, cyano-$C_{1-4}$-alkyl, —OR⁵, —NR⁷ᴬR⁷ᴮ, —NR⁶C(O)OR⁵, —NR⁶C(O)R⁵, —NR⁶C(O)NR⁷ᴬR⁷ᴮ, —SO₂R⁵, —SO₂NR⁷ᴬR⁷ᴮ, and —NR⁶S(O)₂R⁵;

R⁷ᴬ and R⁷ᴮ are independently hydrogen, $C_{1-4}$-alkyl, and halo-$C_{1-4}$-alkyl;

V is selected from a bond, —O—, —N(R⁶)—, —(C=O)—, —CONR⁶—, —NR⁶C(O)—, and —$C_{1-4}$-alkylene-, wherein the $C_{1-4}$-alkylene group is optionally substituted by halogen, and wherein any one of the carbon atoms of the $C_{1-4}$-alkylene group may be replaced by —O— or —N(R⁶)—;

R³ is hydrogen, or a 3-7 membered heterocyclic ring, or 3-7 membered cycloalkyl ring selected from cyclopropyl, cyclopentyl or cyclohexyl, or a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —OR⁵, —NR⁴ᴬR⁴ᴮ, —NR⁶C(O)OR⁵, —NR⁶C(O)R⁵, —NR⁶C(O)NR⁴ᴬR⁴ᴮ, —C(O)NR⁴ᴬR⁴ᴮ, —C(O)R⁵, —C(O)OR⁵, —SO₂R⁵, —SO₂NR⁴ᴬR⁴ᴮ; and —NR⁶S(O)₂R⁵;

provided that when —R³ is H, R¹ is not a phenyl ring substituted with one —OCH₃.

3. The process as claimed in claim 1, wherein the compound of formula (IIIb) is formed by reacting a compound of formula (IIb) with a compound of formula R¹—I

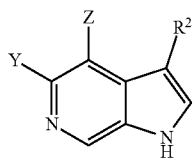

(IIb)

wherein Z, Y, and R¹ are as defined in claim 1.

4. The process as claimed in claim 1, wherein the compound of formula (IIIb) is converted into a boronate ester prior to its reaction with the compound of formula (IX).

5. The process as claimed in claim 4, wherein the boronate ester is formed in a reaction that comprises lithium diisopropylamide and (iPrO)₃B.

6. The process as claimed in claim 4, wherein the compound of formula (I) is formed by reacting the boronate ester of the compound of formula (IIIb) with the compound of formula (IX) under Suzuki coupling conditions.

7. The process as claimed in claim 6, wherein the Suzuki coupling conditions comprise Pd(PPh₃)₄ and Na₂CO₃.

8. The process as claimed in claim 1, wherein the compound of formula (IIIb) is reacted with the compound of formula (IX) in a reaction that comprises lithium diisopropylamide, (iPrO)₃B, Pd(PPh₃)₄, and Na₂CO₃.

9. The process as claimed in claim 3, wherein the compound of formula (IIb) is reacted with the compound R¹—I in the presence of 1,2-dimethylethylenediamine, K₃PO₄, and CuI.

10. The process as claimed in claim 1, wherein Z is hydrogen.

11. The processes as claimed in claim 1, wherein R¹ is phenyl or 6-membered heteroaryl, optionally substituted with one or more substituents selected from halogen, $C_{1-4}$-alkyl, and halo-$C_{1-4}$-alkyl.

12. The process as claimed in claim 1, wherein R¹ is phenyl or pyridyl, optionally substituted with one or more substituents selected from F, Cl, and CH₃.

13. The process as claimed in claim 1, wherein R² is hydrogen, halogen, cyano, $C_{1-4}$-alkyl, or halo-$C_{1-4}$-alkyl.

14. The process as claimed in claim 1, wherein R² is hydrogen.

15. The process as claimed in claim 1, wherein W is a phenyl ring optionally substituted with one or more substituents as defined in claim 1.

16. The process as claimed in claim 1, wherein W is a 6-membered heteroaryl ring selected from pyridine, pyridazine, pyrazine, and pyrimidine optionally substituted with one or more substituents as defined in claim 1.

17. The process as claimed in claim 1, wherein W is a 5-membered heteroaryl ring selected from oxazole, thiazole, and imidazole optionally substituted with one or more substituents as defined in claim 1.

18. The process as claimed in claim 1, wherein W is an imidazolyl ring optionally substituted as in claim 1, and wherein the imidazolyl ring is connected to the pyrrolopyridine core via an imidazolyl ring carbon atom.

19. The process as claimed in claim 1, wherein W is optionally substituted with one or more substituents selected from fluoro, chloro, cyano, CH₃, and CF₃.

20. The process as claimed in claim 1, wherein V is —CH₂—, —(CH₂)₂—, —N(R⁶)CH₂—, or —CH₂—N(R⁶)—.

21. The process as claimed in claim 1, wherein R³ is cyclopropyl, cyclobutyl, cyclopentyl, or cyclohexyl optionally substituted as defined in claim 1.

22. The process as claimed in claim 1, wherein R³ is formed from NR⁴ᴬR⁴ᴮ, wherein R⁴ᴬ and R⁴ᴮ, together with the nitrogen atom to which they are attached, join together to form a 4-7 membered heterocyclic ring optionally substituted as defined in claim 1.

23. The process as claimed in claim 1, wherein R³ is selected from the group consisting of:

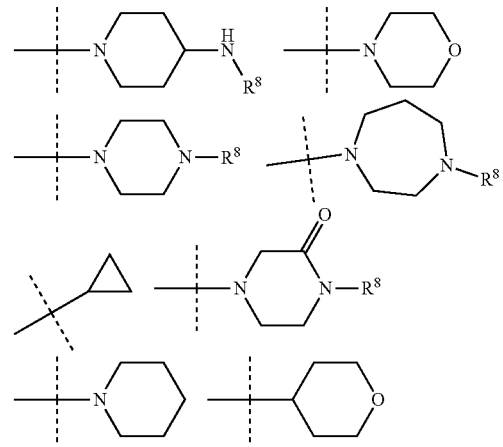

wherein R⁸ is selected from hydrogen, CH₃, —CONH₂, —NHCONH₂, —S(O)₂CH₃, and —COCH₃.

24. The process as claimed in claim 1, wherein R¹ is a phenyl ring, or a 5 or 6-membered heteroaryl ring, the ring being optionally substituted with one or more 3-7 membered cycloalkyl rings.

25. The process as claimed in claim 1, wherein W is a phenyl ring or a 5 or 6-membered heteroaryl ring, the ring being optionally substituted with one or more oxo substituents.

26. The process as claimed in claim 1, wherein R³ is selected from —$C_{1-4}$-alkyl and —$C_{1-4}$-alkyl-$C_{1-4}$-alkoxy.

27. The process as claimed in claim 1, wherein the compound of formula (I) is selected from:
4-[1-(4-Chlorophenyl)-1H-pyrrolo[2,3-c]pyridin-2-yl]pyridine;
2-[1-(4-Chlorophenyl)-1H-pyrrolo[2,3-c]pyridin-2-yl]pyridine;
3-[1-(4-Chlorophenyl)-1H-pyrrolo[2,3-c]pyridin-2-yl]pyridine;
5-[1-(4-Chlorophenyl)-1H-pyrrolo[2,3-c]pyridin-2-yl]pyrimidine;
2-[1-(4-Chlorophenyl)-1H-pyrrolo[2,3-c]pyridin-2-yl]pyrazine;
1-({4-[1-(4-Chlorophenyl)-1H-pyrrolo[2,3-c]pyridin-2-yl]phenyl}carbonyl)-4-methylpiperazine;
4-{5-[1-(4-Chlorophenyl)-1H-pyrrolo[2,3-c]pyridin-2-yl]pyrimidin-2-yl}morpholine;
4-{5-[1-(4-Chlorophenyl)-1H-pyrrolo[2,3-c]pyridin-2-yl]pyrimidin-2-yl}piperazin-2-one;
4-{5-[1-(4-Chlorophenyl)-1H-pyrrolo[2,3-c]pyridin-2-yl]-4-methylpyridin-2-yl}morpholine;
4-{5-[1-(4-Methylphenyl)-1H-pyrrolo[2,3-c]pyridin-2-yl]pyrimidin-2-yl}morpholine;
4-(5-{1-Phenyl-1H-pyrrolo[2,3-c]pyridin-2-yl}pyrimidin-2-yl)morpholine;
4-{5-[1-(4-Bromophenyl)-1H-pyrrolo[2,3-c]pyridin-2-yl]pyrimidin-2-yl}morpholine;

5-[1-(4-Chlorophenyl)-1H-pyrrolo[2,3-c]pyridin-2-yl]-1-methyl-1H-pyrazole;
4-[1-(4-Chlorophenyl)-1H-pyrrolo[2,3-c]pyridin-2-yl]-1-methyl-1H-pyrazole;
5-[1-(4-Chlorophenyl)-1H-pyrrolo[2,3-c]pyridin-2-yl]-1-methyl-1H-imidazole;
5-[1-(4-Chlorophenyl)-1H-pyrrolo[2,3-c]pyridin-2-yl]-N,N-dimethylpyrimidin-2-amine;
4-[1-(4-Chlorophenyl)-1H-pyrrolo[2,3-c]pyridin-2-yl]-1-cyclopropyl-1,2-dihydropyridin-2-one;
5-[1-(4-Chlorophenyl)-1H-pyrrolo[2,3-c]pyridin-2-yl]-N-(oxan-4-yl)pyrimidin-2-amine;
4-({5-[1-(4-Chlorophenyl)-1H-pyrrolo[2,3-c]pyridin-2-yl]pyridin-2-yl}methyl)morpholine;
5-[1-(4-Chlorophenyl)-1H-pyrrolo[2,3-c]pyridin-2-yl]-4-methylpyridin-2-amine;
4-[1-(4-Chlorophenyl)-1H-pyrrolo[2,3-c]pyridin-2-yl]-1,2-dihydropyridin-2-one;
4-[1-(4-Chlorophenyl)-1H-pyrrolo[2,3-c]pyridin-2-yl]-1-methyl-1,2-dihydropyridin-2-one;
4-[1-(4-Chlorophenyl)-1H-pyrrolo[2,3-c]pyridin-2-yl]-1-ethyl-1,2-dihydropyridin-2-one;
6-[1-(4-Chlorophenyl)-1H-pyrrolo[2,3-c]pyridin-2-yl]-1-methyl-1,2-dihydropyridin-2-one;
5-[1-(4-Chlorophenyl)-1H-pyrrolo[2,3-c]pyridin-2-yl]-2,3-dihydropyridazin-3-one;
4-[1-(4-Chlorophenyl)-1H-pyrrolo[2,3-c]pyridin-2-yl]pyridin-2-amine;
3-[1-(4-Chlorophenyl)-1H-pyrrolo[2,3-c]pyridin-2-yl]-5-fluoropyridine;
5-[1-(4-Chlorophenyl)-1H-pyrrolo[2,3-c]pyridin-2-yl]-N-(cyclopropylmethyl)pyrimidin-2-amine;
3-Chloro-5-[1-(4-chlorophenyl)-1H-pyrrolo[2,3-c]pyridin-2-yl]pyridine;
5-[1-(4-Chlorophenyl)-1H-pyrrolo[2,3-c]pyridin-2-yl]-2-(1H-pyrazol-1-yl)pyridine;
4-[1-(4-Chlorophenyl)-1H-pyrrolo[2,3-c]pyridin-2-yl]-3-fluoropyridine;
3-Chloro-4-[1-(4-chlorophenyl)-1H-pyrrolo[2,3-c]pyridin-2-yl]pyridine;
4-[1-(4-Chlorophenyl)-1H-pyrrolo[2,3-c]pyridin-2-yl]-3-methylpyridine;
1-Cyclopropyl-4-{1-phenyl-1H-pyrrolo[2,3-c]pyridin-2-yl}-1,2-dihydropyridin-2-one; and
pharmaceutically acceptable salts thereof.

* * * * *

UNITED STATES PATENT AND TRADEMARK OFFICE
CERTIFICATE OF CORRECTION

PATENT NO. : 10,766,897 B2
APPLICATION NO. : 16/542792
DATED : September 8, 2020
INVENTOR(S) : Max Espensen et al.

Page 1 of 3

It is certified that error appears in the above-identified patent and that said Letters Patent is hereby corrected as shown below:

In the Specification

Columns 15-16, Lines 46-67, and Columns 17-18, Lines 1-26, Scheme 1 please replace:

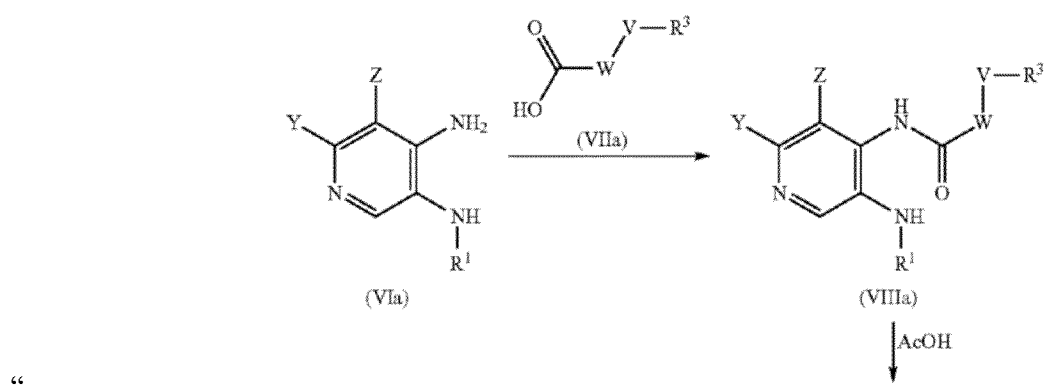

"

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,766,897 B2

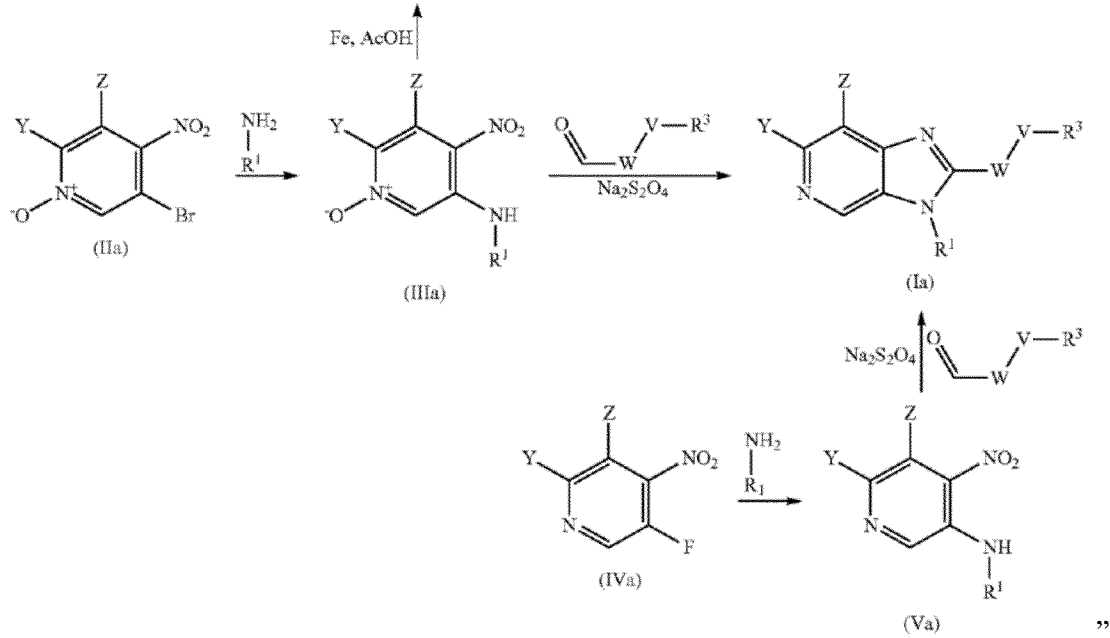

With:

Scheme 1. General synthetic routes for preparation of compounds of formula (I) wherein X is N (i.e. compounds of general formula (Ia))

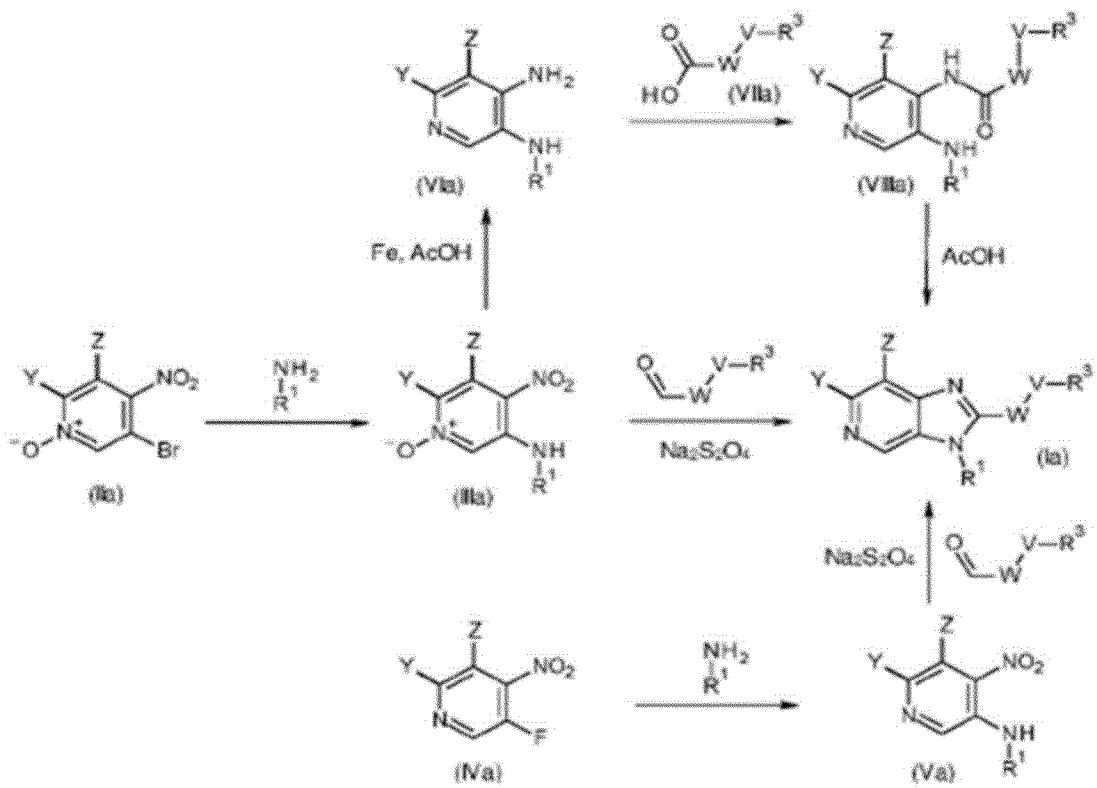

Column 93, Please replace the structure of compound no. 142:
"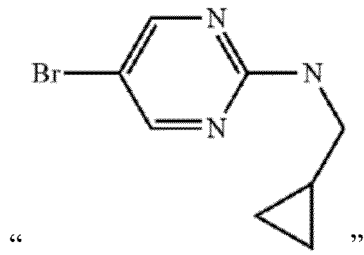"
With:
--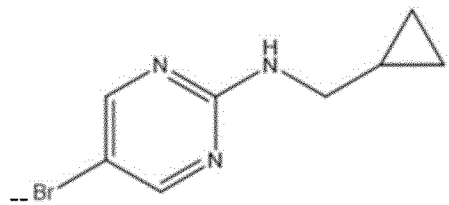--
Column 165, Please replace the structure of compound no. 141:
"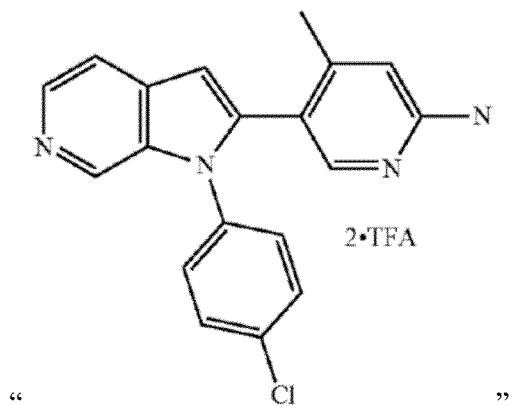"
With:
--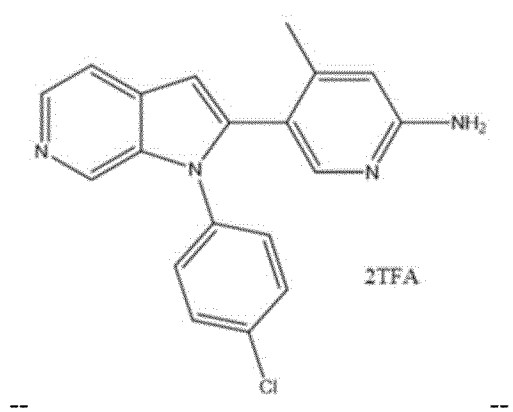--